(12) United States Patent
Cypes et al.

(10) Patent No.: US 7,603,889 B2
(45) Date of Patent: Oct. 20, 2009

(54) SYSTEM FOR MONITORING AND CONTROLLING UNIT OPERATIONS THAT INCLUDE DISTILLATION

(75) Inventors: Stephen Cypes, San Jose, CA (US); Mark Uhrich, Redwood City, CA (US); Eric D. Carlson, Cupertino, CA (US); Oleg Kolosov, San Jose, CA (US); David Padowitz, Mountain View, CA (US); James Bennett, Santa Clara, CA (US); Leonid Matsiev, San Jose, CA (US)

(73) Assignee: MEAS France, Toulouse Cedex (FR)

( * ) Notice: Subject to any disclaimer, the term of this patent is extended or adjusted under 35 U.S.C. 154(b) by 300 days.

(21) Appl. No.: 11/278,340

(22) Filed: Mar. 31, 2006

(65) Prior Publication Data
US 2007/0017291 A1  Jan. 25, 2007

Related U.S. Application Data

(60) Provisional application No. 60/667,818, filed on Apr. 1, 2005.

(51) Int. Cl.
*G01N 29/00* (2006.01)
*G01N 29/04* (2006.01)

(52) U.S. Cl. .................. 73/64.53; 73/61.49; 73/61.79; 73/590

(58) Field of Classification Search ............... 73/61.49, 73/61.79, 64.53, 590
See application file for complete search history.

(56) References Cited

U.S. PATENT DOCUMENTS

| | | | |
|---|---|---|---|
| 5,734,098 | A | 3/1998 | Kraus et al. |
| 6,088,630 | A | 7/2000 | Cawlfield |
| 6,182,499 | B1 | 2/2001 | McFarland et al. |
| 6,336,353 | B2 | 1/2002 | Matsiev et al. |
| 6,393,895 | B1 | 5/2002 | Matsiev et al. |
| 6,401,519 | B1 | 6/2002 | McFarland et al. |
| 6,494,079 | B1 | 12/2002 | Matsiev et al. |
| 6,787,112 | B1 | 9/2004 | Turner et al. |
| 6,924,149 | B2 | 8/2005 | Turner et al. |
| 2002/0178787 | A1 | 12/2002 | Matsiev et al. |

(Continued)

FOREIGN PATENT DOCUMENTS

EP          0304232          2/1989

(Continued)

OTHER PUBLICATIONS

Bozenhardt, H.F., "Modern control tricks solve distillation problems," Hydrocarbon Processing, Gulf Publishing Co., Houston, U.S., vol. 67, No. 6, Jun. 1988, pp. 47-50.

(Continued)

*Primary Examiner*—Daniel S Larkin
(74) *Attorney, Agent, or Firm*—Senniger Powers LLP

(57) ABSTRACT

Fluid sensor methods and systems adapted for monitoring and/or controlling distillation operations in fluidic systems, such as batch distillation operations or continuous distillation operations, are disclosed. Preferred embodiments are directed to process monitoring and/or process control for unit operations involving endpoint determination of a distillation, for example, as applied to a liquid-component-switching operation (e.g., a solvent switching operation), a liquid-liquid separation operation, a solute concentration operation, a dispersed-phase concentration operation, among others.

20 Claims, 49 Drawing Sheets

U.S. PATENT DOCUMENTS

| | | |
|---|---|---|
| 2003/0000291 A1 | 1/2003 | Kolosov et al. |
| 2003/0041653 A1 | 3/2003 | Matsiev et al. |
| 2004/0074302 A1 | 4/2004 | Matsiev et al. |
| 2004/0074303 A1 | 4/2004 | Matsiev et al. |
| 2004/0093932 A1 | 5/2004 | Hajduk et al. |
| 2004/0099050 A1 | 5/2004 | Matsiev et al. |
| 2004/0107055 A1 | 6/2004 | Kolosov et al. |
| 2004/0244487 A1 | 12/2004 | Kolosov et al. |
| 2004/0250622 A1 | 12/2004 | Kolosov et al. |
| 2005/0145019 A1 | 7/2005 | Matsiev et al. |
| 2005/0269244 A1 | 12/2005 | Zare |

FOREIGN PATENT DOCUMENTS

| | | | |
|---|---|---|---|
| JP | 8-68753 | * | 3/1996 |
| WO | 0054044 | | 9/2000 |
| WO | 2004036207 | | 4/2004 |
| WO | 2005066092 | | 7/2005 |

OTHER PUBLICATIONS

Matsiev, L.F., "Application of flexural mechanical resonators to simultaneous measurements of liquid density and viscosity," IEEE Ultrasonics Symposium, 1999, pp. 457-460.

Matsiev, L.F., et al., "Application of low frequency mechanical resonators to liquid property measurements," IEEE Ultrasonics Symposium, 1998, pp. 459-462.

Braile, L., "Seismic wave demonstrations and animations," Purdue University, Earth & Atmosphere Sciences, Dec. 2004, http://www.eas.purdue.edu/~braile/edumod/waves/WaveDemo.htm, pp. 1-15.

* cited by examiner

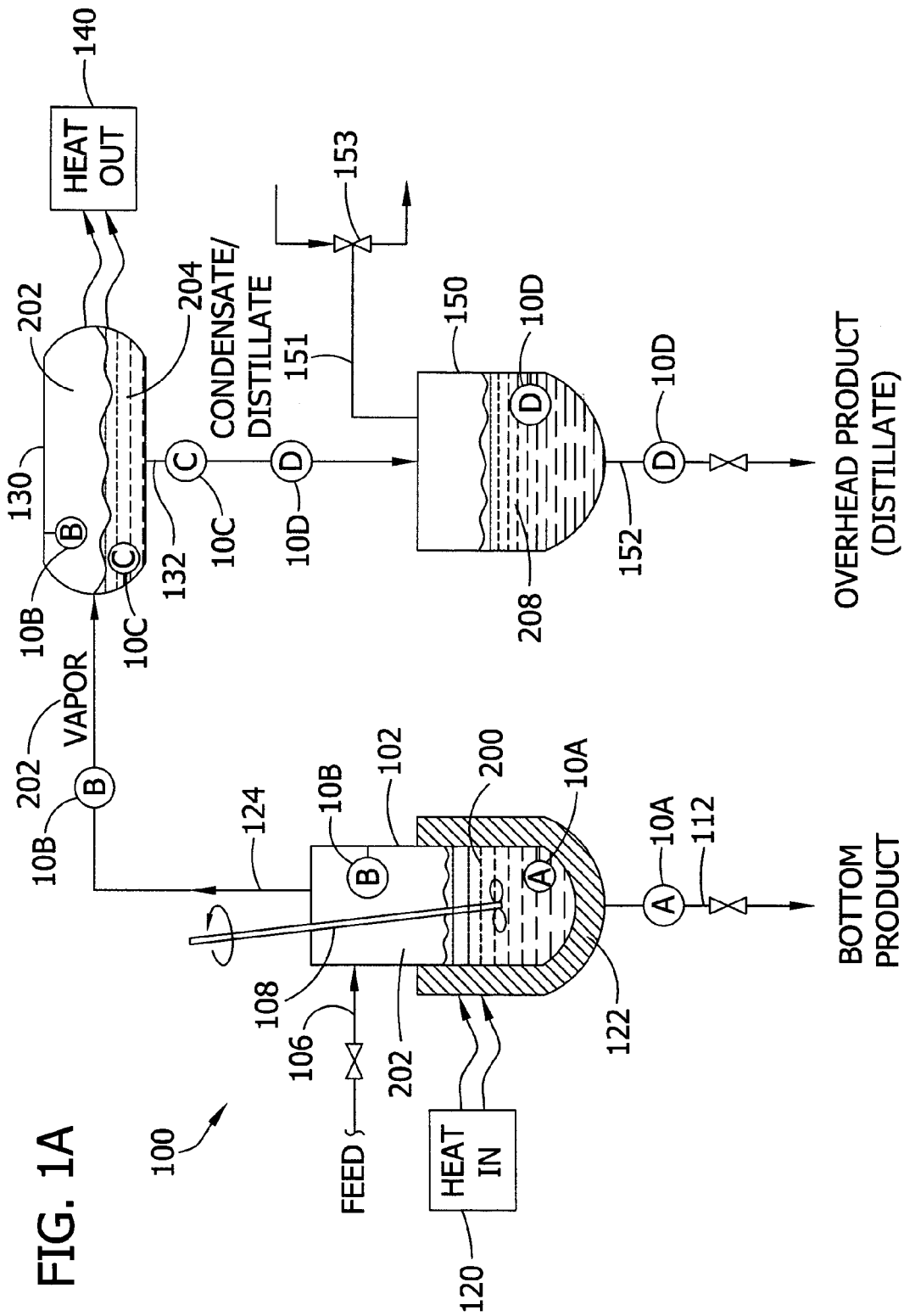

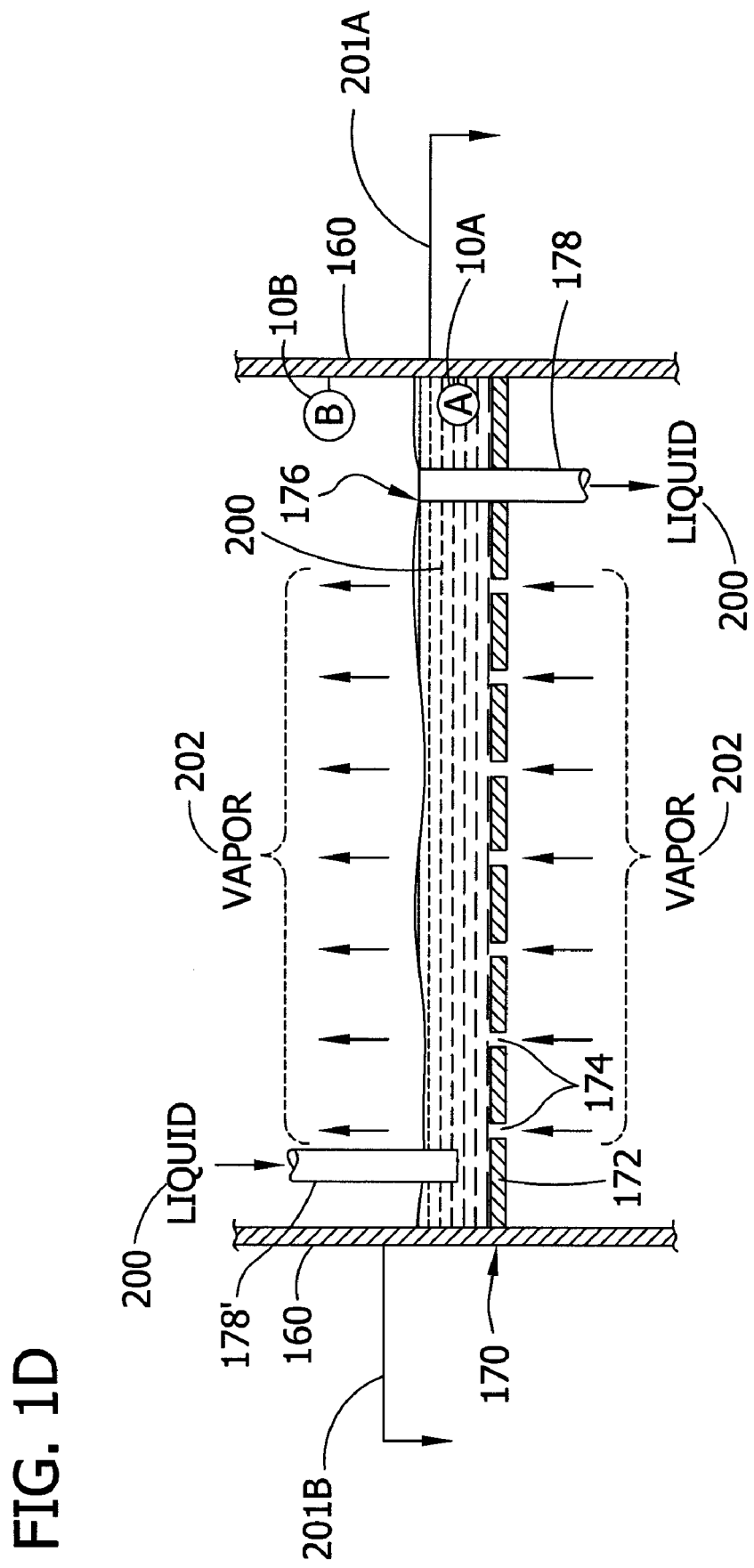

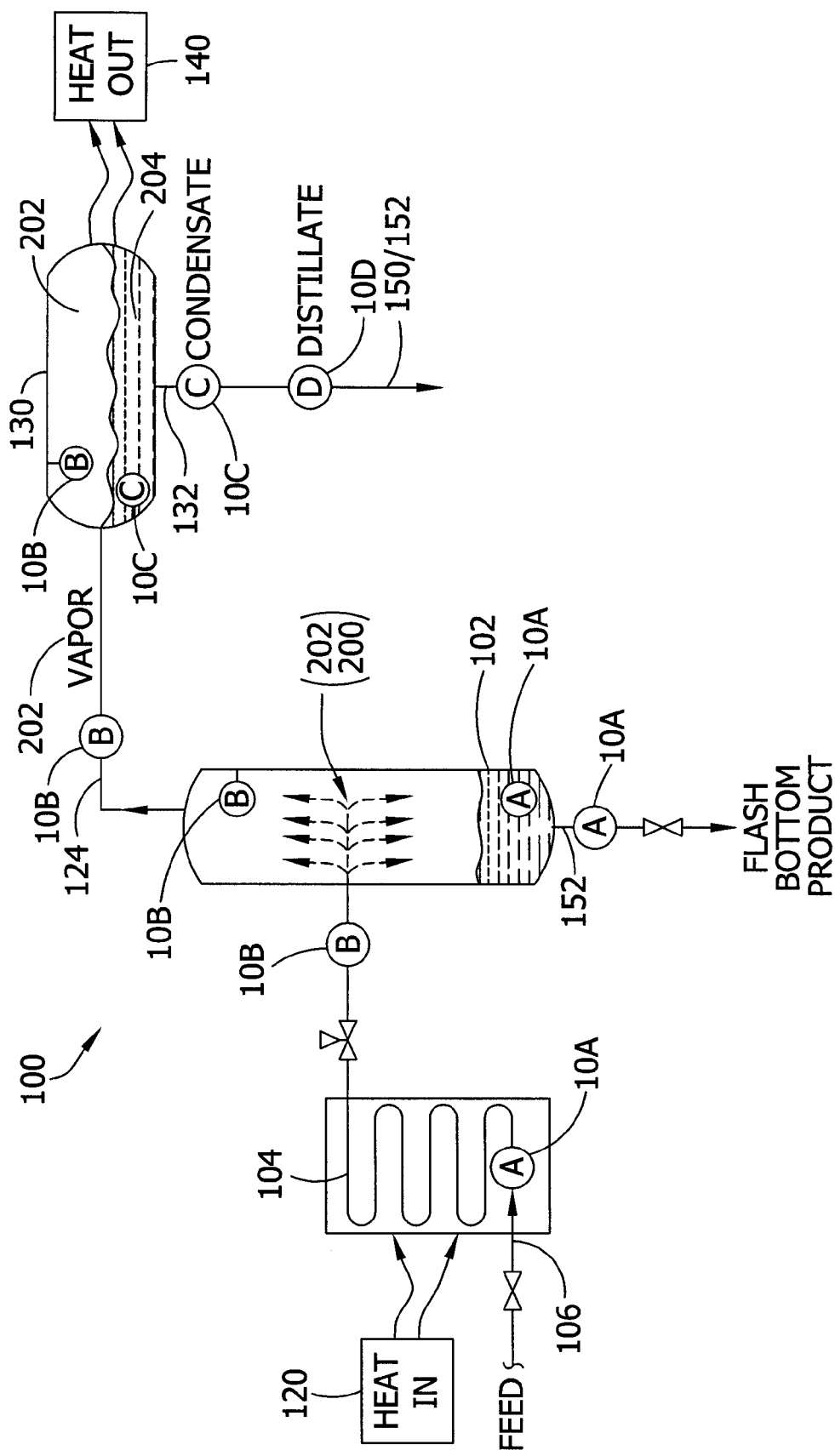

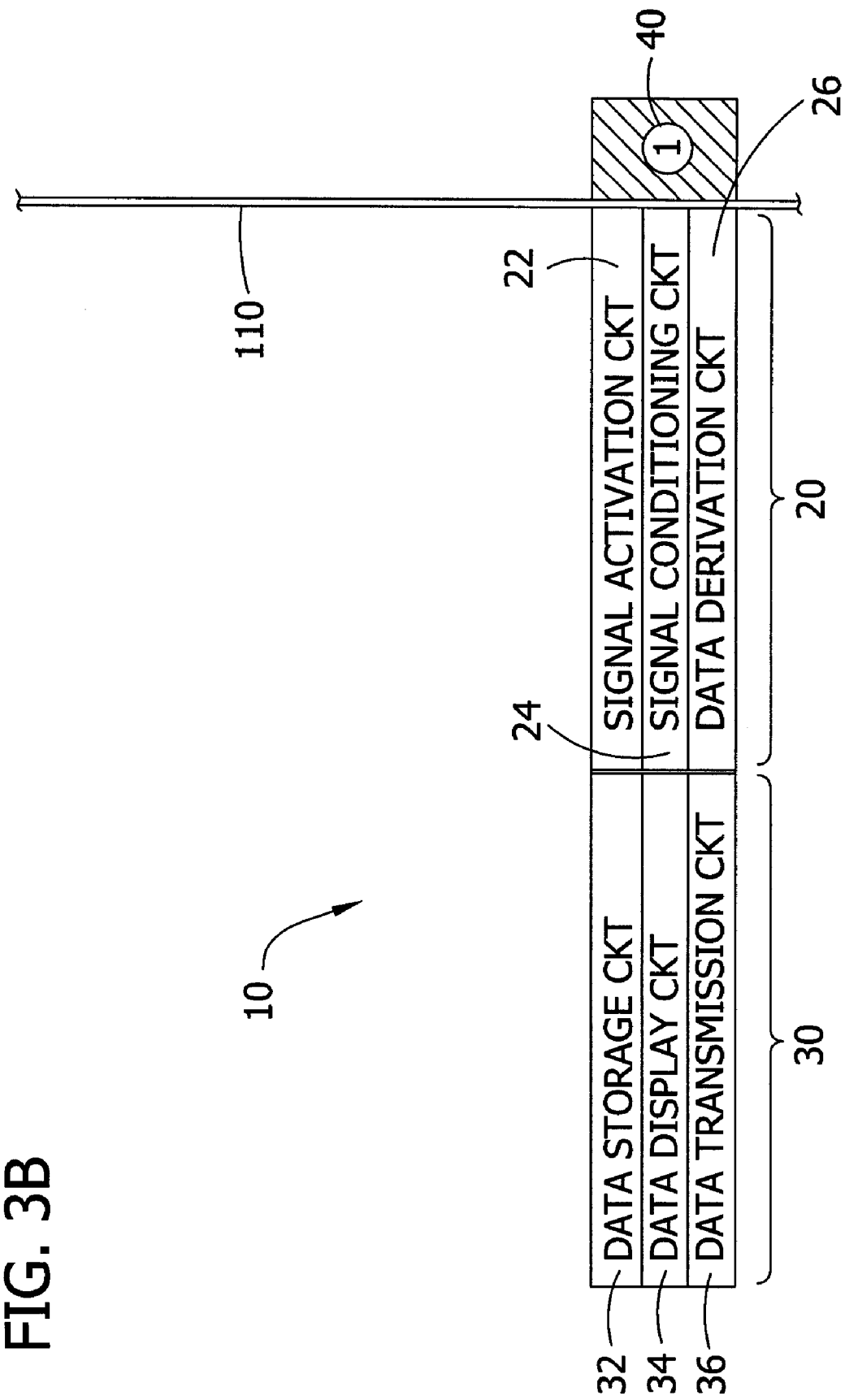

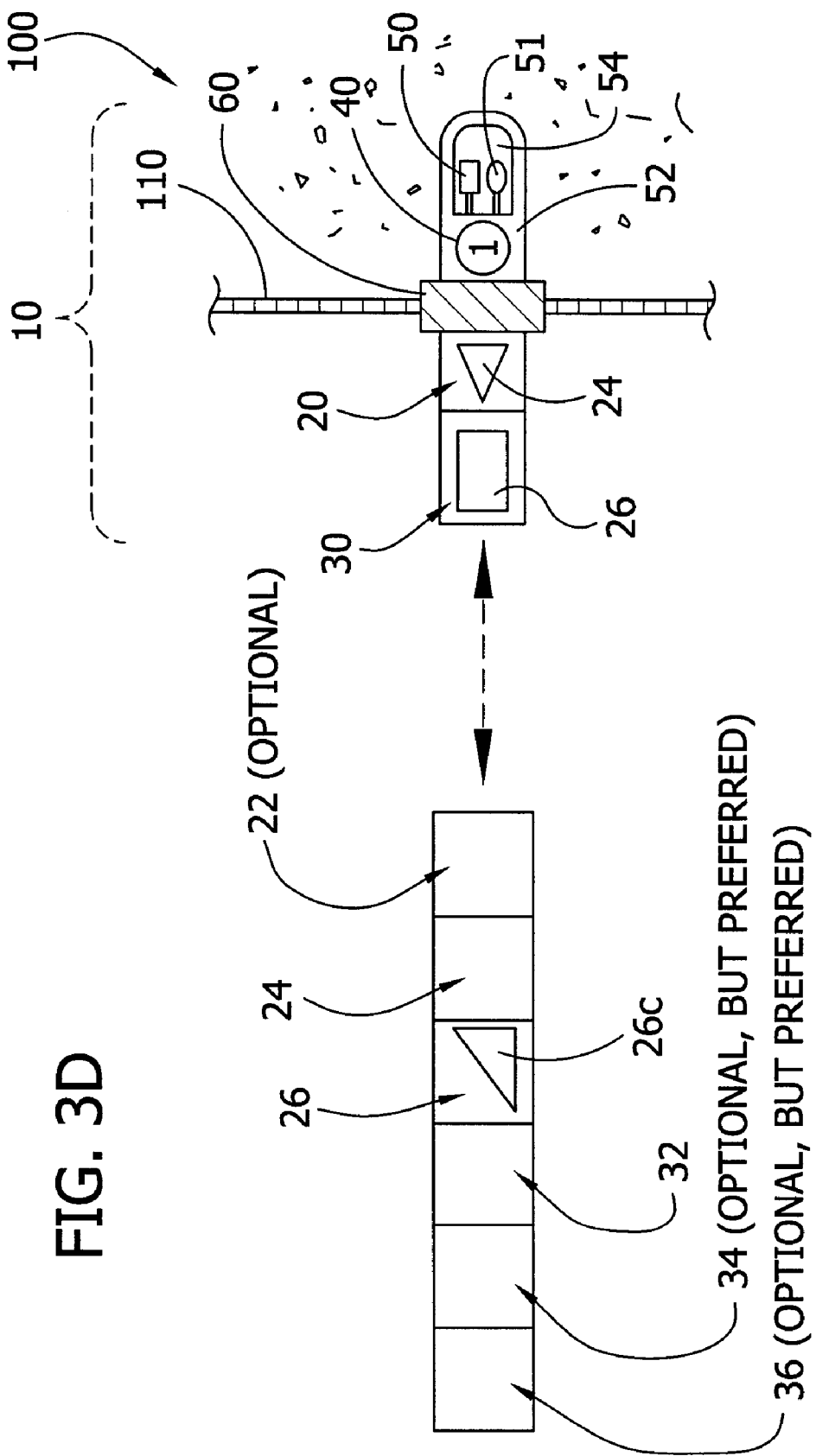

TUNING FORK EQUIVALENT CIRCUIT, $Z_{tf}$

FIG. 5B $$V_{out} \ (Co, Cp, Lo, Cs, Ro, Z(\omega), A, B, \rho, \eta, \omega, \varepsilon) \tag{1}$$

$$V_{out}(\omega) = \frac{V_o(Z_{in}(\omega))}{(Z_{in}(\omega)) + (Z_{tf}(\omega))} \tag{2}$$

$$Z_{in} = R_{in} * (1/i\omega C_{in})(R_{in} + 1/i\omega C_{in})^{-1} \tag{3}$$

$$Z_{tf} = (1/i\omega Cp)(Ro + 1/i\omega Cs + i\omega Lo) \\ (1/i\omega Cp + Ro + 1/i\omega Cs + i\omega Lo)^{-1} \tag{4}$$

$$Z(\omega) = Ai\omega p + B*(\omega\rho\eta)^{1/2}(1+i) \tag{5}$$

$$\varepsilon_{measured} = a + k*Cp_{(measured)} \tag{6}$$

$$\varepsilon_{measured} = [\varepsilon_{cal} - (\varepsilon_{cal} - 1) * [Cp_{cal} / (Cp_{cal} - Cp_o)]] + \\ [Cp_{(measured)} * [(\varepsilon_{cal} - 1)/(Cp_{cal} - Cp_{o(vacuum)})]] \tag{7}$$

$$a = [\varepsilon_{cal} - (\varepsilon_{cal} - 1) * [Cp_{cal} / (Cp_{cal} - Cp_o)]] \tag{8}$$

$$k = [(\varepsilon_{cal} - 1)/(Cp_{cal} - Cp_{o(vacuum)})] \tag{9}$$

$$Cp_{(measured)} \text{ IS A FUNCTION OF "k"} \tag{10}$$

FIG. 5C $$Z(\omega) = Ai\omega\rho + B\sqrt{\omega\rho\eta}\,(1+i)$$

$$Z(\omega) = i\omega\Delta L + \Delta Z\sqrt{\omega}\,(1+i)$$

$$\Delta L = A\rho, \quad \Delta Z = B\sqrt{\rho\eta}$$

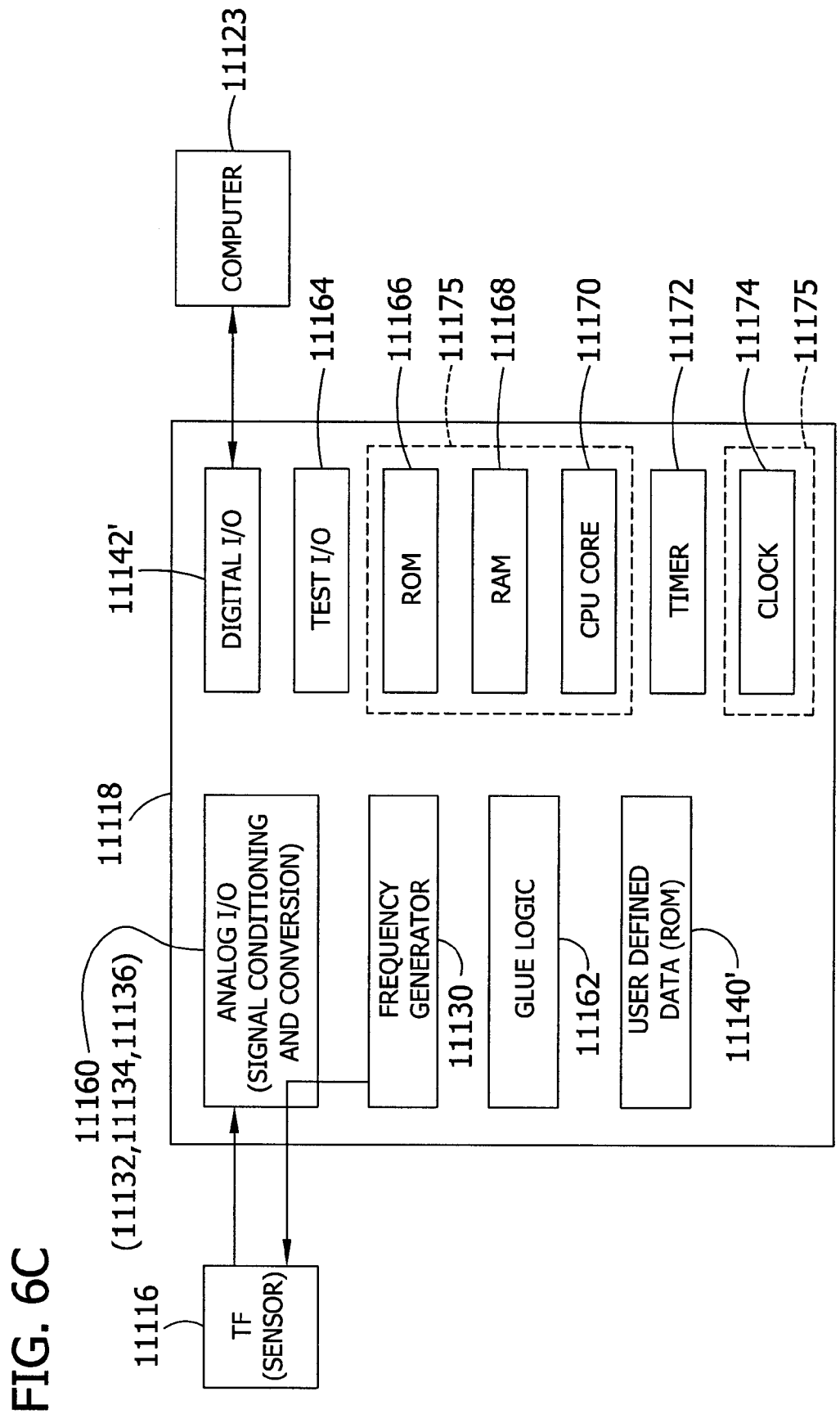

FIG. 6D

APPROXIMATED FLUID CHARACTERISTICS

| TUNING FORK 1.1 TEMP. 25°C | | DENSITY | VISCOSITY | DIELECTRIC CONSTANT |
|---|---|---|---|---|
| | TYPE 1 | $\rho$ | $\eta$ | $\varepsilon$ |
| | TYPE 2 | $\rho$ | $\eta$ | $\varepsilon$ |
| CALIBRATION VARIABLES $V_1$ $V_2$ $V_3$ $V_4$ $V_5$ $V_6$ $V_7$ | TYPE 3 | $\rho$ | $\eta$ | $\varepsilon$ |
| | TYPE 4 | $\rho$ | $\eta$ | $\varepsilon$ |
| | TYPE 5 | $\rho$ | $\eta$ | $\varepsilon$ |
| | TYPE 6 | $\rho$ | $\eta$ | $\varepsilon$ |
| | . | . | . | . |
| | TYPE N | $\rho$ | $\eta$ | $\varepsilon$ |

FIG. 6E

APPROXIMATED FLUID CHARACTERISTICS

| TUNING FORK 1.1 TEMP. 40°C | | DENSITY | VISCOSITY | DIELECTRIC CONSTANT |
|---|---|---|---|---|
| | TYPE 1 | $\rho'$ | $\eta'$ | $\varepsilon'$ |
| | TYPE 2 | $\rho'$ | $\eta'$ | $\varepsilon'$ |
| CALIBRATION VARIABLES $V_1'$ $V_2'$ $V_3'$ $V_4'$ $V_5'$ $V_6'$ $V_7'$ | TYPE 3 | $\rho'$ | $\eta'$ | $\varepsilon'$ |
| | TYPE 4 | $\rho'$ | $\eta'$ | $\varepsilon'$ |
| | TYPE 5 | $\rho'$ | $\eta'$ | $\varepsilon'$ |
| | TYPE 6 | $\rho'$ | $\eta'$ | $\varepsilon'$ |
| | . | . | . | . |
| | TYPE N | $\rho'$ | $\eta'$ | $\varepsilon'$ |

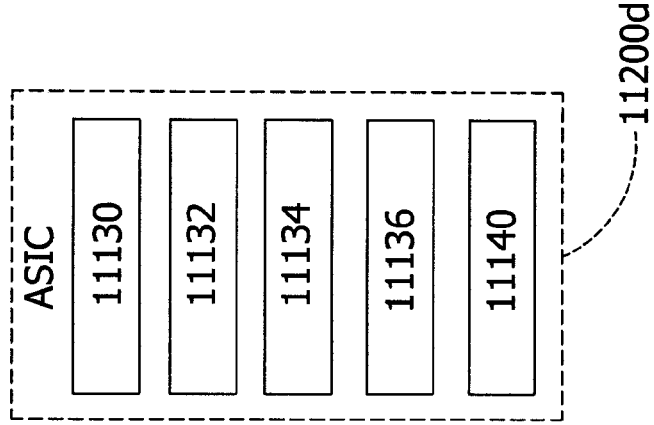
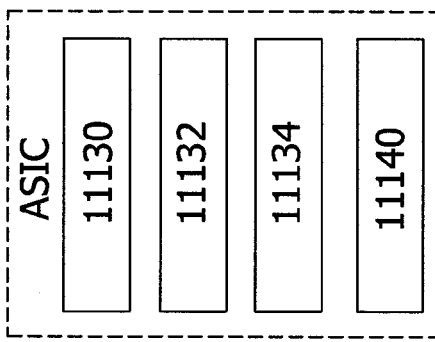
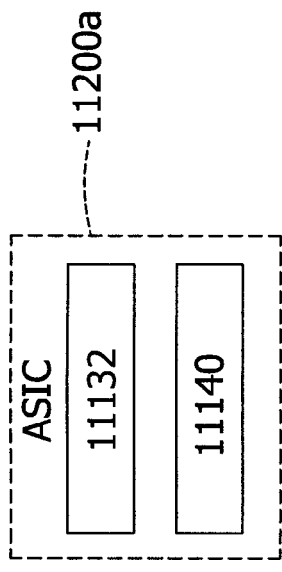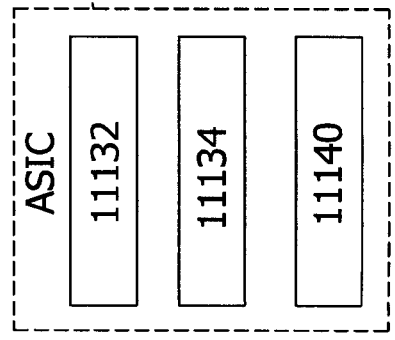

FIG. 22

*Assumed rate expression:*

$$\text{rate} = \frac{d[Adduct]}{dt} = -\frac{d[MA]}{dt} = -\frac{d[FUR]}{dt} \quad \text{Equation (1)}$$

*Must relate rate of density change to rate of reaction:*

$$\frac{d\rho}{dt} = Mass_0 \frac{d(1/V)}{dt} = -\frac{Mass_0}{V^2}\frac{dV}{dt} = -\frac{1}{V}\rho_0 \frac{dV}{dt} \quad \text{Equation (2)}$$

$$\frac{dV}{dt} = \frac{1}{\rho_{MA}}\frac{dMass_{MA}}{dt} + \frac{1}{\rho_{FUR}}\frac{dMass_{FUR}}{dt} + \frac{1}{\rho_{Adduct}}\frac{dMass_{Adduct}}{dt}$$

$$\frac{1}{Mass_0}\frac{dV}{dt} = \frac{1}{\rho_{MA}}\frac{d[MA]}{dt} + \frac{1}{\rho_{FUR}}\frac{d[FUR]}{dt} + \frac{1}{\rho_{Adduct}}\frac{d[Adduct]}{dt}$$

$$= -\frac{1}{\rho_{MA}}\frac{d[Adduct]}{dt} - \frac{1}{\rho_{FUR}}\frac{d[Adduct]}{dt} + \frac{1}{\rho_{Adduct}}\frac{d[Adduct]}{dt}$$

$$= \frac{d[Adduct]}{dt}\left(\frac{1}{\rho_{Adduct}} - \frac{1}{\rho_{MA}} - \frac{1}{\rho_{FUR}}\right) \quad \text{Equation (3)}$$

*Combine Equations (2) and (3):*

$$\text{Rate} = \frac{d\rho/dt}{-\rho_0^2\left(\frac{1}{\rho_{Adduct}} - \frac{1}{\rho_{MA}} - \frac{1}{\rho_{FUR}}\right)}$$

- $d\rho/dt$ — INITIAL RATE OF DENSITY CHANGE
- $\rho_{Adduct}, \rho_{MA}, \rho_{FUR}$ — LIQUID DENSITIES OF ALL SOLUTES, CALCULATED USING THE LeBas METHOD
- Rate — REACTION RATE
- $\rho_0$ — INITIAL MIXTURE DENSITY FIG. 29
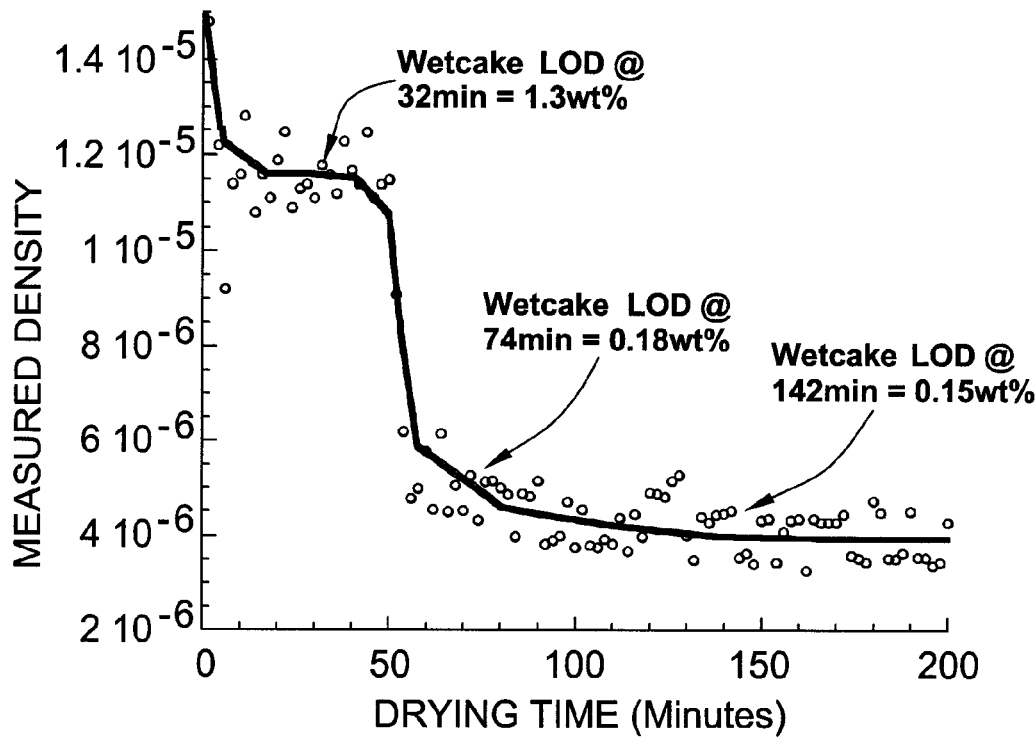
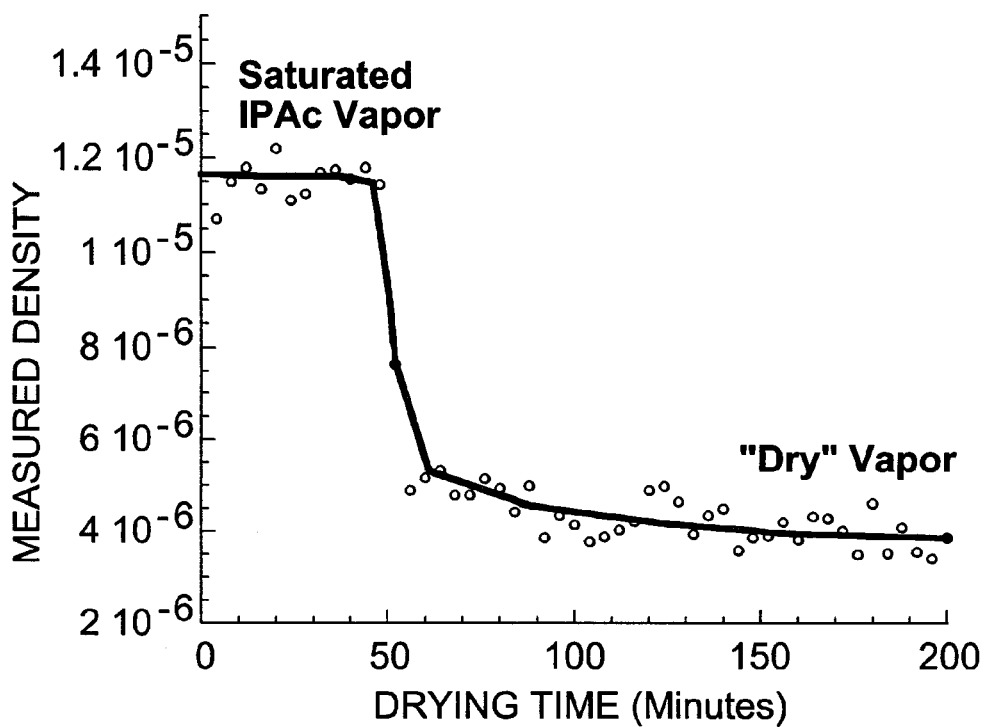

SYSTEM FOR MONITORING AND CONTROLLING UNIT OPERATIONS THAT INCLUDE DISTILLATION

BACKGROUND OF THE INVENTION

The present invention generally relates to the field of fluid sensors and methods, and more particularly to the field of fluid sensors and methods for sensing fluids in unit operations involving separation, especially unit operations involving distillation, evaporation, extraction, drying and/or chemical reaction. Such fluid sensors and methods are suitable for use in process monitoring and/or process control systems and/or operations, and may be especially suitable for example, in the application of Process Analytical Technologies. The present invention relates, in preferred embodiments, to fluid sensor devices and methods adapted for monitoring and/or controlling distillation operations in fluid process systems, such as batch distillation operations or continuous distillation operations. The present invention relates, in particularly preferred embodiments, to process monitoring and/or process control, including devices and methods, for unit operations involving endpoint determination of a distillation, for example, as applied to a liquid-component-switching operation (e.g., a solvent switching operation), a liquid-liquid separation operation, a solute concentration operation, a dispersed-phase concentration operation, etc.

The method also relates to the application of fluid sensor devices in the conduct of other unit operations, including, e.g., evaporation, liquid/liquid extraction, oil seed extraction, drying of solids and various chemical reactions. Commercial applications for such fluid sensors and methods include, for example, process monitoring and/or process control for pharmaceutical development and/or pharmaceutical manufacturing, petroleum refining and industrial chemical manufacturing. In some embodiments, preferred fluid sensors and methods include mechanical resonators, such as flexural resonators. In other embodiments, preferred fluid sensors and methods include other types of sensors, including optical sensors such as refractive index sensors.

Distillation operations are well known in the art. See, generally, for example, McCabe et al., Unit Operations of Chemical Engineering, 3rd Ed., McGraw Hill, Inc. (especially pp. 511-606 and 657-677) (1976). See also, Perry et al., Perry's Chemical Engineer's Handbook, 6th Ed., McGraw Hill, Inc. (especially pp. 13-1 through 13-97) (1984). Generally, a distillations are a common unit operation performed in the pharmaceutical and fine chemical industries, industrial chemical manufacturing and petroleum refining. They are well known in the pharmaceutical industries, for example, in connection with solvent switch operations, and in various industries for the separation of fluid components and the isolation and/or purification of desired products.

In a solvent switch operation, for example, the goal is to switch a substance of interest (such as an active pharmaceutical or an intermediate in the synthesis and/or manufacture thereof) that is dissolved in one or more solvents to another (less volatile) solvent for subsequent processing. This unit operation avoids having to separately workup the substance (e.g., crystallize, filter and dry), and recharge the substance into a new solvent. Typically, a specification is set to define the end point of the solvent switch. This end-point can be defined by the concentration of residual solvent in the residual liquid phase. This specification is typically based on the sensitivity of subsequent processing steps on the presence of the residual solvent. In traditional approaches, such distillation operations are monitored using process conditions such as temperature and/or pressure and/or flow, and end-points are typically determined or confirmed by manual sampling and analysis. For example, a sample would typically be manually obtained from the still or other process vessel. Manual sampling could require an operator, for example, to cool the fluid system to an appropriate temperature (for access and handling), and in some cases to donn appropriate safety clothing, access the fluid system (e.g., through a manway), manually withdraw a sample (e.g., using a dipstick) and transport the sample for off-line analysis (e.g., to an off-site analytical lab for analysis, such as gas chromatography). Significantly, for meaningful analysis, the batch must be held under stable conditions during sampling, transport and off-line measurement. In certain operations, such sampling steps can add potentially 2-3 hours or more onto the batch timecycle.

Hence, there is a need in the art to improve process monitoring and control of separation operations such as distillation operations.

Similar issues are encountered in monitoring and controlling various other fluid process operations, including liquid/liquid extraction, liquid/solid extraction, evaporation, drying and various chemical reactions. Control issues arise in the operation of both batch and continuous processes. In a liquid/liquid extraction process, for example, there is a need to control the operation so that the extract is sufficiently enriched in the solute to be extracted and residual solute content of the raffinate is reduced to a desired level. In evaporation processes, such as, for example, the concentration of caustic solutions emanating from chloralkali cells, there is a need to reach a desired level of concentration and to monitor entrainment of alkali hydroxide and/or alkali metal chlorides in the overhead vapor. In drying operations, there is a need to determine the residual moisture or other volatile content of the solids to be dried. In chemical reactions, there is a need to monitor conversion of reactants to products and in some instances to monitor the formation of by-products. Reaction control presents unique problems in the case of polymerization reactions. Other and somewhat differing issues are presented in the formation of lower molecular weight products, e.g., in chemical or pharmaceutical manufacturing operations.

Control problems are confronted in both batch and continuous processes. In batch processes, the control issue may devolve to identification of an end point of the operation, whether it be distillation, extraction, drying or chemical reaction. In a continuous process, control may typically require adjustment of flow rates, temperatures and pressures to maintain the composition of a product stream, recycle stream, or other process stream at a target value. In either case, there is a need to continually or periodically monitor the composition of a product or other process fraction and adjust process conditions, batch cycles, etc. to maintain a product within a target specification.

On-line measurement techniques are growing in popularity in the process industries where they are known, especially among fine chemical manufacturers, as "Process Analytical Technologies (PAT)." On-line compositional measurements enable the operator to determine the quality of a product batch, or of process material at a particulate point in the flow path of a continuous process without the waste of time and productivity that results from resort to off-line analyses. For various applications, including the monitoring of reactors and batch distillations, e.g., solvent switch distillation, the currently most robust on-line measurement techniques are Near Infrared (NIR) and Fourier Transform Infrared (FTIR). However, because these techniques require substantial capital investment, extensive calibration models, and relatively expensive maintenance, they are difficult to apply in relatively complex operations, especially where there are plural phases in a sample (e.g., in slurry processing where sample handling devices may become plugged with solids), and are difficult to justify in relatively simple operations such as solvent switch wherein at least rough approximations of distillation end points may be determined by monitoring head pressure, overhead vapor temperature and/or still pot temperature.

Effective approaches for measuring characteristics of fluids using mechanical resonators are disclosed in commonly-owned U.S. Pat. Nos. 6,401,519; 6,393,895; 6,336,353; 6,182,499; 6,494,079 and EP 0943091 B1, each of which are incorporated by reference herein for all purposes. See also, Matsiev, "Application of Flexural Mechanical Resonators to Simultaneous Measurements of Liquid Density and Viscosity," IEEE International Ultrasonics Symposium, Oct. 17-20, 1999, Lake Tahoe, Nev., which is also incorporated by reference herein for all purposes. The use of a quartz oscillator in a sensor has been described as well in U.S. Pat. Nos. 6,223,589 and 5,741,961, and in Hammond, et al., "An Acoustic Automotive Engine Oil Quality Sensor", Proceedings of the 1997 IEEE International Frequency Control Symposium, IEEE Catalog No. 97CH36016, pp. 72-80, May 28-30, 1997.

Sensors involving mechanical resonators are known in the art for use in several applications. For example, U.S. Pat. No. 6,182,499 to McFarland et al., discloses mechanical resonator sensors for evaluating fluid properties, especially of an array of fluids in parallel (i.e., simultaneously) and sequentially (e.g., by scanning). Also, PCT Application WO 2004/036207 discloses mechanical resonator sensors in connection with environmental control systems, such as refrigeration systems. PCT application WO 2004/036191 discloses mechanical resonator sensors in connection with machines, such as transportation vehicles.

The use of other types of sensors is also known in the art in connection with various applications. For example, the use of acoustic sensors has been addressed in applications such as viscosity measurement in J. W. Grate, et al, Anal. Chem. 65, 940A948A (1993)); "Viscosity and Density Sensing with Ultrasonic Plate Waves", B. A. Martin, S. W. Wenzel, and R. M. White, Sensors and Actuators, A21-A23 (1990), 704708; "Preparation of chemically etched piezoelectric resonators for density meters and viscometers", S. Trolier, Q. C. Xu, R. E. Newnham, Mat.Res. Bull. 22, 1267-74 (1987); "On-line Sensor for Density and Viscosity Measurement of a Liquid or Slurry for Process Control in the Food Industry", Margaret S. Greenwood, Ph.D. James R. Skorpik, Judith Ann Bamberger, P.E. Sixth Conference on Food Engineering, 1999 AIChE Annual Meeting, Dallas, Tex.; U.S. Pat. Nos. 5,708,191; 5,886,250; 6,082,180; 6,082,181; and 6,311,549; and "Micromachined viscosity sensor for real-time polymerization monitoring", O. Brand, J. M. English, S. A. Bidstrup, M. G. Allen, Transducers '97, 121-124 (1997). See also, U.S. Pat. No. 5,586,445 ("Low Refrigerant Charge Detection Using a Combined Pressure/Temperature Sensor").

As noted above, there remains a need in the art for alternative or improved sensor devices and methods for efficiently sensing, monitoring or evaluating fluids in unit operations involving separations such as unit operations involving distillation, extraction, evaporation, drying and/or chemical reaction. Examples of commercial areas in which such a need exists include for example, such fluid process systems used in connection with the petroleum, chemical, and pharmaceutical industries. In particular, there remains a need in the art for effectively sensing one or more fluids in unit operations involving separations using relatively straightforward, cost-effective, scalable systems and methods, with requisite accuracy and precision.

SUMMARY OF THE INVENTION

It is therefore an object of the present invention, certain and/or various embodiments of the present invention, to provide sensor devices and methods for efficiently sensing, monitoring, controlling and/or evaluating (e.g., determining properties of) fluids used in fluid process systems. In particular, it is an object of the invention to provide cost-effective, practical approaches for sensing, monitoring, controlling and/or evaluating fluids in connection with unit operations involving separation of components of a fluid, such as distillation operations, solvent extraction, evaporation, drying, and chemical reaction. In preferred embodiments, it is an object of the invention to provide devices and methods for sensing, monitoring and/or controlling unit operations involving end-point determinations including, for example, distillation end points in a liquid-component-switching operation (e.g., a solvent switching operation), liquid-liquid separation operations, solute concentration operations, a dispersed-phase concentration operation, etc.

Briefly, therefore, the present invention is broadly directed to various methods for monitoring and/or controlling a unit operation that includes separating one or more components of a multi-component composition by distillation. Preferably, the unit operation is effected in combination with one or more sensors and sensing operations. In some preferred embodiments, the sensor comprises one or more resonators such as one or more mechanical resonators. In some particularly preferred embodiments, the sensor comprises one or more resonators including at least one flexural resonator.

Generally, the invention is directed to a method for monitoring a process comprising altering the composition of a feed mixture, especially where the composition is altered in the course of a unit operation such as, for example, distillation, evaporation, extraction, drying, and/or chemical reaction. In accordance with the method, a sensing surface of a mechanical resonator is contacted with a fluid selected from the group consisting of the altered mixture and another phase produced in altering the mixture. The resonator is stimulated while in contact with the fluid, and the response of the resonator is monitored.

A first aspect of the invention is directed to methods for monitoring and/or for controlling a unit operation that includes separating one or more components of a multicomponent composition by distillation. Generally, in this aspect, a multi-component composition comprising one or more liquid components is provided (e.g., contained in or flowing through a process container such as a process vessel or a process pipeline or process conduit), and at least a portion of at least one liquid component of the multi-component composition is vaporized to form a vapor. The vapor is condensed to form a condensate. At least a portion of the condensate is recovered as a distillate. The process of the distilling operation can be monitored and/or controlled using one or more sensors. In one first approach, the sensor includes a mechanical resonator. In this first approach a sensing surface of a mechanical resonator is contacted with a fluid involved with the distillation operation. The fluid can be, for example, one or more of the multi-component composition, the vapor, the condensate or the distillate. The fluid-contacted resonator is stimulated (actively or passively), and a response of the resonator (to the stimulation) is monitored. In another, second approach, the sensor can be, generally, an on-line sensor configured to monitor one or more of the vapor, the condensate or the distillate. In this second approach, at least one on-line sensor is other than a temperature sensor, pressure sensor or flow sensor. Preferably, the on-line sensor is a sensor effective for monitoring a composition-dependent fluid property.

In another second aspect, the invention is directed to a method for monitoring and/or for controlling a reaction. In this aspect, a multi-component composition is provided in a process vessel. The multi-component composition is a solution or a dispersion comprising one or more liquid components and at least one non-polymeric organic component dissolved or dispersed in the one or more liquid components. The at least one non-polymeric organic component is reacted in the process vessel under reaction conditions. The progress of the reaction in the process vessel can be monitored and/or controlled by a method that includes (i) contacting a sensing surface of a mechanical resonator with the multi-component composition at a first time during the reaction, stimulating the composition-contacted resonator at the first time, and monitoring a response of the resonator associated with the first time, and thereafter (ii) contacting a sensing surface of the mechanical resonator with the multi-component composition at a second time during the reaction, stimulating the composition-contacted resonator at the second time, and monitoring a response of the resonator associated with the second time.

The inventions are generally directed, in another third aspect, to a method for monitoring and/or controlling a reaction mixture or components thereof. In this method, one or more liquid components are provided in a process vessel, and at least one non-polymeric organic component in provided in the process vessel. The at least one non-polymeric organic component is dissolved or dispersed in the one or more liquid components to form a solution or dispersion, respectively. Optionally, additional reactants can be provided to the process vessel to form a reaction mixture. One or more of the fluids provided to the process vessel or contained within the process vessel are monitored using a mechanical resonator sensor. The monitored fluids can be selected from the one or more liquid components, the at least one non-polymeric organic component, the solution or dispersion, the reaction mixture, and combinations thereof. The fluid is monitored by a method that includes contacting a sensing surface of a mechanical resonator with the fluid, stimulating the fluid-contacted resonator, and monitoring a response of the resonator.

The invention is also broadly directed, in a fourth aspect, to various systems for monitoring and/or controlling a unit operation that includes separating one or more components of a multi-component composition by distillation. The systems generally comprise a sensor in combination with a distillation system. In some preferred embodiments, the sensor comprises at least one resonator. In especially preferred embodiments, the sensor comprises one or more mechanical resonators including at least one flexural resonator. Generally, the system comprises a fluid system configured for distillation and one or more sensors configured in association with the fluid system such that the sensor can monitor a fluid within the system. Generally, the fluid system can comprise (i) a process container for providing a multi-component composition comprising one or more liquid components, (ii) a heat source associated with the process container and adapted for vaporizing at least a portion of at least one liquid component of the composition to form a vapor, (iii) a condenser in fluid communication with the process container for receiving the vapor, (iv) a heat sink associated with the condenser for condensing the vapor to form a condensate, and (v) a distillate receiver for recovering at least a portion of the condensate as a distillate. In a first approach with respect to this aspect of the invention, system can comprise a mechanical resonator sensor comprising a mechanical resonator. The mechanical resonator sensor can be configured in association with the fluid system such that a sensing surface of the mechanical resonator can contact a fluid within the fluid system (e.g., the fluid being any of the multi-component composition, the vapor, the condensate or the distillate). The mechanical resonator sensor can further comprise one or more electrical circuits in signaling communication with the mechanical resonator. The one or more electrical circuits comprising signal processing circuitry or data retrieval circuitry or combinations thereof. In another, second approach to this aspect of the invention, the system can comprise an on-line sensor (other than a temperature sensor, a pressure sensor and a flow sensor), the on-line sensor being configured in association with the fluid system such that the sensor can monitor a fluid within the fluid system. The monitored fluid can be the vapor, the condensate or the distillate. Preferably, the on-line sensor is adapted for determining one or more fluid-composition-dependent properties of the vapor, the condensate or the distillate.

The invention is further directed to a method for monitoring the moisture content of a hygroscopic fluid. In such applications, the method comprises contacting a sensing surface of a mechanical resonator with the hygroscopic liquid, stimulating the resonator while in contact with the fluid, and monitoring the response of the resonator.

In any case (including any generally recited method or system as set forth above and/or as specifically recited in the following detailed description), in preferred method and system approaches and embodiments, the sensor comprises one or more flexural resonators. The one or more flexural resonators can comprise a flexural resonator sensing element having a sensing surface for contacting the fluid being sensed. In operation during a sensing period, the sensing surface of a flexural resonator displaces or is displaced by at least a portion of the fluid being sensed. The flexural resonator sensor can be operated passively or actively, and if actively operated, is preferably excited using a stimulus signal. The particular nature of the stimulus signal is not critical, but in some embodiments, the stimulus signal can be a waveform having a frequency (e.g., a predetermined frequency) or having a range of frequencies (e.g., being swept over a determined or predetermined range of frequencies), and in each such case, having a frequency or a range of frequencies of less than about 1 MHz. In some embodiments, additional sensors (e.g., such as temperature and/or pressure sensors) can be employed in the systems and methods in combination with the one or more mechanical resonators (preferably, flexural resonators). In some embodiments, alternative sensors can be employed in place of a mechanical resonator sensor. Further discussion of preferred sensors and sensor subassemblies (comprising or more components of a sensor), as well as the preferred use thereof, are described hereinafter.

The monitoring methods of the invention are especially and advantageously adapted to monitoring and control of unit operations in industrial manufacturing processes comprising production of chemicals, production of pharmaceuticals, refining of petroleum, recovery and isolation of desirable products from natural sources, etc. However, the monitoring methods of the invention are also useful as tools in the evaluation and design of unit operations based on observations obtained in a laboratory, pilot plant, semi-works, or even full scale industrial context, e.g., in the evaluation of the kinetics or biological reaction, the scaleup of agitation for a chemical reaction, and the like. "Industrial" manufacturing, extraction or refining process operations are understood by those skilled in the art to be distinguishable from research and development applications. Typically, industrial operations are characterized by one or more of the following attributes: (a) they are conducted to manufacture a product for commercial sale; and/or (b) they are conducted on a scale several orders of magnitude larger than any corresponding research operations; and/or (c) they are operated and controlled to operate consistently and routinely under a prescribed set of conditions and/or procedures; and/or (c) they are operated in facilities requiring a substantial allocation of land and/or capital investment; (e) they are conducted on a sustained basis over several days, one or more weeks, one or more months, or more than one year; and/or (f) they are operated and controlled to yield a product at a cost not substantially greater than, and ordinarily less than, a market price for the product.

Generally, the various approaches and embodiments of the methods and systems of the invention as summarized hereinbefore and described in further detail hereinafter are particularly advantageous with respect to many diverse types of fluids in many diverse types of applications of separation operations such as distillation operations.

As noted above, the methods and systems of the invention are generally advantageous with respect to sensing, monitoring and/or evaluating (e.g., determining one or more properties) fluids being processed through separation operations such as distillation operations, solvent extraction, evaporation or drying. The methods and systems of the invention are particularly advantageous in connection with process control applications for such operations. In general, commercial benefit is realized by industrial efficiency and improved quality control afforded by on-line sensing capabilities of the present invention. Commercial benefit is also realized by relative simplicity and lower costs with respect to sensor deployment, sensor operation, sensor maintenance, sensor repair and/or replacement. Further advantages are also realized with respect to particular applications, some of which are described herein and in the Detailed Description of the invention.

The advantages of the methods and systems of the invention allows for applications of the methods and systems of the invention across diverse industries, including for example, across industries such as the petroleum, chemical, pharmaceutical, healthcare and environmental industries.

The present invention offers substantial advantage over conventional sensor systems, in that multiple specific composition-dependent fluid properties (e.g., density, viscosity, dielectric) can be determined—using the same sensor. Obtaining data for multiple properties using a single sensor or sensor system affords opportunities for more sophisticated process monitoring and process control, including for example monitoring and/or controlling a process based on multiparametric data values (typically derived using statistical data analysis).

Significantly, the advantages of the method and system can also be employed across various product development stages, including discovery stage and optimization stage on a research (lab) scale operations, pilot plant scale operations, and commercial scale operations. This inter-scale sensing capability affords improved efficiency and quality of scale-up for commercial material candidates, and therefore, improves overall product development timelines and costs.

The present invention is further directed to various methods for monitoring a manufacturing, extraction or refining process. In various such embodiments, the process comprises altering the composition of a feed mixture and the method comprises contacting a sensing surface of a mechanical resonator and monitoring the response of the resonator. The fluid is selected from the group consisting of a fluid phase comprising the altered mixture, another phase produced in altering the composition of the mixture, and combinations thereof.

The present invention is also directed to methods for monitoring a unit operation comprising distillation. In various such embodiments, the method comprises introducing a second solvent into a feed mixture comprising a feed solution comprising a first solvent and a solute, thereby producing a mixed solvent solution comprising the first solvent, the second solvent and the solute and vaporizing a portion of the mixed solvent solution under conditions of temperature and pressure at which the volatility of the second solvent is lower than the volatility of the first solvent, to provide a primary vapor fraction enriched in the first solvent relative to the mixed solution and a residual liquid phase enriched in the second solvent relative to the mixed solution. The method further comprises contacting a sensing surface of a mechanical resonator with a fluid selected from the group consisting of the primary vapor fraction, a distillate fraction condensed from or in equilibrium with the primary vapor fraction, the residual liquid fraction, a secondary vapor fraction flashed from or in equilibrium with the residual liquid fraction, and combinations thereof, and monitoring the response of the resonator.

In still further embodiments, the present invention is directed to methods for monitoring a unit operation comprising liquid/liquid extraction. The unit operation comprises contacting a liquid feed mixture with another liquid that is immiscible with the feed mixture but comprises a solvent for a component of the liquid feed mixture, thereby causing transfer of the component from the liquid feed mixture to the another liquid, producing an extract comprising the solvent and the transferred component, and altering the composition of the liquid feed mixture to produce a raffinate having a reduced concentration of the transferred component. The monitoring method comprises contacting a sensing surface of a mechanical resonator with a fluid selected from the group consisting of the feed mixture, the extract, the raffinate, and combinations thereof, and monitoring the response of the resonator.

The present invention is also directed to methods for monitoring a process comprising a unit operation comprising evaporation. The process comprises vaporizing a portion of a liquid feed mixture comprising a liquid solvent and a solute dissolved in the solvent, thereby producing a vapor phase comprising the solvent and a residual liquid phase having an increased concentration of the solute in the solvent. The method comprises contacting a sensing surface of a mechanical resonator with a fluid selected from the group consisting of the vapor phase, a condensate condensed from the vapor phase, the residual liquid, a fluid dispersion comprising the residual liquid phase, and combinations thereof, and monitoring the response of the resonator.

In still further embodiments, the present invention is directed to a method for monitoring a unit operation comprising removal of another condensed phase component from a feed mixture comprising a solid component and the another condensed phase component, the method comprising contacting a mechanical resonator with a fluid phase comprising the component removed from the feed mixture, and monitoring the response of the resonator.

The present invention is also directed to various methods for monitoring a unit operation comprising membrane separation. The membrane separation comprises introducing a feed mixture into a feed zone on an upstream side of a membrane separator at a pressure higher than the pressure in a permeate zone on the other side of the membrane, passage of fluid through the membrane yielding a permeate in the permeate zone and a retentate or tangential flow fraction in the feed zone or in a discharge stream exiting the feed zone. The method for monitoring the unit operation comprises contacting a mechanical resonator with a fluid phase selected from the group consisting of the feed mixture, the permeate, the retentate, the tangential flow fraction and combinations thereof, and monitoring the response of the resonator.

In various other embodiments, the present invention is directed to various methods for monitoring a process comprising a unit operation comprising sorption. Typically, the unit operation comprises contacting a fluid feed mixture with a sorbent, and sorbing a component of the feed mixture into or onto the sorbent, thereby yielding a fluid fraction depleted in the sorbed component. The method for monitoring the unit operation comprises contacting a fluid phase representative of the extent and/or effectiveness of the sorption with a mechanical resonator, and monitoring the response of the resonator.

The present invention is also directed to various methods for monitoring a unit operation comprising crystallization. The unit operation comprises processing a solution comprising a solute to be crystallized to effect precipitation of the solute. The method for monitoring the unit operation comprises contacting a sensing surface of a mechanical resonator with a fluid representative of the crystallization, and monitoring the response of the resonator.

The present invention is also directed to methods for monitoring a non-polymeric chemical reaction, the method comprising contacting a sensing surface of a mechanical resonator with a fluid phase selected from the group consisting of a fluid reaction medium in which the reaction is or has been conducted, a fluid comprising a source of a reactant for the reaction, a fluid comprising a catalyst or source of catalyst for the reaction, a fluid comprising a product of the reaction, a fluid comprising a by-product of the reaction, a fluid that is separated from a fluid reaction medium during or after the reaction, and combinations thereof. The method further comprises monitoring the response of the resonator.

In various other embodiments, the present invention is directed to methods for monitoring the condition of a hygroscopic liquid, the method comprising contacting a sensing surface of a mechanical resonator with the liquid, and monitoring the response of the resonator.

In still further embodiments, the present invention is directed to various methods for monitoring a process comprising distillation of a feed mixture comprising a plurality of components. The method comprises introducing the feed mixture into a distillation column in a feed stage that is below a rectification zone comprising a plurality of rectification stages and/or above a stripping zone comprising a plurality of stripping stages; generating a primary vapor fraction and a residual liquid phase in the distillation column. The sensing surface of a mechanical resonator is contacted with: (i) a fluid comprising the primary vapor fraction or a distillate fraction condensed from or in equilibrium with the primary vapor fraction in the top stage of such rectification zone or an intermediate rectification stage between the feed stage and the top stage; and/or (ii) a fluid comprising the residual liquid fraction or a secondary vapor fraction generated from or in equilibrium with the residual liquid fraction in the bottom stage of the stripping section or an intermediate stripping stage between the feed stage and the bottom stage. The process further comprises stimulating the resonator while in contact with the fluid and monitoring the response of the resonator.

The present invention is also directed to various methods for evaluating a parameter of the kinetics of a chemical reaction, the method comprising contacting a sensing surface of a mechanical resonator with fluid selected from the group consisting of a fluid reaction medium in which the reaction is or has been conducted, a fluid comprising a source of a reactant for the reaction, a fluid comprising a catalyst or source of catalyst for the reaction, a fluid comprising a product of the reaction, a fluid comprising a by-product of the reaction, a fluid that is separated from a fluid reaction medium during or after the reaction, and combinations thereof. The process further comprises stimulating the sensor while in contact with the fluid, monitoring the response of the resonator, and deriving a kinetic parameter of the reaction from data obtained by monitoring the response.

The present invention is further directed to methods for determining the temperature at which a test solution comprising a known concentration of a solute in a solvent is at its maximum metastable supersaturation concentration. Typically, the method comprises preparing the test solution at a temperature sufficient to cause all of the solute to be dissolved, cooling the solution while the solution is in contact with a mechanical resonator, and monitoring the temperature during cooling and the response of the resonator to detect precipitation, the known concentration of the test solution constituting the maximum metastable supersaturated solution concentration at the precipitation temperature.

In accordance with one or more of the foregoing embodiments, the process or unit operation monitored may be an industrial process or unit operation. Additionally or alternatively, in accordance with one or more of the foregoing embodiments, the mechanical resonator utilized is typically a flexural mechanical resonator.

Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

FIGS. 1A through 1E are schematic representations of various fluid systems configured for distillation and of components thereof. Fluid systems, as illustrated, are suitable for single-stage batch, semi-continuous or continuous distillations (FIG. 1A), for multi-stage batch, semi-continuous or continuous distillations (FIG. 1B), for multi-stage continuous distillations (FIG. 1C) and for continuous flash distillation (FIG. 1E), as well. A schematic side sectional view of a portion of distillation column that includes a sieve plate is also illustrated (FIG. 1D).

FIGS. 3A through 3D illustrate sensors suitable for use in connection with the general methods and systems of the invention, including schematic representations illustrating one embodiment in which a sensor comprises multiple mechanical resonators (designated by circled numbers 1, 2 and 3) linked in communication with one or more circuits through a common communication path (FIG. 3A), and illustrating embodiments in which the circuits comprise signal processing circuitry and/or data retrieval circuitry, generally (FIG. 3A), with various detailed configurations (FIG. 3B and FIG. 3C), and with the one or more circuits being configured to be partially local and partially remote (for example, as a ported sensor subassembly) (FIG. 3D).

FIGS. 5A through 5C are a schematic representation of an equivalent circuit for a sensor comprising a flexural resonator sensing element (FIG. 5A) and of equations relating thereto (FIG. 5B and FIG. 5C).

FIGS. 6A through 6C are schematic representations of one preferred approach for circuitry that can be used in connection with the various embodiments of the invention, at least a portion of the circuitry being realized in an application specific integrated circuit (ASIC). FIGS. 6D and 6E illustrate exemplary data that may be stored within a memory comprising user-defined data.

FIGS. 7A through 7D are schematic representations of alternative approaches for realizing circuitry in an ASIC.

FIG. 22 presents equations reflecting a kinetic analysis of the reaction of Example 6 based on the density response illustrated in FIGS. 17 and 19;

FIG. 29 is a plot similar to that of FIG. 28 but in which the resonator frequency sweep rate is reduced to increase the signal to noise ratio, as described in Example 9.

Figure 1B:
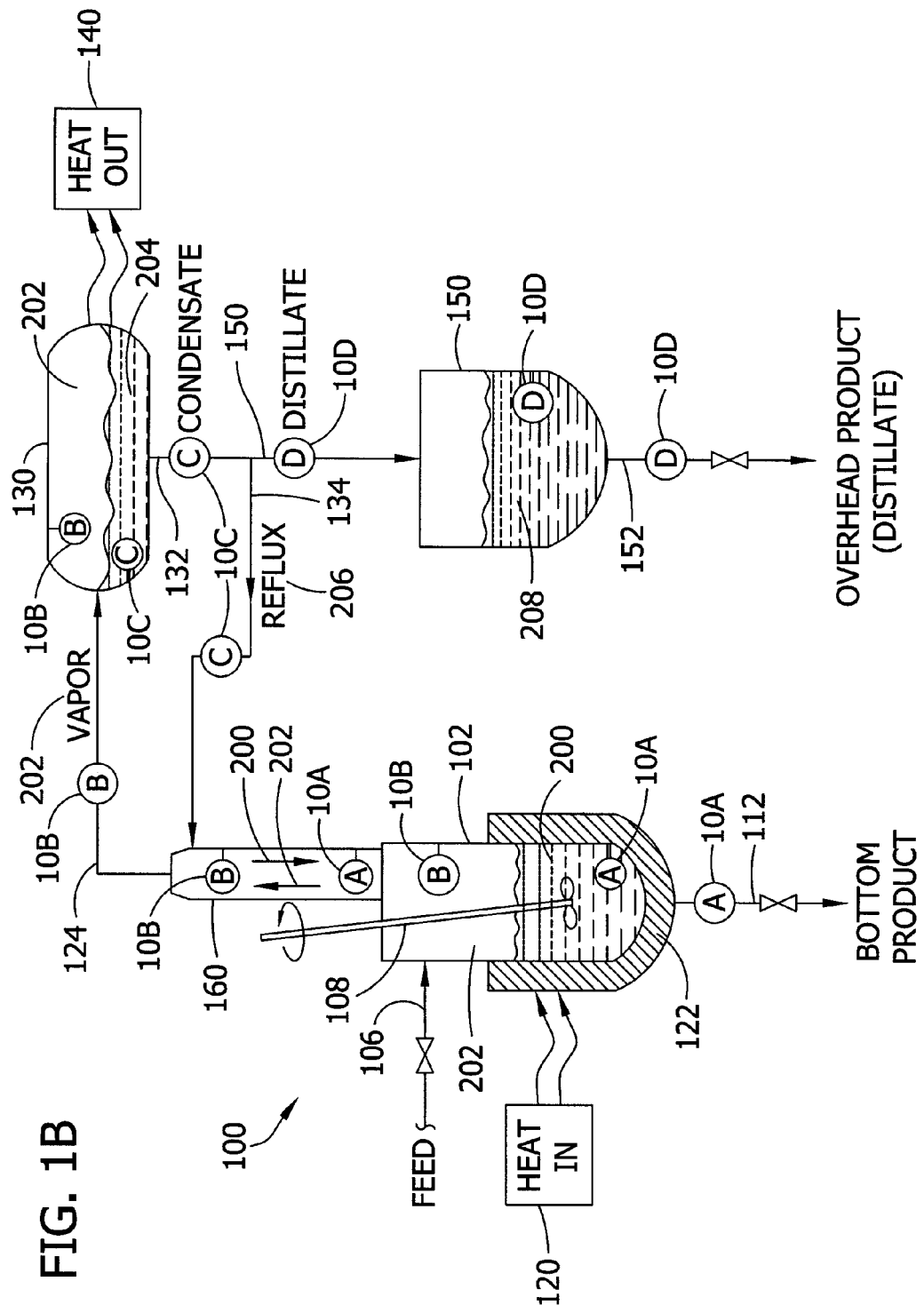

The invention is described in further detail below with reference to the figures, in which like items are numbered the same in the several figures.

DETAILED DESCRIPTION OF THE INVENTION

The following paragraphs describe certain features and combinations of features that can be used in connection with each of the various methods, sensors and systems of the invention, as generally described above. Also, particular features described hereinafter can be used in combination with other described features in each of the various possible combinations and permutations. As such, the invention is not limited to the specifically described embodiments.

General Overview—Methods

In practice of the method of the invention, the feed mixture to the process is typically a fluid mixture comprising a plurality of fluid components, and the process operates to separate components of the mixture by a change in state in the fluid feed mixture, or by mass transfer of a component of the feed mixture to another fluid, e.g., in unit operations such as distillation, liquid/liquid extraction or partial condensation. In distillation, the feed mixture ordinarily comprises a liquid phase mixture comprising a plurality of liquid components, but may also include or consist of a vapor phase mixture comprising a plurality of vapor components. Where the feed mixture comprises a liquid mixture, a portion of the mixture is vaporized to produce a primary vapor fraction and a residual liquid fraction. In monitoring and/or controlling the process, the sensing surface of a mechanical resonator is contacted with the primary vapor fraction, a distillate fraction condensed from or in equilibrium with the primary vapor fraction, the residual liquid fraction, or a secondary vapor flashed from or in equilibrium with the residual liquid fraction.

Where it is subjected to fractional distillation, the feed mixture may be introduced into a distillation column having a plurality of vapor-liquid equilibrium stages. The column may comprise a rectification zone comprising a plurality of rectification stages, a stripping zone comprising a plurality of stripping stages, or both a rectification zone and a stripping zone. The feed mixture is typically liquid, but may alternatively be vapor or a liquid/vapor mixture. Where the column comprises a rectification zone, the feed mixture is introduced into the column in a feed stage that is below the rectification zone, a liquid reflux stream is recycled to the rectification zone from an overhead vapor condenser to provide a liquid phase that flows downwardly through the rectification zone countercurrently to upwardly flowing vapor, and the primary vapor fraction comprises the vapor phase in the top stage of the rectification zone or a stage intermediate the feed stage and the top stage. Where the column comprises a stripping zone, the feed mixture is introduced into a feed stage above the stripping zone, a reboiler revaporizes a fraction of the liquid from the bottom stage to generate a vapor phase that flows upwardly through the stripping zone countercurrently to downwardly flowing liquid, and the residual liquid comprises the liquid in the bottom stage or a stage intermediate the feed stage and the bottom stage. In industrial chemical manufacturing operations, for example, or especially in petroleum refining, one or more side cuts may be taken from the rectification zone and or the stripping zone.

The vapor phase at the rectification stage from which each, any and/or all of these intermediate cuts are drawn may be deemed a "primary vapor fraction" for purposes of practicing the method of the invention. If a vapor phase is withdrawn from a rectification stage as a primary vapor fraction, either this vapor or a distillate fraction condensed from it may typically be contacted with the sensing surface of the resonator. Alternatively, a distillate liquid in equilibrium with a primary vapor fraction may be withdrawn from a rectification stage. Any of these fluids may be contacted with the sensing surface of a mechanical resonator for purposes of monitoring the process. In some instances, a sensor may be used to monitor a vapor fraction produced by flashing a distillate condensed from or in equilibrium with the primary vapor fraction, e.g., by flashing the overhead condensate from the column or by flashing a liquid withdrawn from a rectification tray. A vapor phase produced in this manner is also deemed a "primary vapor fraction" for purposes of the practice of the method.

Similarly, the liquid phase at the stripping stage from which each, any intermediate cut is drawn may be deemed a "residual liquid fraction" for purposes of the invention. If a liquid phase is withdrawn from a stripping stage as a residual liquid fraction, either this liquid or a secondary vapor flashed from it may typically be contacted with the sensing surface of the resonator. Alternatively, a secondary vapor comprising boilup vapor in equilibrium with a residual liquid fraction may be withdrawn from a stripping stage. Any of these fluids may be contacted with the sensing surface of a mechanical resonator for purposes of monitoring the distillation process. In some instances, the sensor may be used to monitor a liquid fraction produced by condensing a secondary vapor flashed from or in equilibrium with the residual liquid fraction, e.g., by condensing a fraction flashed from the column bottom fraction or by condensing a secondary vapor withdrawn from a stripping tray. A condensate produced in this manner is also deemed a "residual liquid fraction" for purposes of the practice of the method of the invention.

Where the feed mixture comprises a vapor phase mixture, a separation may be effected by partial condensation, or by introduction of the feed mixture into a distillation column. Where the process comprises partial condensation, a primary condensate and a residual vapor fraction are produced. The sensing surface may be contacted with the primary condensate, the residual vapor fraction, a secondary vapor fraction flashed from or in equilibrium with the primary condensate, or a secondary liquid fraction condensed from or in equilibrium with the residual vapor fraction. Where the process comprises rectification of the vapor phase exiting the partial condenser or stripping of the liquid condensate, the operation devolves to distillation as described above.

In the context of the instant disclosure, it will be understood that "separation" encompasses separation of a feed mixture into a plurality of fractions of differing composition, e.g., in the case of distillation, an overheads fraction or stream relatively enriched in a more volatile component and a bottoms fraction or stream relatively enriched in a less volatile component.

The inventions are further directed, in one aspect, to a method monitoring and/or for controlling a unit operation that includes separating one or more components of a multi-component composition by distillation. The particular approach to the distillation operation and the particular configuration for the distillation system is not narrowly critical. Hence, the distillation operation can include for example batch distillation approaches/configurations, continuous distillation approaches/configurations and semi-continuous distillation approaches/configurations.

In a batch distillation, the properties of the fluid sensed by the mechanical resonator may be monitored either constantly or at discrete intervals in time as a function of time, and the end point of the distillation identified when the proper(ies) being monitored reach or are projected to reach a defined target or combination of target values. In continuous distillation, one or more process streams may be monitored to determine if the target composition or property of the monitored stream(s) is being met, with independent variables such as feed rate, boilup rate, reflux ratio, product cut, etc., being adjusted in response to establish and maintain desired values.

The distillation operation can be based on one or more separation principles, and can therefore include for example differential distillations, flash distillations, single-stage distillations, multi-stage distillations, etc. Generally, distillation operations can be described as separation of components of a multi-component composition that comprises one or more liquid components based on a difference in volatility of at least one of the one or more liquid components as compared to the multi-component composition or to other components thereof. Although specific approaches and/or configurations for various distillation operations are described herein, such approaches and/or configurations are considered exemplary, and not limiting with respect to the scope of the invention except to the extent certain requirements are expressly recited in the claims.

Generally, then, the method of the inventions can comprise monitoring and/or controlling a unit operation that includes separating, and preferably distilling a multicomponent composition comprising one or more liquid components. A multi-component composition comprising one or more liquid components is provided (e.g., contained in or flowing through a process container such as a process vessel or a process pipeline), and at least a portion of at least one liquid component of the multi-component composition is vaporized to form a vapor. The vapor is condensed to form a condensate. At least a portion of the condensate is recovered as a distillate.

Generally, the process of the distilling operation can be monitored and/or controlled using one or more sensors. In one first approach, the sensor includes a mechanical resonator. In this first approach a sensing surface of a mechanical resonator is contacted with a fluid involved with the distillation operation. The fluid can be, for example, one or more of the multi-component composition, the vapor, the condensate or the distillate. The fluid-contacted resonator is stimulated (actively or passively), and a response of the resonator (to the stimulation) is monitored. In another, second approach, the sensor can be, generally, an on-line sensor configured to monitor one or more of the vapor, the condensate or the distillate. In this second approach, at least one on-line sensor is other than a temperature sensor, pressure sensor or flow sensor.

Various aspects of the methods of the invention are described in more detail in the immediately following paragraphs and further in the subsequent detailed description with reference to various figures. Each of the various aspects as generally and as specifically described are contemplated to be combined in various permutations and combinations.

The multi-component composition, such as a solution or a dispersion, can be provided to a fluid system or can be provided within a fluid system (e.g., provided to or provided within a process vessel such as a tank or a still or a reboiler, etc., or provided to or provided within a process pipeline such as a feed pipe for a flash distillation system, etc.). For example, the multi-component composition can be provided to a fluid system by feeding the multi-component composition (continuously, intermittently, or batchwise) to the fluid system.

At least a portion of at least one liquid component of the one or more liquid components of the multi-component composition is vaporized to form a vapor. Typically, vaporization of the multi-component composition is effected by controlling one or more process conditions (e.g., temperature, pressure) of the multi-component composition. The multi-component composition can be heated, for example, in any suitable manner (e.g., using a heating jacket and/or heating coils) to raise the temperature of the multi-component composition. Likewise, alternatively or additionally, the pressure of the multi-component system (e.g., the vapor pressure in a headspace above the multicomponent composition) can be reduced, for example, in any suitable manner such as by drawing a full or partial vacuum. Phase diagrams representing pressure-temperature relationships for vaporizing liquid-components and multi-component compositions are well known in the art.

At least a portion of the resulting vapor can be condensed to form a condensate. Typically, the vapor (or a portion thereof) is fed to a process vessel for a condensation operation, where condensation of the vapor is effected by controlling one or more process conditions (e.g., temperature, pressure) of the vapor. The vapor can be cooled, for example, in a condenser, as is well known in the art. Likewise, alternatively or additionally, the pressure of the vapor (e.g., the vapor pressure in a condenser) can be increased, for example. Phase diagrams representing pressure-temperature relationships for condensing vapor-phase components are well known in the art.

At least a portion of the condensate is then recovered as a distillate. In some embodiments, as where all of the condensate is collected or discharged from the fluid system, the condensate itself is the distillate (and in this context, the terms are referring to the same fluid and are therefore interchangeable). In other embodiments, for example in embodiments involving a multi-stage vapor-liquid contacting column, a portion of the condensate is diverted as a reflux stream to provide rectification of column overheads and improve mass transfer efficiency and the remaining (non-diverted) portion of the condensate stream is then recovered as a distillate. Typically, reflux ratio, i.e., ratio of reflux to distillate may be increased to improve mass transfer efficiency and enhance the approach to equilibrium in the rectification zone, thereby improving the degree of separation, or decreased to increase column productivity. Generally, the distillate can be considered any or all portions of the condensate that are recovered from the fluid system (making the fluidic system an open system with respect to distillate transfer out of the system, as described further below).

As noted above, in a first approach, the process of the distilling operation as described herein can be monitored and/or controlled using a sensor that comprises a mechanical resonator. Generally, in this first approach a sensing surface of a mechanical resonator is contacted with a fluid involved with the distillation operation. The fluid-contacted resonator is stimulated (actively or passively), and a response of the resonator (to the stimulation) is monitored. In preferred embodiments of this first approach, the method is applied as a process monitoring method or as a process control method which, in either case, includes stimulating the fluid-contacted resonator and monitoring a response of the resonator at a first time. Thereafter, at a second time after the first time, the monitoring and/or control methods include one or more of vaporizing at least a portion of at least one liquid component of the composition to form a vapor, condensing the vapor to form a condensate, and recovering at least a portion of the condensate as a distillate at a second time. At a third time after the second time, the fluid-contacted resonator is again stimulated (actively or passively) and a response of the resonator thereto is monitored. In a batch system, such sequential monitoring of the fluid allows the operator to identify the end point of the process, and gauge the rate of approach to the end point during the progress of the batch process. In a continuous process, the resonator is monitored either repetitively, typically at periodic intervals, or continuously, to provide information to the operator regarding the stability of the process and the maintenance of or departure from target properties and compositions.

In further general description of this first approach, the method includes the use of at least one mechanical resonator having a sensing surface and configured within the fluid process system such that the sensing surface of the resonator can be in fluid contact with any one of the fluids involved with the distilling operation, including for example, any one or more of the multi-component composition, the vapor, the condensate and/or the distillate. In some embodiments of this first approach, more than one mechanical resonators can be employed, for example at different locations within the fluidic system.

Hence, for example, in embodiments of this first approach including two mechanical resonators, the method can comprise contacting a sensing surface of a first mechanical resonator with a first fluid, stimulating the first-fluid-contacted resonator, and monitoring a response of the first-fluid-contacted resonator thereto, and further, contacting a sensing surface of a second mechanical resonator with a second fluid (which second fluid can be the same or different from the first fluid), stimulating the second-fluid-contacted resonator, and monitoring a response of the second resonator thereto. In such embodiments, the first and second fluids can be, respectively for example: the multi-component composition and the vapor; the multi-component composition and the condensate; the multi-component composition and the distillate; the vapor and the condensate; the vapor and the distillate; and the condensate and the distillate.

Hence, for example, in additional embodiments of this first approach comprising three mechanical resonators, the method can comprise contacting a sensing surface of a first mechanical resonator with a first fluid, stimulating the first-fluid-contacted resonator, and monitoring a response of the first-fluid-contacted resonator thereto, additionally contacting a sensing surface of a second mechanical resonator with a second fluid (which second fluid can be the same or different from the first fluid), stimulating the second-fluid-contacted resonator, and monitoring a response of the second resonator thereto, and further contacting a sensing surface of a third mechanical resonator with a third fluid (which third fluid can be same or different from each of the first fluid and the second fluid), stimulating the third-fluid-contacted resonator, and monitoring a response of the third-fluid-contacted resonator thereto. In such embodiments including at least three mechanical resonators, the first fluid, the second fluid and the third fluid can be, respectively for example: the multi-component composition, the vapor and the condensate; the multi-component composition, the vapor and the distillate; the multi-component composition, the condensate and the distillate; and the vapor, the condensate and the distillate.

As another example, further embodiments of this first approach can comprise four mechanical resonators. Here, the method can comprise contacting a sensing surface of a first mechanical resonator with a first fluid, stimulating the first-fluid-contacted resonator, and monitoring a response of the first-fluid-contacted resonator thereto, additionally contacting a sensing surface of a second mechanical resonator with a second fluid (which second fluid can be the same or different from the first fluid), stimulating the second-fluid-contacted resonator, and monitoring a response of the second resonator thereto, further contacting a sensing surface of a third mechanical resonator with a third fluid (which third fluid can be same or different from each of the first fluid and the second fluid), stimulating the third-fluid-contacted resonator, and monitoring a response of the third-fluid-contacted resonator thereto, and still further contacting a sensing surface of a fourth mechanical resonator with a fourth fluid (which fourth fluid can be same or different from each of the first fluid, the second fluid and the third fluid), stimulating the fourth-fluid-contacted resonator, and monitoring a response of the fourth-fluid-contacted resonator thereto. In such embodiments including at least four mechanical resonators, the first fluid, the second fluid, the third fluid and the fourth fluid can be, respectively for example: the multi-component composition, the vapor, the condensate and the distillate.

In further general description of this first approach, the response of the mechanical resonator can be correlated to one or more properties of the fluid being sensed. In particularly preferred embodiments for this approach, therefore, the method can further comprise determining one or more fluid properties of the fluid(s) (e.g., the multi-component composition, the vapor, the condensate and/or the distillate) based on the monitored response of the mechanical resonator(s). Preferably, the one or more properties can be selected from among the group consisting of viscosity, density, dielectric, conductivity and combinations thereof. Density is a particularly preferred property.

In another, second approach (as noted above), the sensor can be, generally, an online sensor configured to monitor (e.g., including to sense and/or evaluate one or more properties of) one or more of the vapor, the condensate and/or the distillate. In this second approach, the on-line sensor preferably comprises at least one on-line sensor that is a sensor other than a temperature sensor, a pressure sensor and a flow sensor. Preferably, the at least one on-line sensor is adapted and configured for measuring fluid-composition-dependent properties of the vapor, the condensate and/or the distillate, and preferably is adapted and configured in particular for measuring fluid properties other than temperature, pressure and flow rate (which for purposes of most commercial applications involving distillation, are generally fluid-composition-independent properties). Exemplary on-line sensors include for example, mechanical resonator sensors, optical sensors, electrical sensors, density sensors, viscosity sensors, etc. Particularly preferred on-line sensors include, for example, mechanical resonator sensors such as flexural resonator sensors or torsional resonator sensors, as well as refractive index sensors.

Preferably, in this second approach, the vapor, condensate or distillate are monitored using the on-line sensor to determine one or more properties of the vapor, the condensate or the distillate, where the one or more properties are selected from among the group consisting of viscosity, density, an electrical property, an optical property and combinations thereof. More preferably, the one or more properties can be selected from among the group consisting of viscosity, density, dielectric and combinations thereof. Alternatively, the one or more properties are one or more electrical properties selected from the group consisting of dielectric, conductivity and combinations thereof. Alternatively, the one or more properties are one or more optical properties. With respect to optical properties, the monitoring step can comprise irradiating a portion of the fluid being sensed (e.g., the vapor, the condensate or the distillate) with electromagnetic radiation and observing a response resulting from allowing the electromagnetic radiation to interact with the fluid being sensed. Typically, the observed response can include a response selected from the group consisting of absorbance, reflectance, scattering, refraction and combinations thereof. In a preferred embodiment involving optical properties, the one or more properties include refractive index.

In further general description of this second approach to the methods of the invention, the particular configuration of the on-line sensor is not narrowly critical. Preferably, the on-line sensor effects a fluid sensing operation locally to the fluid system without laborious and inefficient human-effected sampling and without off-system analysis (e.g., via shipment or carrying to an off-site analytical laboratory). Preferably, the on-line sensor senses the fluid in a sensing operation with at least some response of the sensor being sensed and preferably processed in near real time. The particular response time is not narrowly critical, but is preferably sufficiently fast to provide meaningful process monitoring and/or process control for the distillation operation at interest. Without being limited except to the extent expressly set forth in the claims, the response time of the on-line sensor is preferably not more than around 10 minutes, preferably not more than around 5 minutes, more preferably not more than around 2 minutes and most preferably not more than around one minute. In some embodiments, even faster response times are possible, and can be advantageous, including for example response times of not more than about 40 seconds or not more than about 30 seconds or not more than about 20 seconds or not more than about 10 seconds.

The inventions are generally directed, in another second aspect, to a method for monitoring and/or for controlling a reaction, especially where the reaction is conducted in a fluid medium, i.e., a gas or vapor phase, a liquid phase, or a mixed liquid and gas or vapor phase. For example, where the medium comprises a liquid phase, the sensing surface of the resonator may be contacted with the medium itself, a solution comprising a reactant and/or product of the reaction in the reaction medium, a dispersion comprising a reactant and/or product of the reaction in the reaction medium, a vapor phase evaporated from the medium, another liquid phase resulting from a phase separation during the course of the reaction, or a dispersion comprising another liquid phase. Where the reaction is conducted in the gas phase, the sensing surface of the resonator may be contacted with a fluid selected from the group consisting of the reactant gas, a diluent gas, a gaseous feed mixture, a reaction product gas, a feed mixture comprising a condensed phase dispersed in a gaseous medium, a product mixture comprising a condensed phase dispersed in a gaseous medium, and a liquid phase condensed from the gas phase. In this aspect, a multi-component composition may be provided in a process vessel. The multi-component composition is a solution or a dispersion comprising one or more liquid components and at least one non-polymeric organic component dissolved or dispersed in the one or more liquid components. The at least one non-polymeric organic component is formed or reacted in the process vessel under reaction conditions. The progress of the reaction in the process vessel can be monitored and/or controlled by a method that includes (i) contacting a sensing surface of a mechanical resonator with the multi-component composition at a first time during the reaction, stimulating the composition-contacted resonator at the first time, and monitoring a response of the resonator associated with the first time, and thereafter (ii) contacting a sensing surface of the mechanical resonator with the multi-component composition at a second time during the reaction, stimulating the composition-contacted resonator at the second time, and monitoring a response of the resonator associated with the second time. In a continuous reactor, one or more process fluids may be contacted with different sensors, at the same or different times, at different points along the flow path of the reaction system.

The type of reaction in this second aspect of the invention is not narrowly critical. It can include, for example, reactions such as a crystallization reaction or a precipitation reaction. It can also include, for example, reactions involving the making and breaking of covalent bonds such as oxidations, reductions, hydrogenations, carboxylations, etc. In some reactions, the non-polymeric organic component can be a first reactant and the reaction can be effected by a method that includes providing a second reactant. The second reactant can be a gaseous, liquid or solid component. The non-polymeric organic component can be allowed to react with the second reactant to form a reaction product. The mechanical resonator sensor can be used to monitor one or more of the first reactant, the second reactant, the reaction product or the reaction mixture composition.

The inventions are generally directed, in another third aspect, to a method for monitoring and/or controlling a reaction mixture or components thereof. In this method, one or more liquid components are provided in a process vessel, and at least one non-polymeric organic component in provided in the process vessel. The at least one non-polymeric organic component is dissolved or dispersed in the one or more liquid components to form a solution or dispersion, respectively. Optionally, additional reactants can be provided to the process vessel to form a reaction mixture. One or more of the fluids provided to the process vessel or contained within the process vessel are monitored using a mechanical resonator sensor. The monitored fluids can be selected from the one or more liquid components, the at least one non-polymeric organic component, the solution or dispersion, the reaction mixture, and combinations thereof. The fluid is monitored by a method that includes contacting a sensing surface of a mechanical resonator with the fluid, stimulating the fluid-contacted resonator, and monitoring a response of the resonator.

In some embodiments for this third aspect of the invention, the fluid is monitored to determine the purity of the fluid. For example, the fluid can be a solvent, and the solvent can be monitored to determine the purity thereof. As another example, the fluid can be a solvent, and the solvent can be monitored to determine an amount of water in the solvent.

In any embodiment within the first aspect of the invention (including both the first approach or the second approach thereof), or within the second aspect of the invention or within the third aspect of the inventions, each relating to various methods of the invention, the particular nature of the multi-component composition is not critical. Generally, the multi-component composition can comprise a multi-component solution or a multi-component dispersion, in each case comprising one or more liquid phase media. For example, the multi-component composition can be a solution comprising at least one solute dissolved in one or more liquid solvents. The multi-component composition can alternatively or additionally be a solution comprising two or more liquid solvents, such as two or more miscible liquid solvents (with or without dissolved solute). The multi-component composition can also be dispersion comprising a (first, internal) dispersed phase within a (second, external) continuous phase. The dispersed phase can comprise at least one component selected from a solid component, a semi-solid component and/or a liquid component as well as combinations thereof. The continuous phase comprises one or more liquid components. Hence the dispersion can be a solid-liquid dispersion, a semisolid-liquid dispersion, or a liquid-liquid dispersion. The dispersion can be a suspension, such as a colloidal suspension or other colloidal system. The dispersion can be a uniform dispersion comprising a substantially uniformly dispersed first internal phase within the continuous second external phase. The dispersion can alternatively be a non-uniform dispersion comprising a non-uniformly dispersed first internal phase within the continuous second external phase. The dispersion can be created in-situ within the fluid system, for example, as the result of a precipitation reaction, or as the result of a crystallization reaction, in each case within the multi-component composition.

Also, in any embodiment within the first aspect of the invention (including within the first approach or second approach thereof), or within the second aspect of the invention or within the third aspect of the inventions, each relating to various methods of the invention, the mechanical resonator is preferably a flexural resonator or a torsional resonator. Generally, the one or more flexural resonators or torsional resonators can comprise a flexural resonator sensing element or a torsional sensing element, respectively, in each case having a sensing surface for contacting the fluid being sensed. In operation during a sensing period, the sensing surface of a flexural resonator displaces or is displaced by at least a portion of the fluid being sensed. Preferred flexural resonators include tuning fork resonators, cantilever resonators, unimorph resonators and bimorph resonators. Tuning fork resonators are particularly preferred. The flexural resonator sensor and/or torsional resonator sensor can be operated passively or actively, and if actively operated, is preferably excited using a stimulus signal. The particular nature of the stimulus signal is not critical, but in some embodiments, the stimulus signal can be a waveform having a frequency (e.g., a predetermined frequency) or having a range of frequencies (e.g., being swept over a determined or predetermined range of frequencies), and in each such case, having a frequency or a range of frequencies of less than about 1 MHz. In some embodiments, additional sensors (e.g., such as temperature and/or pressure sensors and/or flow sensors) can be employed in the systems and methods in combination with the one or more mechanical resonators (preferably, flexural resonators). For example, in one preferred embodiment, the mechanical resonator is configured in a sensor, and the sensor further comprises a temperature sensing element having a sensing surface proximate to a sensing surface of the mechanical resonator.

In particularly preferred applications, the methods of the invention (including the various methods and embodiments described in connection with the various aspects and/or approaches of the invention as delineated above and expounded further upon below) can be applied for process monitoring and/or for process control for specific unit operations involving distillation. In particular, for example, the various methods and embodiments can be applied for process monitoring and/or for process control for unit operations such as liquid-component-switching operations (e.g., solvent switching operations) and/or such as concentration operations.

In such operations, a second solvent may be introduced into a feed mixture comprising a feed solution comprising a first solvent and a solute. This produces a mixed solvent solution comprising the first solvent, the second solvent and the solute. A portion of the mixed solvent solution is vaporized under conditions of temperature and pressure at which the volatility of the second solvent is lower than the volatility of the first solvent, to provide a primary vapor fraction enriched in the first solvent relative to the mixed solution and a residual liquid phase enriched in the second solvent relative to the mixed solution. In monitoring the process, the sensing surface of a mechanical resonator is contacted with any of various process fluids including, e.g., the primary vapor fraction, a distillate fraction condensed from or in equilibrium with the primary vapor fraction (such as at the outlet of a condenser in fluid communication with the still pot), the residual liquid fraction, and a secondary vapor fraction flashed from or in equilibrium with the residual liquid fraction. The terms "primary vapor fraction," distillate fraction and "residual liquid fraction," and secondary vapor (or "boilup" fraction encompass the various derivatives thereof as described hereinabove, e.g., intermediate cuts that might be taken from a rectification zone above the feed point to the batch still.

Specifically, the methods of the invention (including those of the first, second and third aspects) can be applied for process monitoring and/or process control of a liquid-component-switching operations of various nature, including for example: liquid-component switching operations executed as continuous, semi-continuous or batch operations; liquid-component switching operations executed as constant volume liquid-component switching operations. For example, a liquid-component-switching operation can comprises providing the multi-component composition in a vessel, where the multicomponent composition comprises a first liquid component having a first vapor pressure. The first liquid component can be separated from the multi-component composition by a method that includes vaporizing the first liquid component of the composition to form a first (primary) vapor, condensing the first vapor to form a first condensate, and recovering at least a portion of the first condensate as a first distillate, and that also includes feeding a second liquid component to the vessel, where the second liquid component has a second vapor pressure lower than the first vapor pressure. The separating step and the feeding step can be continued until the multi-component composition comprises the second liquid component and at most a residual amount of the first liquid component. If desired, the second-liquid component can be fed continuously or intermittently to an evaporation zone within a vessel at a volumetric flow rate substantially the same as the volumetric flow rate at which the first distillate is recovered, whereby the volume of the multi-component composition in the vessel is substantially constant during the liquid-component-switching operation. Preferably, the amount of residual first liquid component is not more than about 10% (by weight or by volume at the end point of the distillation), more preferably not more than about 5% (by weight or by volume), still more preferably not more than about 2% (by weight or by volume). Even more stringent separations applied to liquid-component switching operations can be monitored and controlled by the methods of the invention, with the amount of residual first liquid component being not more than about 1% (by weight or by volume), more preferably not more than about 0.5% (by weight or by volume), still more preferably not more than about 0.2% (by weight or by volume), and in some embodiments preferably not more than about 0.1% (by weight or by volume).

In another specific example, the methods of the invention (including those of the first approach and the second approach) can be applied for process monitoring and/or process control of concentration operations of various nature, including for example: concentration operations executed as continuous, semi-continuous or batch operations. In such processes a feed mixture may typically comprise a liquid phase mixture comprising a liquid solvent and a solute dissolved in the solvent. In applications involving evaporation, a portion of the solvent is vaporized from the feed mixture to produce a vapor phase comprising the solvent and a residual liquid phase having an increased concentration of the solute in the solvent. A sensing surface of a mechanical resonator is contacted with the vapor phase, a condensate condensed from the vapor phase, the residual liquid, or a fluid dispersion comprising the residual liquid phase. Such dispersion may typically comprise particulate precipitated solute dispersed in the residual liquid, e.g., in concentration of a cell liquor obtained from a chloralkali cell to 50 wt. % alkali metal hydroxide and to precipitate salt.

Evaporation of solvent may be accompanied by crystallization of a desired product from the solution to yield the crystallized product slurried in a mother liquor comprising the solvent. The mother liquor ordinarily contains residual solute at its saturation concentration, and often other solutes which remain in solution during the crystallization.

Crystallization of a solute from a solution may also be accomplished by cooling of the solution, with or without evaporation of solvent. Irrespective of whether evaporation is involved, the method may comprise contacting the sensing surface of the mechanical resonator with the slurry of crystalline precipitate in mother liquor and/or with a mother liquor filtrate or centrate obtained after separation of the mother liquor from the crystallized solute by filtration or centrifugation. In evaporation operations, the sensor may also be contacted with the vapor phase produced in the evaporation, or with a condensate condensed from the vapor phase to monitor the condition of the vapor and/or entrainment of liquid phase in the vapor phase.

In one exemplary preferred embodiment involving a concentration operation, the multi-component composition can be a solution comprising at least one solute dissolved in one or more liquid solvents. The concentration operation can comprise providing the solution in a vessel, and separating at least one of the one or more liquid solvents from the solution by a method that includes vaporizing the at least one liquid solvent to form the vapor, condensing the vapor to form the condensate, and recovering at least a portion of the condensate as the distillate, thereby concentrating the solute in the solution in the vessel. In another preferred embodiment involving a concentration operation, the multi-component composition can be a dispersion, with the dispersed phase comprising at least one solid, semi-solid or liquid component, and the continuous phase comprising the one or more liquid components. In this instance, the concentration operation can comprise providing the dispersion in a vessel, and separating at least one of the one or more liquid components of the continuous phase from the dispersion by a method that includes vaporizing the at least one liquid component to form the vapor, condensing the vapor to form the condensate, and recovering at least a portion of the condensate as the distillate, thereby concentrating the dispersed phase of the dispersion in the continuous phase of the dispersion in the vessel. The separating step can be continued until the concentration of the dispersed phase is within a specified proximity to a desired endpoint concentration. For example, the concentration can be within about 10% of the desired concentration endpoint, more preferably within about 5%, still more preferably within about 2% of a desired concentration endpoint. Concentration operations of the invention can be even more rigorously monitored and/or controlled by the methods of the invention, including to be within about 1% of a desired endpoint, and more preferably within about 0.5%, still more preferably within about 0.2%, and in some embodiments within about 0.1% of a desired endpoint.

The resonator provides different forms of response in a crystallization process, and can be used for various purposes in either monitoring a commercial crystallization process, facilitating optimization studies of existing processes, or developing new, modified, or improved crystallization processes. For example, in one mode, the resonator can be used to detect the onset of crystallization, while in another mode, it may monitor the progress of crystallization. The resonator may also be used to monitor seed growth or seed bed establishment after seeding a crystallization batch.

With regard to the onset of crystallization, the resonator can sense if any solids are present, and thus detect the point at which precipitation is commenced. Generally, crystallization is initiated by seeding a supersaturated solution that has been prepared by concentrating a solution of the product to be crystallized, or by a chemical reaction in which the product to be crystallized is formed in progressively increasing concentration within a solvent medium. Seeding comprises introduced seed particles, ordinarily crystals of the product to be crystallized into the crystallization medium, which typically comprises a supersaturated solution of the product. Seeding can be effective to initiate crystallization and/or to promote or modulate the crystallization process, e.g., to reduce the number of nucleation sites and enhance the particle size of the crystalline product. In some applications, seeding allows crystallization to be manipulated to control crystal morphology. More particularly, in the pharmaceutical industry crystallization may be controlled to produce a particular desired polymorph of a pharmaceutical product. In such operations, it is generally desirable to seed only to a dilute seed content. As a result, if conditions are not right (e.g., if supersaturation has not in fact been realized), the seed may dissolve rather than initiate precipitation. In such case, spontaneous precipitation may ultimately ensue when the concentration exceeds the metastable range, yielding a product of undesired morphology, and/or particle size, that be unuseable and even difficult to salvage. Without effective seeding, crystallization may not occur until the maximum metastable concentration has been exceeded, at which point massive nucleation and formation of an exceptionally fine precipitate may result, typically of the wrong polymorph. The product in this case may not only be unsalvageable, it may not even be filterable.

However, a mechanical resonator can sense the relatively low concentration of solid particles resulting from seeding. The absence of such signal may verify that the seed crystals have not dissolved, at least not fully, or instead may indicate that the seed has dissolved, thus alerting the operator to the need to add additional seed material or to change process conditions such as temperature to establish a supersaturated solution. Where additional seed material can be added before the maximum metastable concentration has been exceeded, controlled precipitation can still be realized, and a crystalline product of desired morphology and particle size may be produced.

In addition to its value in detecting the onset of precipitation, whether for seeding or other process control purposes, a flexural resonator is useful in monitoring the progress of crystallization. As supersaturation is released, substantially massive precipitation occurs, even where crystallization is properly controlled, whether by seeding or otherwise. Thus, the initiation of crystallization appears as a discontinuity in the resonator response, typically the dielectric constant response, as a function of time. As crystallization proceeds subsequent to initial precipitation, the dielectric constant typically undergoes progressive change along a continuous curve as a function of a change in mass resulting from buildup of crystalline product on the resonator. From this response, the pace and pattern of crystal growth can be followed. Crystal growth may be promoted by cooling and/or introduction of an anti-solvent, and the effect of these manipulations can also be monitored using a resonator. As discussed below in connection with monitoring of chemical reactions, a mechanical resonator generally provides a superior real time response than more traditional analytical methods for following the course of crystallization, such as FTIR or near infrared or light scattering methods (i.e., FBRM from Lasontec, for example).

Thus, in operation of an industrial manufacturing process, a mechanical resonator may be used either to determine the crystallization end point, or to provide data and/or a signal for feedback control of the crystallization process, e.g., by calling for introduction of additional seed crystals, for controlling the rate of cooling, for controlling the temperature of a tempered cooling fluid, for controlling the feed rate of a feed solution to, and/or withdrawal of product slurry from, a continuous or semi-continuous crystallizer.

The use of a mechanical resonator can also be valuable in laboratory studies of crystallization. Because most crystallization processes proceed by release of supersaturation, it is important to know the metastable range of supersaturation so that the crystallization process may be appropriately controlled, e.g., to initiate seeding before the concentration exceeds the metastable limit. This limit is generally a function of temperature. Points on a maximum metastable concentration vs. temperature curve can be determined in the following manner: (i) formulating a solution of known concentration by heating a known quantity of solid product in the presence of a known but limited quantity of solvent; then (ii) cooling the resulting solution gradually until spontaneous crystallization occurs, as detected by a discontinuity in the dielectric constant response as a function of temperature during cooling. The concentration of the solution as initially formulated can then be identified as the maximum metastable supersaturated solution strength at the temperature of crystallization, while analysis of the mother liquor provides the saturation concentration. By repeating this process over a range of formulations of varying initial concentration, the metastable range can be plotted as a function of temperature.

In the latter application, the mechanical resonator offers an alternative to the so-called FBRM method for determining metastable supersaturation limits. FBRM is a laser light scattering technique offered by Lasontec which provides information not only on the wt. % of the solution at the metastable limit, but also provides data on the particle size distribution of the crystalline product in the crystallization slurry. However, the data provided by FBRM is inaccurate if the crystalline product is not spherical, which it typically is not and can have a limit of detection for the presence of solids sub-par to that of a flexural resonator.

As noted above, all of the various methods and embodiments of the invention can be applied for process control of unit operations involving distillation. Generally, in such applications, the methods of the invention can further comprise controlling one or more parameters of the unit operation based at least in part on the monitored response of the sensor (such as the response of the resonator for mechanical resonator sensors, or such as the response of the on-line sensor, said response being generally characterized by a sensor output (e.g., an output signal) of the on-line sensor. The particular parameters being controlled are not critical, but can include for example one or more of: (a) temperature of fluid in a process vessel containing the multi-component composition, the condensate or the distillate; (b) pressure in a head space above fluid in a process vessel containing the multi-component composition, the condensate or the distillate; (c) feed rate of the multi-component composition to a process vessel; (d) feed rate of a liquid-component being fed to a process vessel containing the multi-component composition; (e) reflux rate of the condensate; (f) level of fluid in a process vessel containing the multi-component composition, the condensate, or the distillate; and (g) combinations thereof.

The method of the invention may also be applied to extraction operations. For example, mechanical sensors may be used in a liquid/liquid extraction process wherein the feed mixture comprises a liquid mixture which is contacted with another liquid that is immiscible with the feed mixture but comprises a solvent for a component of the feed mixture, thereby causing transfer of that component from the feed mixture. As a result of the transfer, an extract is produced comprising the extraction solvent and the transferred component. Transfer of the solute component alters the composition of the liquid feed mixture to produce a raffinate having a reduced concentration of the transferred component. In monitoring the process, a sensing surface of a mechanical resonator may be contacted with a fluid selected from among the extract, the raffinate, the feed mixture and combinations thereof.

The method of the invention is particularly applicable to an extraction process comprising a plurality of liquid-liquid contacting stages. A feed mixture comprising a solute dissolved in a first solvent, is introduced into the feed stage of an extraction system for conducting such a process. For example, such a feed mixture may be introduced into a countercurrent extraction system wherein a first liquid phase comprising the first solvent in a proportion exceeding that of the second (extraction) solvent is passed through the plurality of stages in series, and a second liquid phase immiscible with the first liquid phase and comprising the second solvent in a proportion exceeding the proportion of the first solvent therein is passed through the plurality of stages countercurrently to the first phase. As the two liquid phases flow through the series of stages, the second phase becomes progressively enriched in the solute and the first phase becomes progressively depleted in the solute. An extract comprising the second liquid phase is withdrawn from any of said series of stages, and a raffinate comprising the first liquid phase may also be withdrawn from any of the stages. In a simple countercurrent extraction system, the extract is withdrawn from the feed stage for the feed mixture and the raffinate is withdrawn from the last of the series of stages with respect to the direction of flow of the first liquid phase, i.e., the feed stage for the extraction solvent. However, if desired, intermediate extracts, or intermediate raffinates, may be withdrawn much in the manner described above with respect to distillation. Moreover, the method of the invention may also be implemented in a co-current flow extraction process, or in a cross-flow extraction process wherein, e.g., fresh solvent is introduced and an extract and/or raffinate withdrawn at a plurality of stages in an otherwise countercurrent or co-current extraction system.

In monitoring or controlling a multi-stage countercurrent, co-current or cross-flow liquid/liquid extraction system, a variety of intermediate streams may be sensed with a mechanical resonator, in addition to various relatively enriched or depleted fractions which may be withdrawn from the system.

The method of the invention may further be applied in monitoring and control of a process wherein the feed mixture comprises a solid phase component and another condensed phase component, either solid or liquid, which is subject to removal in a fluid phase from the solid phase component. In such method, a vapor comprising the another component is transferred from the feed mixture to form a gaseous phase comprising the vapor, and the mechanical sensor may be contacted with the gaseous phase comprising the vapor or a condensate condensed from the gaseous phase. For example, the method may be applied to a drying process wherein a wet solid is heated and/or exposed to a vacuum in a drying zone, with or without contacting the wet solid with a flow of a carrier gas (stripping gas) to promote mass transfer of water vapor or the vapor of another volatilizable liquid from the feed mixture to the gaseous phase in the drying zone. Ordinarily a non-condensable gas such as air, nitrogen, carbon dioxide or mixtures thereof is used as the stripping gas, so that the gaseous effluent and/or the gas phase within the drying zone comprises such non-condensable component. Even where no stripping gas is purposefully introduced, the vapor stream typically may contain residual non-condensable gases initially present in the dryer apparatus or feed material, or admitted via leakage in pipe gaskets, shaft seals, etc. The sensing surface of the mechanical resonator may be contacted with the gas phase in the drying zone, the gaseous effluent, a condensate condensed from the gaseous phase in the drying zone, or the gaseous effluent. Whether or not the process is characterized as drying, the method can be applied to a process in which a sublimable solid is stripped from a mixture comprising another relatively non-volatile solid component under the influence of heat, vacuum, and/or flow of a stripping gas. In such a process, a vapor generated from the another condensed phase component is transferred from the mixture to form a gaseous phase comprising the vapor, and the sensing surface of the mechanical resonator is contacted with such gaseous phase or a condensate condensed from the gaseous phase.

The method is also applicable to an extraction process wherein the feed mixture comprises a solid component and another condensed phase component, either solid or liquid, that is subject to being transferred to a liquid extraction solvent with which the feed mixture is contacted. For example, the method can be used in monitoring and/or controlling a process wherein oils are extracted from oil seeds such as linseed oil from cotton seeds or soy oil from soybeans using hydrocarbon or other organic liquid extractants. In such instance, the solid phase mixture is contacted with the liquid solvent, and the another condensed phase component is transferred to the liquid phase to produce an extract. The sensing surface of the mechanical resonator may be contacted with the extract. In some instances, the extract may be subject to further processing, e.g., by distillation, and a mechanical resonator contacted with a primary vapor, distillate condensed from or in equilibrium with the primary vapor, residual liquid, or secondary vapor flashed from or in equilibrium with the residual liquid produced in the distillation.

The method of the invention may also be applied to sorption operations such as, for example, the absorption of a component of a gas into a liquid absorbent solution, the adsorption of a component of a gas or liquid onto an adsorbent such as activated carbon or a molecular sieve, or chromatographic separations conducted on either an analytical or production scale, thereby producing a fluid fraction depleted in the sorbed component. In adsorption processes such as chromatographic separation, a sorbent loaded with a sorbed component may be contacted with an eluant for desorption of the component, yielding an eluate in which the sorbed component may be enriched or isolated. In absorption processes, the process produces an absorption solution enriched in the sorbed component. In some operations, the enriched sorption solution may be subject to distillation for further enrichment, isolation or refining of the sorbed component; in other operations, the sorbed component by be separated, isolated and/or refined by other unit operations such as liquid/liquid liquid extraction, thus yielding an extract containing that component. The extract in turn may be subject to further unit operations such as distillation, evaporation, etc.

In monitoring the sorption process, a flexural mechanical resonator is contacted with a fluid representative of the extent or effectiveness of the sorption such as a depleted fluid fraction, a fluid sorbent, an absorption solution enriched in the sorbed component, an eluant for removing sorbent from a solid sorbent, an eluate comprising said component desorbed from said sorbent and combinations thereof. A representative fluid may also include an extract of the enriched sorption solution, a distillate or bottoms stream obtained by distillation of the enriched sorption solution or extract thereof, or a concentrate or slurry produced by evaporation and/or crystallization of an enriched sorption solution or eluate.

In one particular application, a hygroscopic organic solvent such as, e.g., tetrahydrofuran, is contacted with a molecular sieve from removal of residual moisture therefrom. Effectiveness of the separation and control of the adsorption process may be monitored by contacting a flexural mechanical resonator with feed mixture comprising the wet solvent and/or with an effluent stream comprising the dessicated solvent. The response of the resonator, e.g., the dielectric constant response, is sensitive to the water content of the liquid fraction, thus indicating the extent to which moisture has been removed from the solvent.

However, the process is more generally applicable to a process comprising monitoring the water content of a hygroscopic liquid. For example, a flexural resonator may be contacted with such a liquid to monitor moisture content in storage, shipping, or pipeline transfer. It may also be used to monitor the moisture content of feed mixtures, reagents, product liquids, by-product liquids, and various other process liquids and condensates introduced into, produced by or otherwise used in connection with chemical reaction, distillation, evaporation, drying, extraction, etc. For example, the resonator may be used to monitor moisture content in a reaction medium where water is a product of reaction, or to monitor utility leaks, e.g., leakage of steam or cooling water into a reaction or crystallization mass from an internal coil immersed therein, or between tube(s) and shell of a heat exchanger through which the reaction or crystallization mass is circulated. Moisture content of process streams can also be monitored in other unit operations, e.g., in the condensate from the overhead condenser of a distillation column, in the reheated bottom stream exiting a distillation reboiler, etc.

Generally, control of the controlled parameters can be effected using a feedback control system. Other control schema are also suitable. The control system can generally include, in addition to the sensor (e.g., mechanical resonator sensor or other sensor as described herein), a processor such as a microprocessor for processing the monitored response of the sensor to determine whether a control action is necessary, and one or more process control elements (e.g., valves, voltage regulators, etc.) for effecting any necessary control action, together with appropriate communication paths between the sensor, the processor and the one or more process control elements.

A number of more specific embodiments can be realized within the context of this approaches and embodiments described herein, some of which are described above within the Summary of the Invention, and others of which are described within and/or are readily ascertainable from the context of the Detailed Description of the instant specification (including combining the various features described therein in any and all possible combinations and permutations).

General Overview—Sensors And Systems

In another general fourth aspect, the invention is directed to sensors and to systems comprising a sensor.

Generally, the system comprises a fluid process configured for distillation, extraction, evaporation, drying, chemical reaction, or other unit operation, and one or more sensors configured in association with the fluid system such that the sensor can monitor a fluid within the fluid system. More particularly, the system may comprise an industrial manufacturing process for the prediction of chemicals or pharmaceuticals, petroleum refining, hydrometallurgy, or extraction and refining of natural organic materials such as sugars, starches, proteins, alkaloids, gums, resins, etc.

In various preferred applications, the method of the invention is implemented in a fluid process comprising distillation. In those applications, the fluid system can comprise (i) a process container for providing a multi-component composition comprising one or more liquid components, (ii) a heat source associated with the process container and adapted for vaporizing at least a portion of at least one liquid component of the composition to form a vapor, (iii) a condenser in fluid communication with the process container for receiving the vapor, (iv) a heat sink associated with the condenser for condensing the vapor to form a condensate, and (v) a distillate receiver for recovering at least a portion of the condensate as a distillate.

In a first approach with respect to this aspect of the invention, system can comprise a mechanical resonator sensor comprising a mechanical resonator. The mechanical resonator sensor can be configured in association with the fluidic system such that a sensing surface of the mechanical resonator can contact a fluid within the fluid system (e.g., the fluid being any of the multi-component composition, the vapor, the condensate or the distillate). The mechanical resonator sensor can further comprise one or more electrical circuits in signaling communication with the mechanical resonator. The one or more electrical circuits may comprise signal processing circuitry or data retrieval circuitry or combinations thereof. Further details about the components of the mechanical resonator sensor, including specifics relating to the mechanical resonator and/or the electrical circuit and/or the signaling communication paths is described below, each of which variously described features can be used in combination with the first approach for a system of the invention.

In further description of this first approach of this aspect of the invention, the system can comprise two or more mechanical resonator sensors. For example, the system can comprise a first sensor comprising a first mechanical resonator, the first sensor being configured in association with the fluid system such that a sensing surface of the first mechanical resonator can contact a first fluid within the fluid system, as generally described above. The system can further comprise a second sensor comprising a second mechanical resonator, the second sensor being configured in association with the fluid system such that a sensing surface of the second mechanical resonator can contact a second fluid within the fluid system (the second fluid being the same or different from the first fluid, including the multi-component composition, the vapor, the condensate or the distillate). The second sensor further comprises an electrical circuit in signaling communication with the second mechanical resonator, the electrical circuit comprising signal processing circuitry or data retrieval circuitry or combinations thereof.

In further description of this first approach of this aspect of the invention, the system can comprise three or more mechanical resonator sensors, or in some embodiments, four or more mechanical resonators. Reference in this regard is made to the parallel discussion with respect to the methods of the invention (above and further detailed below), which is equally understood to be applicable in connection with the systems of the invention.

In another, second approach to this aspect of the invention, the system can comprise an on-line sensor (other than a temperature sensor, a pressure sensor and a flow sensor), the on-line sensor being configured in association with the fluid system such that the sensor can monitor a fluid within the fluid system. The monitored fluid can be the vapor, the condensate or the distillate. Preferably, the on-line sensor is adapted for determining one or more fluid-composition-dependent properties of the vapor, the condensate or the distillate. For example, the on-line sensor can be a viscosity sensor, a density sensor, an electrical property sensor, an optical property sensor or combinations thereof. Preferably, the on-line sensor can be selected from the group consisting of a viscosity sensor, a density sensor, a dielectric sensor and combinations thereof. In some embodiments, the on-line sensor can be an electrical property sensor selected from the group consisting of a dielectric sensor, a conductivity sensor and combinations thereof. In other embodiments, the on-line sensor can be an optical property sensor. An optical property sensor can comprise a radiation source configurable for irradiating a portion of the fluid (i.e., the vapor, the condensate or the distillate) with electromagnetic radiation, and one or more components for observing a response of the interaction between the fluid and the electromagnetic radiation. Responses can include, for example, those selected from the group consisting of absorbance, reflectance, scattering, refraction and combinations thereof. In particularly preferred embodiments, an optical on-line sensor can be a refractive index sensor. The on-line sensor can also be a mechanical resonator sensor.

In both the first and second approaches to this aspect of the invention, including any embodiment included therewith, the system can be adapted for process control operations. In particular, the system can further comprise, in addition to the sensor, a processor for processing a monitored response of the sensor to determine whether a control action is necessary, one or more process control elements for effecting any necessary control action, and appropriate communication paths between the sensor, the processor and the one or more process control elements.

In any embodiment of the first and/or second approaches that include a mechanical resonator sensor, the sensor can comprise one or more mechanical resonators, preferably including at least one flexural resonator and/or one torsional resonator. The electrical circuit(s) of the invention can further comprise circuitry selected from signal processing circuitry, data retrieval circuitry and combinations thereof. The electrical circuit can comprise one or more circuitry modules, as integrated or discrete circuits. The sensor further comprises a communication link for electrical communication between each resonator(s) and the electrical circuit. Preferably, the electrical circuit comprises signal activation circuitry for generating electronic stimulus for stimulating the two or more resonators. The electrical circuit can further comprise at least one of signal conditioning circuitry, data derivation circuitry or data retrieval circuitry, for processing or retrieving a signal representing data originating from the two or more resonators. The communication link provides for electrical communication between the one or more resonators and the electrical circuit (including integrated circuitry or common associated discrete circuitry modules).

In general, the sensors used in the system of the invention (including with respect to each of the aforementioned approaches and embodiments), can be effective for sensing a fluid, monitoring a fluid, controlling a fluid, (e.g., as part of a process-control schema) and/or evaluating a fluid (e.g., determining one or more properties of a fluid in a fluidic system). Each of the mechanical resonators of the sensor can comprise sensing element (e.g., a flexural resonator) having a sensing surface adapted for or configured for contacting the fluid (or otherwise interacting with the fluid as appropriate for the particular sensor), and being responsive to changes in one or more properties of a fluid.

Generally, the embodiments discussed herein in connection with this (system) aspect of the invention, can be realized with many variations and/or more specifically-characterized embodiments based on specific details and features described within and/or readily ascertainable from the context of the Detailed Description of the instant specification (including combining the various features described therein in any and all possible combinations and permutations).

Preferred Embodiments—Methods And Systems, And Sensors Used Therein

The methods and systems of the invention can be more particularly described in connection with the several figures, as follows.

Figure 1C:
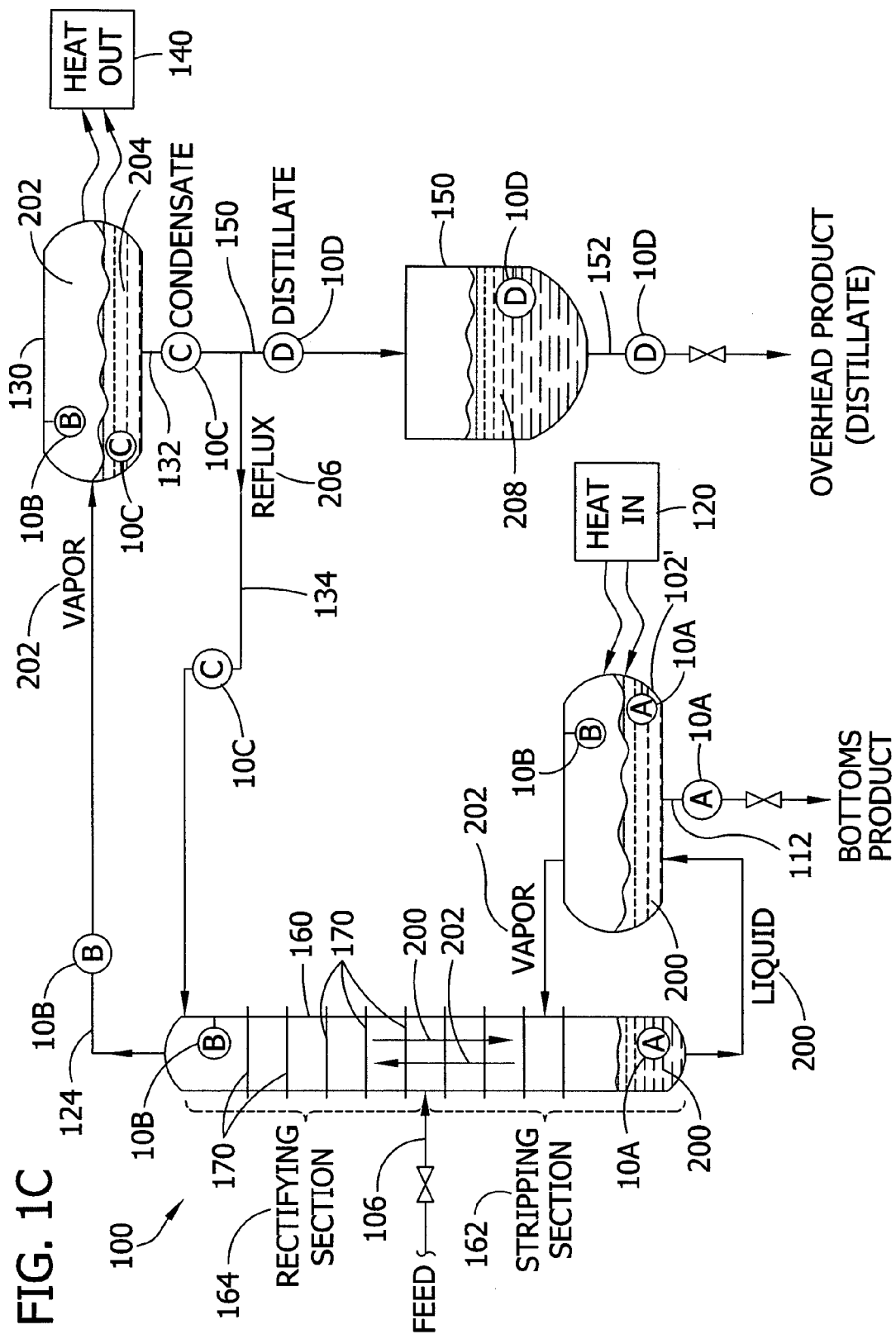

With reference generally to FIGS. 1A through 1E, a fluid process system 100 can be configured for distillation and can comprise one or more process containers such as a process vessel 102 or a process pipeline 104 for providing a multi-component composition 200 comprising the one or more liquid components. A feed line 106 can be used to supply the multi-component composition 200 to the process container (e.g., process vessel 102 or process pipeline 104). The process vessel 102 can also include one or more agitators 108, optionally in combination with one or more baffles (not shown) for effecting suitable mixing of components of the multi-component composition. The process vessel can also include a bottoms discharge line 112 for continuously, intermittently or batch-wise discharge of fluid from the process vessel 102 (e.g., after completion of a unit operation such as a solvent switching operation). A heat source (indicated generally as 120), such as a thermal jacket 122 or heating coils (not shown) can be associated with the process container(s) and can be adapted for vaporizing at least a portion of at least one liquid component of the composition 200 within a vaporization zone defined by vessel 102 to form a vapor 202. A vapor discharge line 124 can provide fluid communication between the process container (e.g., process vessel 102 or process pipeline 104) and a condenser 130 adapted for receiving the vapor 202. A heat sink (indicated generally as 140) can be associated with the condenser 130 for condensing the vapor 202 to form a condensate 204. A condensate discharge line 132 can provide fluid communication between the condenser 130 and a distillate receiver 150 for recovering at least a portion of the condensate 204 as a distillate 208. The distillate receiver 150 can be a process vessel (e.g., as depicted in FIGS. 1A, 1B, 1C and 1E and/or a process pipeline (as depicted in FIGS. 1B, 1C and 1E). A distillate discharge line 152 can be used to remove distillate from the distillate receiver 150. For distillation under reduced pressure, the a vent line (not shown) from condenser 130 or a vent line 151 from condensate receiver 150 may be connected in gas flow communication with a vacuum source 153 such as a vacuum pump or jet ejector (not shown). Where the vacuum source is connected to the condenser vent line, condensate discharge line 132 may comprise a barometric leg discharging below the condensate liquid level in condensate receiver 150.

With further reference to FIGS. 1A through 1E, the system generally further comprises one or more sensors (indicated generally as 10) configured in association with the fluid system such that the sensor can monitor a fluid within the fluid system. As shown in the various figures, particular sensors 10 are shown with a letter designation (e.g., 10A, 10B, 10C or 10D) referencing the fluid type being monitored thereby. Specifically, as depicted, sensors 10A are configured (including positioned appropriately) for monitoring a feed mixture comprising a multi-component composition 200 or the still bottom (residual liquid) fraction during the course of the distillation and/or at the end point thereof. Sensors 10B are configured (including positioned appropriately) for monitoring a primary vapor 202. Sensors 10C are configured (including positioned appropriately) for monitoring a condensate 204, including a refluxed condensate 206 (FIG. 1C). Sensors 10D are configured (including positioned appropriately) for monitoring a distillate 208.

FIG. 1A shows a distillation system 100 suitably adapted for single-stage batch distillations. In the system of FIG. 1A, multi-component composition and still bottoms sensors 10A can be located, for example, in bottoms discharge line 112 or in process vessel 102. Vapor sensors 10B can be located to monitor vapor 202 within process vessel 102 (e.g., in the vapor-containing headspace above the multi-component composition or residual liquid phase 200), or in-line within vapor discharge line 124, or within condenser 130. Condensate sensors 10C are preferably positioned for monitoring a condensate 204 within the condenser 130, or within the condensate discharge line 132. Distillate sensors 10D are positioned appropriately for monitoring a distillate 208 within the condensate discharge line 132 (in this FIG. 1A, the condensate and the distillate refer to the same fluid, as noted above), or within the distillate receiver 150, or within the distillate discharge line 152.

FIG. 1B shows a distillation system 100 as generally described above, but configured for multi-stage batch, semi-continuous or continuous distillations. As shown in FIG. 1B, the system further comprises a column 160 comprising a rectification zone which contains a plurality of vapor liquid equilibrium stages (e.g., comprising multiple sieve plates, not shown in FIG. 1B) positioned generally adjacent to and above the process vessel 102, and providing for gas-liquid contact between the multi-component composition or partially stripped liquid phase 200 (the flow of which is represented by the down arrow within the column 160) and the vapor 202 derived therefrom (the flow of which is represented by the up arrow within the column 160). Downward liquid flow within the column 160 is effected in part at least by reflux condensate 206 diverted from the condensate discharge line 132 through reflux line 134 into column 160.

In the system of FIG. 1B, multi-component composition sensors 10A can be located, for example, as described above in connection with FIG. 1A, as well as in the rectification zone defined by column 160. Vapor sensors 10B can likewise be located as described above in connection with FIG. 1A, as well as in column 160. Condensate sensors 10C can be positioned for monitoring a condensate 204 as described above in connection with FIG. 1A, and also for monitoring a condensate reflux 206 within reflux line 134. Distillate sensors 10D can be positioned for monitoring distillate 208 as described above in connection with FIG. 1A.

FIG. 1C shows a distillation system 100 as generally described above in connection with FIGS. 1A and 1B, but configured to be especially suitable for multi stage continuous distillations. As shown in FIG. 1B, the system further comprises a process vessel 102 operating as a reboiler 102', the reboiler 102' being in fluid communication with the bottom of fractionating column 160 (for liquid flow from the column 160 to the reboiler 102' and also being in fluid communication with a higher portion of the column 160 (for vapor flow from the reboiler 102' back to the column 160). As noted, the system of FIG. 1B further comprises a fractionating column 160 comprising multiple sieve plates 170 that also operates as a process vessel 102, and provides for substantial gas-liquid contact between the multi-component composition 200 (the flow of which is represented by the down arrow within the column 160) and the vapor 202 derived therefrom (the flow of which is represented by the up arrow within the column 160). In the depicted embodiment, the feed line 106 enters the column 160 substantially proximate to the center thereof (considered vertically). The portion of the column 160 upward from the feedline 106 is the rectifying section 162 comprising a plurality of rectifying stages; the portion of the column 160 downward from the feedline 106 is the stripping section 164 comprising a plurality of stripping stages. Downward liquid flow within the rectifying section 162 of the column 160 is effected in part at least by reflux condensate 206 diverted from the condensate discharge line 132 through reflux line 134 into column 160. Upward vapor flow within the stripping section 164 is effected in part by vapor 202 being fed to the column 160 from the reboiler 102.

In the system of FIG. 1C, multi-component composition sensors 10A can be located, for example, as described above in connection with FIGS. 1A and 1B, as well as in the reboiler 102'. Vapor sensors 10B can likewise be located as described above in connection with FIG. 1A and 1B, as well as in reboiler 102'. Condensate sensors 10C can be positioned for monitoring a condensate 204 as described above in connection with FIGS. 1A and 1B, and also for monitoring a condensate reflux 206 within reflux line 134 as describe in connection with FIG. 1B. Distillate sensors 10D can be positioned for monitoring distillate 208 as described above in connection with FIGS. 1A and 1B.

FIG. 1D shows a schematic side sectional view of a portion of column 160 that includes a sieve plate 170. As shown, the sieve plate 170 comprises a sieve tray 172, which itself can comprise a plurality of apertures 174 allowing vapor 202 to pass upward through the sieve tray 172. The upward traveling vapor 202 contacts a liquid phase 200 held above the sieve tray 172. The vapor velocity and pressure is sufficient to minimize liquid phase 200 flow downward through apertures 174. The level of liquid phase 200 above the sieve tray 172 is maintained at a desired level by overflow weir 176. As liquid phase 200 collects on the sieve tray 172, excess liquid phase 200 flows over weir 176 and downward through downcomer 178 to the next stage sieve plate (not shown) located therebelow. Excess liquid phase 200 from the sieve plate (not shown) immediately above the one depicted in FIG. 1D flows down through the downcomer 178 coming from that immediately-upper stage.

As shown in FIG. 1D, multi-component composition sensors 10A and vapor sensor 10B can be proximately associated with one or more stages of the column 160, for example, with one or more sieve plates 170 thereof.

Optionally, a liquid port 201*a* or vapor port 201*b* may be provide for withdrawal of a vapor or liquid fraction from tray 172. Withdrawal of vapor or liquid from the tray provides an intermediate cut that may constitute a desired produce, e.g., in petroleum refining or in chemical manufacturing processes which are used to separate a desired product as an intermediate cut in a single column from both light ends withdrawn from the top of the column and heavy ends withdrawn from the bottom. Where the intermediate cut is withdrawn from the rectification zone of the column, it may be deemed a "primary vapor fraction" where it is withdrawn as a vapor via a port 201*b*, or a distillate fraction where it is withdrawn as liquid phase via a port shown schematically at 201*a*. The precise arrangement for the liquid port is not shown, but any conventional arrangement can be used. Similar provisions may be made for removal of an intermediate cut condensate obtained by condensing a vapor withdrawn from port 201*b*. The composition and properties of this cut may be monitored by contact of a mechanical resonator with liquid phase that is withdrawn, by a vapor phase that is flashed from or in equilibrium with the liquid cut (e.g., placed within the vapor phase above the tray in the body of the column), by (the same) vapor phase as withdrawn via port 201*b*, or by a condensate condensed from or in equilibrium with that vapor phase. In the latter instance, the mechanical resonator can be placed below the liquid level on the tray, but since a two phase regime may tend to predominate in such region, it may be preferable to sense a condensate from a condenser for the withdrawn liquid phase outside the column.

In the context of the above description, the term "multi-component" may be deemed equivalent to "plural component," but it also expressly encompasses systems comprising more than two components. For example, in distillation operations such as a solvent switching operation, the system may comprise a binary solvent system wherein a relatively volatile solvent such as ethyl acetate or diethyl ether is displaced by a less volatile solvent such as n-heptane, or ternary solvent system in which the feed mixture comprises two relatively volatile solvents, both of which are substantially displaced by a solvent less volatile than either of them, such as where the feed mixture comprises both ethyl acetate and tetrahydrofuran which are displaced with n-heptane. In a further example of a multi-component system, crude petroleum comprising dozens or more individual species is distilled to yield multiple cuts of differing composition volatility and composition.

FIG. 1E shows a distillation system 100 as generally described above in connection with FIG. 1A, but configured to be especially suitable for flash distillation. In this embodiment, a multi-component composition 200 is fed from a feed line 106 and heated in the process pipeline 104. The multicomponent composition 200 partially vaporizes within the process pipeline 104, such that a two-phase fluid (200/202) exits the process pipeline into a process vessel 102. The process vessel 102 can be maintained under vacuum to further enhance separation. The liquid phase of the two-phase fluid (200/202) is recovered as a flash bottom product. The vapor phase of the two-phase liquid (200/202) is condensed and recovered as a distillate as generally described heretofore in connection with FIGS. 1A through 1C.

As shown in FIG. 1E, multi-component sensors 10A can be located within the process pipeline 104 and/or within the process vessel 102 as generally described above in connection with FIGS. 1A through 1C. Also, vapor sensors 10B can likewise be located within the process pipeline 104 and/or within the process vessel 102 as generally described above in connection with FIGS. 1A through 1C. Other sensors, including condensate sensors 10C and distillate sensors 10D can be positioned appropriately as generally described above in connection with FIGS. 1A through 1C.

In a further alternative embodiment, a feed mixture may comprise a vapor stream or mixed liquid and vapor stream that is introduced into a partial condenser where a portion of the vapor phase is condensed to produce a primary condensate and a residual vapor fraction. Thus, the primary condensate is relatively enriched in the relatively less volatile components of the feed mixture and the residual vapor fraction is enriched in the relatively more volatile components of the feed mixture at the temperature and pressure prevailing in the partial condenser. In monitoring and/or controlling the partial condensation process, the sensing surface of a mechanical resonator may be contacted with the primary condensate, the residual vapor fraction, another condensate condensed from or in equilibrium with the residual vapor fraction, and/or another vapor fraction flashed from or in equilibrium with the primary condensate. In a variation of partial condensation, the liquid phase from the partial condensation may be introduced into a fractional distillation column, e.g., at the head of a stripping zone comprised thereby. In this case, the primary condensate may comprise the liquid phase in the bottom stage of the stripping zone or a stage intermediate the feed stage and the bottom stage.

In its most general scope, partial condensation may also comprise introducing a vapor phase feed mixture, or a mixed phase feed mixture to the feed stage of a distillation column below a rectification zone, as more generally described hereinabove, in which case partial condensation is effected by contact of the feed mixture with the liquid phase descending from the equilibrium stage immediately above the feed stage. Where a rectification zone is provided, the "residual vapor fraction" in reference to partial condensation has the same meaning as "primary vapor fraction" in reference to distillation.

In monitoring distillation, partial condensation, and any or all of the other processes described herein, a signal from the mechanical resonator is indicative of a property of the sensed fluid such as viscosity, density, kinematic viscosity and dielectric constant. In some instances a signal or signals from the resonator may be processed to monitor a plurality of such properties. These properties typically vary with temperature, while the correlation between propert(ies) and composition is ordinarily calibrated for a specific temperature. In preferred embodiments of the invention, a sensor is provided for the temperature of the fluid in contact with the mechanical resonator, and the measured property or the signal reflecting the measured property is adjusted to compensate for the difference between calibration temperature and actual temperature according to an algorithm reflective of the temperature dependence of the property.

With or without temperature compensation, the signal is transmitted to a readout or recorder for display, and/or a controller for maintaining a control variable at a target value. In batch processes, e.g., batch reaction or batch distillation, the signal may be monitored for indication of the end point of the process. In either a batch or continuous distillation process, such variables as feed rate, reflux ratio, head pressure and boilup rate may be controlled in response to the signal received from the mechanical resonator.

Figure 2:
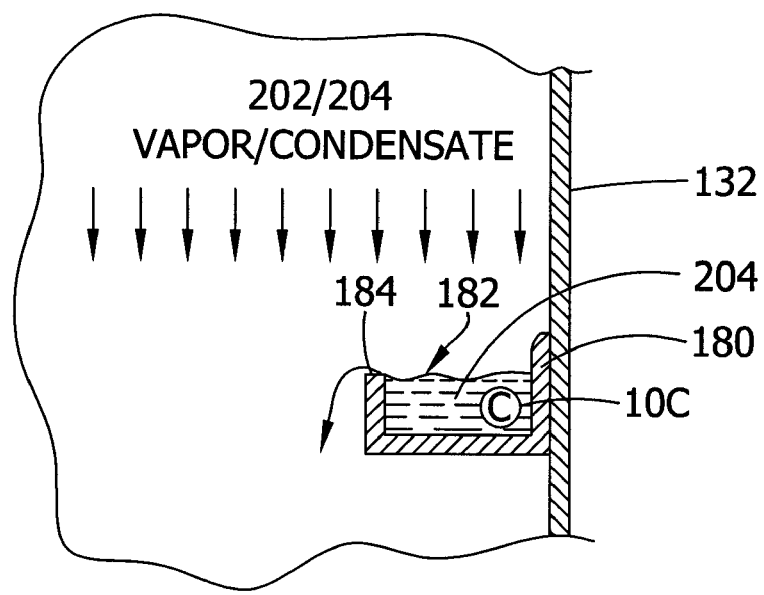
FIG. 2 is a schematic, cross-sectional view of a portion of a condensate discharge line that includes a sample collector.

FIG. 2 shows a schematic, cross-sectional view of a portion of a condensate discharge line 132 that includes a sample collector 180. Alternatively, the condensate discharge line may lead from a partial condenser as described hereinabove. The sample collector 180 can be suitably used, as necessary to collect a liquid-phase sample (e.g., for contact with a sensing surface of a mechanical resonator) and to monitor that liquid-phase sample (e.g., condensate 204) collected therein from a fluid stream that has a mixture of liquid-phase and a gaseous phase fluids. For example, such sample collectors may be advantageously employed in connection with sensors 10C positioned, for example, in the condensate discharge line 132. As shown, in one embodiment the sample collector 180 can comprises a sample well 182 formed between substantially opposing surfaces. The sample well 182 can have a sample weir 184 associated therewith for allowing collected condensate 204 to continuously overflow from the sample well 182 back into the condensate discharge line 132.

In any case, the fluid system 100 may be a fluid process system of any scale, including without limitation, research-scale systems (e.g., high-throughput experimentation research systems, bench-scale research systems), pilot-plant scale systems and/or industrial scale (commercial) systems. Particularly preferred systems and applications of commercial significance are described below.

Each of the aforementioned generally described distillation systems can be applied independently or in combination with each other, in each of the possible various permutations. Also, each of the aforementioned generally preferred approaches can be applied in further combination with more particular aspects, including particular protocols and/or particular systems or sensor features, as described herein.

Figure 12:
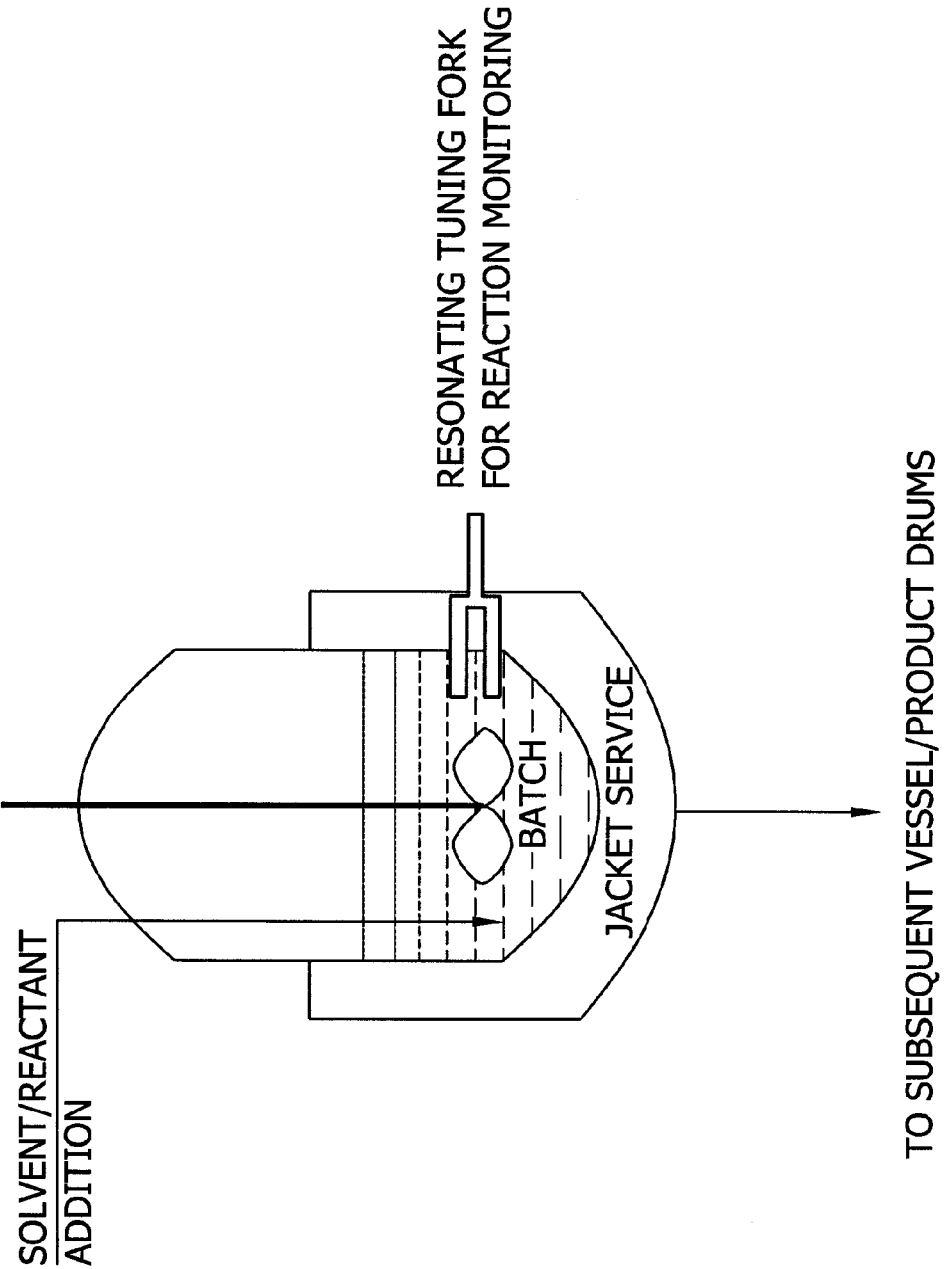
FIG. 12 is a schematic illustration of the operation of a batch stirred tank reactor, showing a resonating tuning fork in contact with the reaction medium for monitoring the progress of the reaction.

The method of the invention is also useful in monitoring and controlling chemical reactions for the preparation of inorganic products, organic non-polymeric products or polymeric products, in either laboratory investigations or in industrial manufacturing operation. FIG. 12 illustrates a conventional batch stirred tank reactor 301 provided with a jacket 303 into which a heat transfer fluid may be introduced to supply or withdraw heat for control of the reaction. Alternatively or in addition to the jacket, the reactor can be provided with interior coils (not shown) for supply or removal of heat. In this system, the reaction may be conducted in a liquid phase reaction medium 305 contained within reactor 301. Reactants, solvents, catalysts and other materials may be supplied through a charging line 307. An agitator 309 is provided for mixing materials within the reactor, pumping the reaction mass within the reactor and creating turbulence in aid of mass transfer within the reaction mass, or between the reaction mass and the gas phase in the head space, and heat transfer between the reaction mass and a heating or cooling fluid contained in or passing through jacket 303. As illustrated, the reaction system further comprises a vent line 309 for volatile components of the reaction mixture, and/or non-condensables from the head space, a reflux condenser 311 and a condensate return line 313 for return of condensate, e.g., a reaction solvent, to the reactor. It will be understood that none of the elements of the reaction system of FIG. 12 is essential in all cases, except for a reaction zone as provided in this instance by the reactor vessel 301. However, where present, the reactor feed line, the vapor vent line, the condenser and the condensate return line all provide locations wherein the state of the reaction system and progress of the reaction can be monitored and used for control. As those skilled in the art will appreciate, the system illustrated in FIG. 12 is relatively simple, and reaction system elements may typically be present in addition to those shown. By way of a common example, a gas feed line may be provided for purposes of introduction of a gaseous reactant, e.g., chlorine, air, molecular oxygen, ammonia, HCl, hydrogen sulfide, carbon monoxide, formaldehyde or phosgene during the course of the reaction. Another example is the provision of an external heat exchanger in a circulating line through which the reaction mass is circulated by a circulation pump located below an outlet at the bottom of the reactor.

A tuning fork or other mechanical resonator 315 is positioned within reactor 301 so that it may be maintained in contact with fluid present in the reactor. As shown, during the course of reaction, the resonator 313 is typically in contact with the liquid reaction medium. The reaction mass comprising the reaction medium may consist of a single liquid phase, plural liquid phases, e.g., a continuous liquid phase reaction medium having another liquid phase dispersed therein, or a slurry consisting of a continuous liquid phase reaction medium having a particulate solid phase material such as a catalyst for the reaction, dispersed therein.

As illustrated, the sensing surface of the resonator 315 is located at or below the level of the fluid reaction mass contained in the reactor. In such position, it may be used to monitor the density, viscosity, or dielectric constant of the fluid in which it is in contact, and thereby monitor any of a variety of conditions for purposes of process control. For example, a resonator located at an elevation corresponding to the desired liquid charge level in the reactor can be used in monitoring the charging process and determining when charging is complete. Through a feed back loop, it may function as a level sensor for a level controller which controls charging of reactants to the batch. A resonator located below the target liquid level may be used to monitor the progress of the reaction, e.g., the degree of conversion as a function of the changing composition on the viscosity, density, kinematic viscosity or dielectric constant of a single phase reaction mass, or of the continuous liquid phase within which other reaction mass components are suspended.

Mechanical resonators may be provided elsewhere in the system. Among the fluids which may be contacted are a liquid reaction medium, a solution comprising a reactant and/or product of the reaction in the reaction medium, a dispersion comprising a reactant and/or product of the reaction dispersed in the reaction medium, a vapor phase evaporated from the reaction medium, another liquid phase resulting from a phase separation during the reaction, another liquid phase comprising a source of reactant, a liquid phase sink for removal of product and/or a source of a phase transfer catalyst, or a dispersion comprising another liquid phase in a liquid reaction medium. For example, if the composition of the vapor stream flowing from the reactor to the condenser, or the condensate returning from the condenser to the reactor changes during the course of the reaction, changes in the density, viscosity, kinematic viscosity and/or dielectric constant of the vapor and/or condensate stream may be indicative of the progress of the reaction. Where a non-condensable gas is included in the vapor stream flowing from the reactor to the condenser, significant changes in density may occur as the reaction progresses. Similarly, changes in the various other fluids involved or produced in the reaction provide useful alternatives for monitoring or control.

Although FIG. 12 illustrates a batch stirred tank reactor, the method of the invention encompasses monitoring and controlling continuous reaction systems as well as batch. For example, in a continuous stirred tank reactor similar in configuration to the batch reactor of FIG. 12, a mechanical resonator may be used to monitor the condition of the product stream exiting the reactor, or as a sensor for a level controller which controls the rate of addition of reactants to the reactor or withdrawal of reaction product mass therefrom. Similar use of mechanical resonators may be used in a plug flow reactor, or in a series of cascaded continuous stirred tank reactors, wherein they may be placed, e.g., at a plurality of locations along the reaction flow path to monitor the reaction profile. In gas phase catalytic oxidation reactions, wherein a hydrocarbon and air or oxygen are introduced into a tubular reactor having a particulate oxidation catalyst within the tubes, the resonator may be used to monitor density, viscosity and/or dielectric constant of one or more of a reactant gas, a diluent gas, a gaseous feed mixture, a reaction product gas, a feed mixture comprising a condensed phase dispersed in a gaseous medium, a product mixture comprising a condensed phase dispersed in a gaseous medium, and a liquid phase condensed from the gas phase. For example, in a fluidized bed reaction system, mechanical resonator(s) may be located within the fluid bed and/or in a reaction effluent gas stream having fluidized catalyst suspended therein. In response to the measurement indicating the extent of conversion at a defined point in the flow path, a feedback control system may operate to adjust feed rates, reactant feed ratios, reaction temperature, total reaction pressure, or a gaseous reactant partial pressure to maintain a desired conversion and/or a desired level of productivity.

Where chemical reaction results in a change of state, mechanical resonators may be used to detect the point at which phase change occurs and monitor progress of the reaction beyond this point. For example, where reaction is accompanied by precipitation of a reaction product or by-product, there may be a relatively sharp discontinuity in fluid properties such as density, viscosity and/or dielectric constant vs. time at the point of incipient precipitation of such product or by-product. The operation and control of such processes is described in certain of the examples set out hereinbelow, and the observed effects illustrated in FIGS. 16-25. In other cases, gaseous reactants may combine to yield a product or by-product which spontaneously condenses as a liquid or solid, or which may be condensed by cooling the reaction product gas. In still further examples, solid and/or liquid reactants may combine to yield a product or by-product which is driven off from the reaction medium as a gas or vapor.

The method of the invention can be applied to any type of reaction system, whether inorganic, organic, polymeric and non-polymeric. For example, in a solution, suspension or emulsion polymerization or oligomerization reaction, the mechanical resonator may be contacted with a solution or dispersion of polymer or oligomer product in a liquid reaction medium. The sensor may be used in such system to monitor the viscosity, density, or kinematic viscosity of the solution or dispersion.

In all such chemical reaction processes, mechanical resonators may also be used for indication of quality control and/or as alarms to detect abnormal process conditions or the generation of unwanted by-products. In such instances, the function of the resonator may be to trip an alarm or an automated shutdown procedure in addition to or instead of normal process control procedures.

A flexural mechanical resonator may provide real time analysis of process fluids, and such real time analyses are of major value both in the laboratory investigation of chemical reactions and in the monitoring and control of industrial scale reactors. Traditionally, reaction end point determination and control have depended on analysis of off line samples. Some reaction systems have been provided with on-line analyzers based on analytical principles such as gas or liquid chromatography. These methods shorten the delay associated with drawings of samples and transporting them to a laboratory for analysis, but operation of even an on-line chromatograph requires time for sampling, injection and elution which precludes obtaining results in real time. Real time analyses can be made using spectroscopic techniques such as near infrared and Fourier Transform Infrared ("FTIR"), but spectroscopic methods typically require relatively complex calibrations which limit their practical utility. The response provided by a flexural mechanical resonator, on the other hand, can be readily and immediately analyzed mathematically to provide an instantaneous signal and readout for such parameters as density, viscosity and dielectric constant. Relatively straightforward correlations of these properties with composition, e.g., based on the relationship between density and molecular volume, allows composition to be determined relatively simply, economically, and with a high degree of accuracy in real time. These advantages apply not only in the instance of chemical reaction, but in the case of each and all of the various unit operations that are described and discussed herein.

Figure 26:
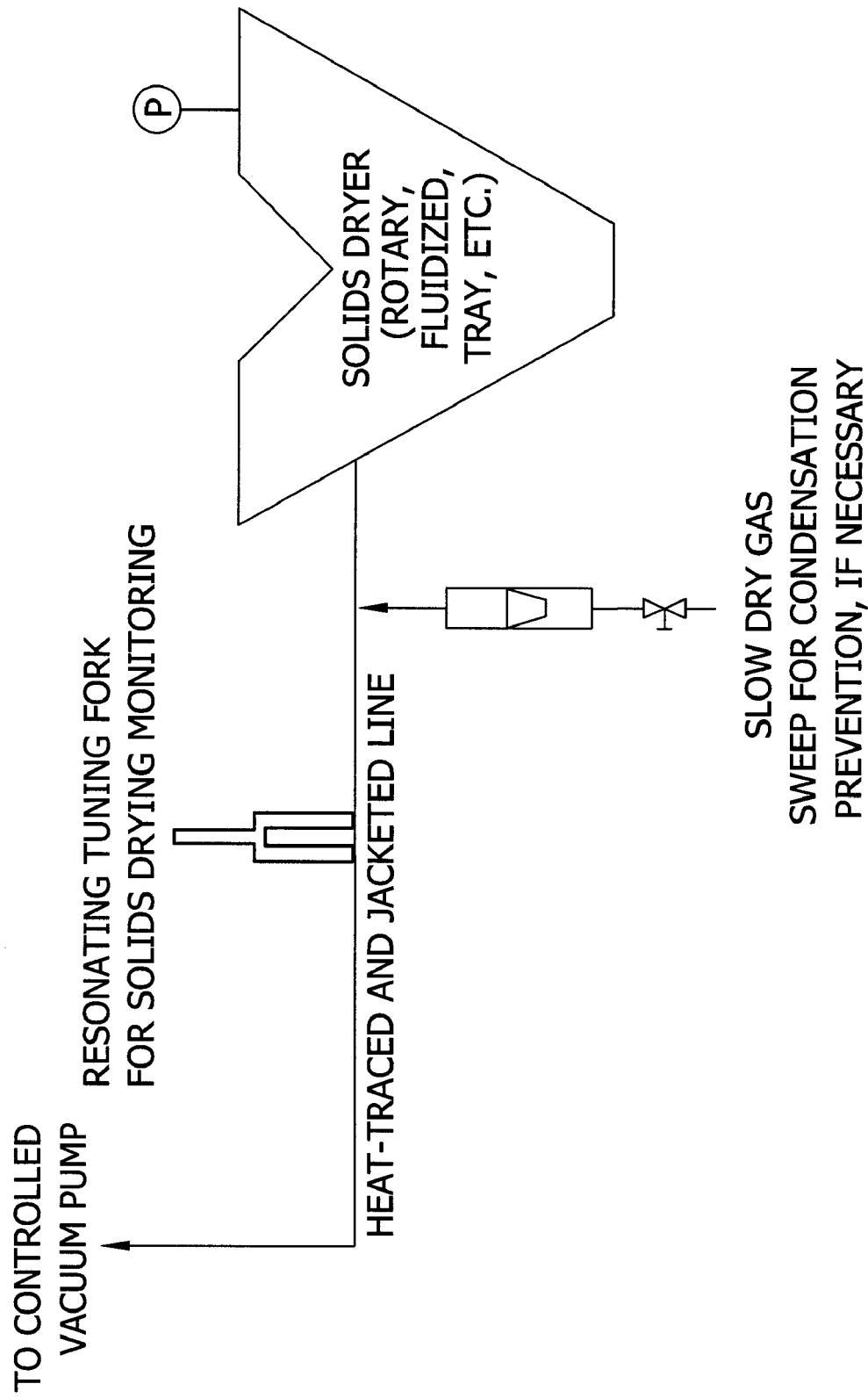
FIG. 26 is a schematic flow sheet of a process for drying of solids, illustrating placement of a tuning fork resonator in the vapor flow line from the dryer, prior to any associated liquid trap.

Illustrated in FIG. 26 is a system adapted for drying a particulate or granular solid product as conducted, e.g., in a process wherein a solid reaction product is crystallized from a reaction solution, or recrystallized from a recrystallization solvent, and separated from the crystallization mother liquor by filtration or centrifugation. To produce a dry, typically flowable, solid product, volatiles such as moisture and/or organic solvents are commonly removed by drying. The system of FIG. 26 comprises a dryer vessel 401 which may, for example, be a rotary dryer, a fluidized bed dryer, a tunnel dryer, tray dryer, etc. A vapor line 403 from the dryer is in gas flow communication with an induced draft blower (not shown) or a vacuum source 405 such as a vacuum pump or jet ejector. Optionally, a non-condensable stripping gas such as air or nitrogen may be provided via a gas supply line 407. Typically heat is supplied to the dryer, either in the stripping gas (e.g., heated air or superheated steam) or by a jacket 409 or coils (not shown) that are associated with the dryer vessel and in heat transfer communication with the material to be dried therein. In some applications, especially where there is no stripping gas or other significant non-condensable content of the vapor exiting the dryer via line 403, a dry gas may be injected from a dry gas supply 411 at a relatively slow rate preferably just sufficient to prevent condensation of vapor upstream of the vacuum source without overloading a vacuum pump or ejector.

A mechanical resonator 413 located in vapor line 403 contacts the vapor exiting the dryer. By monitoring the density, viscosity, and/or dielectric constant of the vapor, the progress of the drying operation may be monitored. Under the influence of the blower, vacuum pump or ejector, there is typically a substantially constant flow of non-condensable gas through the vapor line, either as a stripping gas that is metered into the dryer, or as relatively minor volume of environmental air that is drawn in as "leakage" into the system, e.g., through shaft seals and the like. Because the non-condensable flow is generally substantially constant where air or other carrier gas is used, and is also generally constant in a vacuum drying system, at least once the dryer apparatus has been evacuated, residual moisture or other volatile content of the solids is typically reflected in the partial pressure of moisture or other volatiles in the gaseous stream exiting the dryer. Thus, as drying proceeds, the flow rate of vapor driven off from the solids declines so that the relatively proportion thereof drops, and the relative proportion of non-condensable increases, in the vapor line. This shift in composition may be reflected in the density, viscosity and/or dielectric constant of the vapor stream in line 403, which may then be monitored to identify the end point of batch drying operation or to control a continuous drying operation, e.g., by adjusting feed rate, vacuum, heat input, stripping gas flow rate to maintain a density, viscosity, dielectric constant, etc., that is (are) associated with adequate removal of volatiles from the feed. The operation and control of such drying processes are described in certain of the examples set out hereinbelow, and the observed effects illustrated in FIGS. 26-30.

Although the change in composition of the vapor stream may shift more radically in a vacuum dryer operation, the method of the invention can be as effective, or more effective, in an atmospheric or positive pressure dryer since the vapor density difference between the solvent removed and the non-condensables increases with the system pressure.

The invention is further directed to a method for monitoring a process comprising a membrane separation. In a membrane separation operation, a feed mixture is introduced into a feed zone on an upstream side of a membrane separator at a pressure higher than the pressure in a permeate zone on the other side of the membrane. The pores of the membrane may be sized to pass one component of the feed mixture but not another, or at least to pass one component preferentially to the other. For example, as in reverse osmosis, they may be sized to pass a solvent, but not a solute dissolved therein. Such membranes are also used for gas separations producting a permeate fraction relatively enriched in one or more of the gas components, and a retentate (or more typically a tangential flow fraction) relatively enriched in one or more others. Often in such applications, multiple membranes in series are used to yield gas fractions that are progressively enriched in a desired component, or depleted with respect to an undesired component. Flow in the feed zone may be dead-headed against the membrane; or, as in tangential flow filtration, may flow parallel to the membrane, yield a tangential flow stream. In either case, passage of a fluid through the membrane yields a permeate in the permeate zone and a retentate in the feed zone, or tangential flow fraction in a discharge stream exiting said feed zone.

Fluids

Generally, as noted above, the multi-component composition can comprise a multi-component solution or a multi-component dispersion, in each case comprising one or more liquid phase media. Although the particular nature of the multi-component composition is not critical to the methods and systems of the invention, the multi-component composition can, in some applications, preferably comprises organic molecules, such as non-polymeric organic molecules, together with one or more liquid-phase components, typically in a solution or dispersion. Such non-polymeric organic molecules are used to great extent within the pharmaceutical industry, as active pharmaceutical ingredients (API's) as well as intermediates in the synthesis and/or manufacture thereof.

The sensors of the methods and systems of the invention, including mechanical resonator sensors and other sensors described herein (e.g., refractive index sensors) are well suited for monitoring and/or controlling separation operations involving such multi-component compositions. Mechanical resonators such as flexural resonators can be used, for example, in connection with liquids or gasses having a wide range of fluid properties, such as a wide range of viscosities, densities and/or dielectric constants (each such property being considered independently or collectively as to two or more thereof). For example, liquid fluids can generally have viscosities ranging from about 0.1 cP to about 100 000 cP, and/or can have densities ranging from about 0.0005 g/cc^3 to about 20 g/cc^3 and/or can have a dielectric constant ranging from about 1 to about 100. Gaseous fluids can, for example, generally have viscosities ranging from about 0.001 to about 0.1 cP, and/or can have densities ranging from about 0.0005 to about 0.1 g/cc^3 and/or can have a dielectric constant ranging from about 1 to about 1.1. The fluids can be ionic fluids or nonionic fluids. As an example, ionic fluids can have a conductivity ranging from about 1 Ohm.cm to about 1 GOhm cm. The fluids of the invention can include relatively pure liquid or gaseous elements (e.g., liquid $N_2$, gaseous $O_2$, gaseous or liquid $H_2$) or relatively pure liquid or gaseous compounds (e.g., liquid $H_2O$, gaseous $CH_4$).

The fluids being sensed in connection with the methods and systems of the invention can be single-phase or multi-phase mixtures of gases, liquids and/or solids, including for example: mixtures of gases; mixtures of liquids (e.g., solutions); two-phase mixtures of a first liquid and a second liquid (e.g., liquid-liquid emulsion); two-phase mixtures of liquids and gases (e.g., a liquid having gas sparging or bubbling, e.g., a liquid nebulized through a gaseous environment); two-phase mixtures of liquids and solids (e.g., colloidal solutions; dispersions; suspensions); and/or three-phase mixtures of gasses, liquids and solids. As discussed in further detail elsewhere herein, mechanical resonators generally, and flexural and torsional resonators in particular, are separately and simultaneously capable of measuring variables such as density, viscosity, kinematic viscosity, dielectric constant, etc. For certain streams in certain applications, multiple such composition dependent variables may be simultaneously sensed as a function of resonator response, and separate readouts and/or records can be generated for these variables. In other process operations, it may be preferable to select only a single variable as indicative of composition. The normal or anticipated variations in composition of some process fluids may not have a marked effect on all the fluid parameters such as density, viscosity and dielectric constant. In the latter circumstances, the variable selected for monitoring is preferably one which changes relatively sharply as a function of composition.

Operating Conditions

The operating conditions of the fluid in the fluid system is not narrowly critical to the invention. Generally, the fluids within a particular fluid system and/or fluids in different fluid systems can be processed and/or generated under widely varying process conditions, such as temperature, pressure flowrate. Generally, the temperature can range from above the freezing point of the fluid to above the vaporization temperature, including for example to superheated temperatures and/or supercritical conditions. Particular temperature ranges can be preferred for particular fluids. Generally, the pressure within a fluid system can likewise cover a wide range, including for example ranging from about vacuum conditions to about 25,000 psig. In preferred applications, the pressure can be lower, ranging from vacuum conditions to about 15,000 psig, from vacuum conditions to about 10,000 psig, from vacuum conditions to about 5,000 psig, from vacuum conditions to about 1,000 psig, from vacuum conditions to about 500 psig, or from vacuum conditions to about 100 psig. In various alternative embodiments, the pressure range in each of the aforementioned ranges can have lower pressure limit of about 1 psig or about 10 psig or about 20 psig. Mechanical resonators described herein are generally useful under all pressure conditions, provided they are properly sealed.

Monitored Property/Properties

In the methods and systems and apparatus of the invention, the particular property being monitored is not narrowly critical. In general, the property of interest will depend on the fluid and the significance of the monitoring with respect to a particular fluid system in a particular commercial application. The property being monitored for a particular fluid system also depends on the type of sensor. Significantly, some properties of fluids (both liquids and gasses) are of general importance across a wide range of commercial applications. For example, the viscosity of a fluid is of near universal interest for many fluid systems. Likewise, the density of a fluid is also of great general interest for many fluid systems. It is especially advantageous to be able to monitor both viscosity and density of a fluid—based on the same monitoring event (e.g., concurrently or simultaneously, using the same sensing element, on the same fluid sample). Significantly, flexural resonators such as tuning forks, unimorphs (e.g., disc benders), bimorphs, torsional resonators, etc. have been demonstrated by Matsiev et al. to have the capability of such concurrent or simultaneous monitoring of both viscosity and density. See Matsiev, "*Application of Flexural Mechanical Resonators to Simultaneous Measurements of Liquid Density and Viscosity*," IEEE International Ultrasonics Symposium, Oct. 17-20, 1999, Lake Tahoe, Nev., which is incorporated by reference herein for all purposes, and see also commonly-owned U.S. Pat. Nos. 6,401,519; 6,393,895; 6,336,353; 6,182,499; 6,494,079 and EP 0943091 B1, each of which are incorporated by reference herein for all purposes. Dielectric constant is also a very significant property of interest for many commercial applications—particularly for applications involving ionic liquids. See Id. Other properties can also be of interest, alternatively to or in addition to the aforementioned properties. For example, temperature and/or pressure and/or flow rate are similarly of near-universal interest across a wide range of commercial applications. Parallel resistance can also be of interest.

Mechanical Resonator Sensors

In preferred applications, the fluid(s) contained within, constrained by, originated from, or otherwise associated with the fluid system 100 are being sensed using mechanical resonator sensors 10 comprising mechanical resonators 40, various details and applications of which are further illustrated in FIGS. 3A through 3D, FIGS. 4A through 4I, FIGS. 5A through 5C, FIGS. 6A through 6E and FIGS. 7A through 7D.

For mechanical resonator sensors (e.g., 10A, 10B, 10C and 10D) sensing surfaces of the one or more resonators are contacted with fluid(s) at the one or more positions, preferably during a sensing period. The one or more resonators can be stimulated, preferably during the sensing period and while their sensing surfaces are in contact with the fluid. The one or more resonators can be stimulated actively (e.g., using an electrical activating signal) or passively (e.g., without an activating signal) to generate signals associated with the respective resonator responses. The generated signals are communicated, as individual signals or as multiplexed signals, over one or more communication paths to electrical circuitry (generally shown in the various figures as 20/30 for signal processing and/or data retrieval). If multiple signals from multiple resonators are multiplexed, the multiple signals can be subsequently deconvoluted, for example by processing the signals to characterize the responses, and then associating the characterized responses of the resonators with specific positions of respective resonators.

In preferred methods, the characterized responses of the resonators are also used to determine one or more properties of the fluid being sensed. Fluid properties can be advantageously determined using flexural resonators such as tuning forks, for example (e.g., to determine viscosity, density, dielectric and conductivity). Generally, at least one property, and preferably two or more properties of the fluid at each of the multiple positions is determined. Typically, the at least one property is determined at multiple positions by correlating the respective responses associated with each resonator with the at least one property of the fluid, for example, based on at least one of the signal characteristics of the characterized responses of the resonators.

Generally, signals generated in association with the response(s) of the mechanical resonator(s) can be communicated over (one or more) communication paths. The particular nature of the communication path is not narrowly critical. The communication path can typically comprise for example, a plurality of a conductive paths such as conductive wires, conductive thin-film connectors or other conductive connectors. Alternatively, however, the communication path can be realized (over its entirety or over a portion thereof) using for example acoustic paths (e.g., solid waveguides, such as solid rods), magnetic paths (e.g., inductive coupling, such as across a fluidic barrier), or electromagnetic paths (e.g. electromagnetic radiation such as microwave radiation, visible light radiation, infrared radiation, etc., typically applied in connection with a wave guide such as a fiber optic, etc.). Regardless of the particular manner in which the communication path is realized, the mechanical resonators can be configured in any suitable manner with respect to electrical connection to the communication path. The particular configuration will depend upon the type of mechanical resonators employed, including for example, the number of electrodes and the configuration of the electrodes associated with the resonators, how the resonators are stimulated (e.g., actively versus passively), etc.

In each of the aforementioned generally preferred approaches and/or embodiments of the methods and sensors and systems of the invention, the sensor(s) can be employed for sensing, monitoring and/or evaluating one or more fluids in one or more fluidic systems.

In general, as noted above, the particular sensing element of the sensor of the methods and systems and apparatus of the present invention is not limited. Generally, the sensing elements useful in connection with this invention are adapted to monitor one or more properties of a fluid—that is, to generate data associated with one or more properties of the fluid. The data association with a property in this context means data (typically obtained or collected as a data stream over some time period such as a sensing period), including both raw data (directly sensed data) or processed data, can be directly informative of or related to (e.g., through correlation and/or calibration) an absolute value of a property and/or a relative value of a property (e.g., a change in a property value over time). In many applications, the raw data can be associated to a property of interest using one or more correlations and/or using one or more calibrations. Typically such correlations and/or calibrations can be effected electronically using signal processing circuitry, either with user interaction or without user interaction (e.g., automatically).

Particular sensing elements for the sensor 10 can be selected based on needed or desired property (or properties) of interest, and on required specifications as to sensitivity, universality, fluid-compatability, system-compatability, as well as on business considerations such as availability, expense, etc. Because of the substantial universal nature of viscosity and/or density and/or dielectric properties for many diverse fluid systems, sensor elements that are suited for monitoring these properties are preferred. There are many sensor elements known in the art for measuring one or more of viscosity, density and/or dielectric. Accordingly, the selection of one or more of such sensor element types is not critical to the invention. However, in many applications the use of mechanical resonators, and especially flexural or torsional resonators, offers significant advantages.

Preferably, the sensor 10 comprises a mechanical resonator sensor. The mechanical resonator can include, for example, flexural resonators, surface acoustic wave resonators, thickness shear mode resonators and the like. Various types of flexural resonators can be employed, including for example tuning forks, cantilevers, bimorphs, unimorphs, membrane resonators, disc benders, torsion resonators, or combinations thereof. Flexural resonator sensing elements comprising tuning fork resonators are particularly preferred. The tuning fork resonator can have two tines (e.g., binary-tined tuning fork) or more than two tines, such as three tines (e.g., a trident tuning fork) or four tines (e.g., a quaternary-tined tuning fork). In some applications, a tuning fork resonator may be configured (e.g., with respect to geometry and electrode configuration) for resonating within a single plane. For some applications, a tuning fork may be may be configured (e.g., with respect to geometry and electrode configuration) for resonating in two or more different planes relative to each other, such as in two planes perpendicular to each other.

Such flexural resonator sensors are known in the art. See Matsiev, "*Application of Flexural Mechanical Resonators to Simultaneous Measurements of Liquid Density and Viscosity,*" IEEE International Ultrasonics Symposium, Oct. 17-20, 1999, Lake Tahoe, Nev., which is incorporated by reference herein for all purposes, and see also commonly-owned U.S. Pat. Nos. 6,401,519; 6,393,895; 6,336,353; 6,182,499; 6,494,079 and EP 0943091 B1, each of which are incorporated by reference herein for all purposes. More recent advances include those described in co-pending applications, such as U.S. Ser. No. 10/452,264 entitled "*Machine Fluid Sensor And Method*" filed on Jun. 2, 2003 by Matsiev et al. (co-owned, describing applications involving flexural resonator technologies in machines, such as transportation vehicles); U.S. Ser. No. 60/505,943 entitled "*Environmental Control System Fluid Sensing System and Method*" filed on Sep. 25, 2003 by Matsiev et al. and related PCT Application No. PCT/US03/32983 entitled "*Environmental Control System Fluid Sensing System and Method*" filed on Oct. 17, 2003 by Matsiev et al. (each co-owned, describing applications involving flexural resonator technologies in heating, ventilation, air-conditioning and refrigeration systems and in machines such as engine systems related thereto); U.S. application Ser. No. 2002/0178805 A1 (describing applications involving flexural resonator technologies in down-hole oil well applications such as well-logging systems); U.S. Ser. No. 10/804,446 entitled "*Mechanical Resonator*" filed on Mar. 19, 2004 by Kolosov et al. (co-owned, describing various advantageous materials and coatings for flexural resonator sensing elements); U.S. Ser. No. 10/804,379 entitled "*Resonator Sensor Assembly*" filed on Mar. 19, 2004 by Kolosov et al., and PCT Application. No. PCT/US04/08552 entitled "*Resonator Sensor Assembly*" filed on Mar. 19, 2004 by Kolosov et al. (each co-owned, describing various advantageous packaging approaches for applying flexural resonator technologies); and U.S. Ser. No. 10/394,543 entitled "*Application Specific Integrated Circuitry For Controlling Analysis For a Fluid*" filed on Mar. 21, 2003 by Kolosov et al., and PCT Application. No. PCT/US04/008555 entitled "*Application Specific Integrated Circuitry For Controlling Analysis For a Fluid*" filed on Mar. 19, 2004 by Kolosov et al. (each co-owned, describing electronics technologies involving application-specific integrated circuit for operating flexural resonator sensing elements), each of which are incorporated herein by reference for all purposes, and each of which includes descriptions of preferred embodiments for flexural resonator sensors and use thereof in connection with the methods and apparatus and systems of the present invention. Further details regarding flexural resonator sensors and/or flexural resonator sensing element are described below, but are generally applicable to each approach and/or embodiment of the inventions disclosed herein.

Figure 3A:
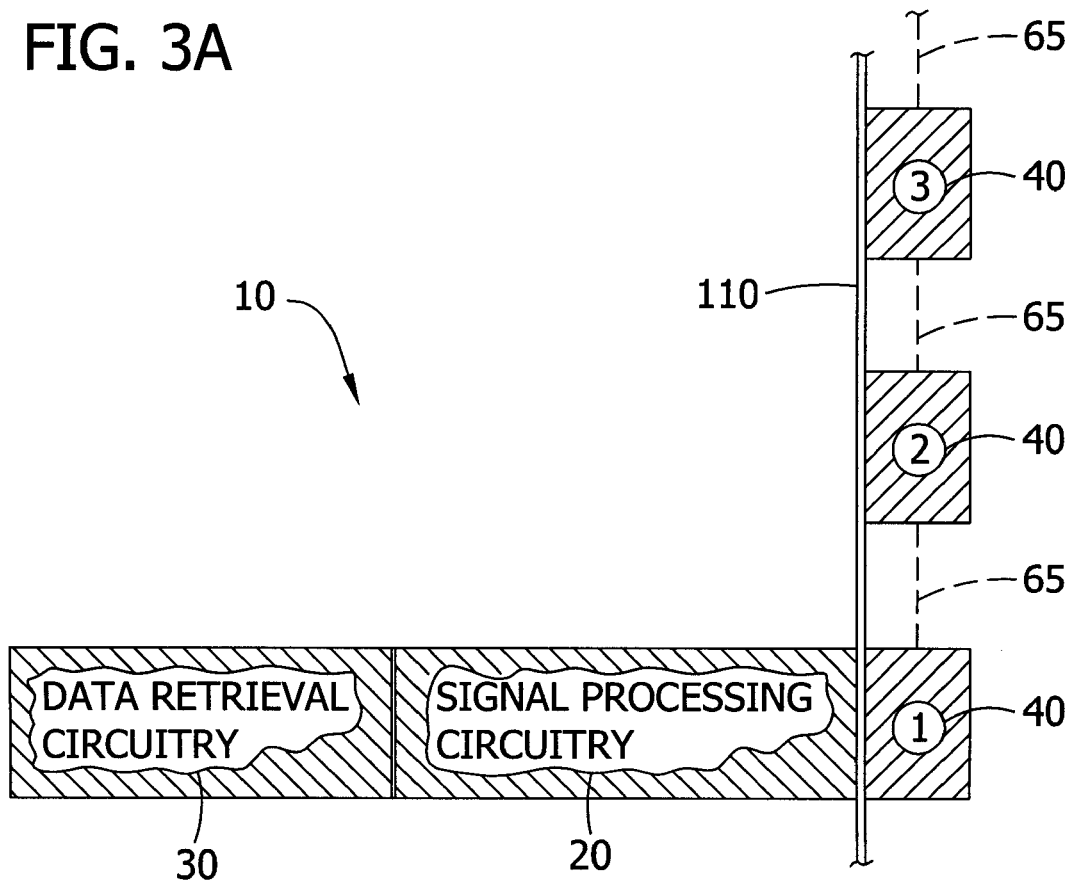

With further reference to FIGS. 3A through 3D, generally, each of the mechanical resonators 40 of the sensor 10 can comprise one or more sensing surfaces 50 that can be exposed to a fluid during a sensing operation. The sensor can also comprise one or more additional sensing elements 51, and in some embodiments, each of the multiple mechanical resonators 40 can be employed together with corresponding additional sensing elements 51 such as additional temperature sensing elements 51. With reference briefly to FIG. 3D, the sensing surfaces 50 of the mechanical resonators 40 can be optionally situated in a sensing element housing 52 such that a sensing surfaces 50 can be exposed to the fluid (e.g., via housing window 54).

Although much of the description is presented herein in the context of flexural resonator sensors, various aspects of the invention are not limited to such sensors. Hence, other types of sensors (or sensor subassemblies) can also be used in place of mechanical resonators. In addition, other sensors (or sensor subassemblies) can be used in combination with the mechanical resonator sensor or other types of sensors mentioned above. Particularly preferred sensors for use in combination with mechanical resonators, such as flexural resonators, include temperature sensors, pressure sensors, flow sensors, conductivity sensors, thermal conductivity sensors, among others.

Barrier Interface

Generally, the fluid process system 100 can comprise one or more couplings 60 for interfacing the sensor (such as sensor 10) across a fluid barrier 110, as shown for example in FIGS. 3A through 3D. Although illustrated generally with circuits 20, 30 external to the fluid being sensed, in some applications the circuits 20, 30 (and indeed the entire sensor 10) is situated internal to the fluid system and exposed to the fluid; thereby obviating the need for the coupling 60. Packaging approaches are known in the art for such internally-situated electronics circuits 20, 30.

With further reference to FIG. 3D, for example, the installed sensor 10 can also optionally comprise a coupling 60 providing electrical or mechanical access across the fluidic barrier 110. The coupling 60 can comprise a set of conductive paths (not shown) providing electrical communication through the barrier 110 to a signal processing circuit 20 or data retrieval circuit 30, preferably situated on the external side of the barrier 110 of the fluid system 100 (e.g., mounted on the external side of the coupling 60, as shown).

As described above, the sensor 10 can be interfaced with the fluid system(s) across a barrier 110 that defines at least a portion of the fluid system(s). Preferably, the sensor 10 is interfaced across the barrier without substantially compromising the integrity of the fluid system. With further reference to the various figures discussed above, a sensor 10 can be interfaced with a fluid system 100 across a barrier 110 using a coupling 60. The coupling 60 can generally be a mechanical coupling, an electrical coupling and/or a magnetic coupling. In one approach, the coupling 60 can comprise one or more bodies having a first surface on the internal fluid-side of the barrier 110, and an opposing second surface on the external side of the barrier 110. The body of the coupling 60 can be affixed to (e.g., fixedly mounted on, fixedly attached to) the barrier 110. Alternatively, the body of the coupling 60 can be integrally formed with the barrier 110. The body of the coupling 60 can alternatively be removably engaged with the barrier 110. In any case, the coupling 60. As noted, the coupling 60 can further comprise one or more conductive paths (e.g., wired electrical leads) extending through the body thereof. The one or more conductive paths can each have corresponding end terminals preferably exposed at one or more surfaces of the body, and adapted for providing electrical connection across the barrier 110 between the mechanical resonators 40 (and other sensing element 51) and signal processing circuitry and/or data retrieval circuitry. The terminals can comprise, for example, contact pins or contact pads.

Sensor Circuitry

With reference to FIGS. 3A through 3D, the sensor 10 further comprises one or both of a signal processing circuit 20 or a data retrieval circuit 30.

The sensor 10, as shown in FIG. 3A, can comprise two or more mechanical resonators 40 (e.g., a flexural resonators) linked by a common communication path 65 to a circuit. The circuit preferably comprises either a signal processing circuit 20 (e.g., comprising amplifier circuitry), or a data retrieval circuit 30 (e.g. comprising data memory circuitry, perhaps adapted for recording raw data received from the mechanical resonators 40). In a generally more preferred embodiment the sensor 10 can comprise two or more installed mechanical resonators 40 (e.g., two or more flexural resonators) commonly communicating with both signal processing circuitry 20 and data retrieval circuitry 30.

Generally, the signal processing circuit 20 can comprise one or more of signal conditioning circuitry 24 and data derivation circuitry 26, separately or in combination. If the mechanical resonators 40 are to be actively stimulated using an electronic stimulus, the signal processing circuit 20 can further comprise optional signal activation circuitry 22.

Generally, referring further to FIGS. 3A and 3B, the signal processing circuit 20 can comprise one or more circuits (or circuit modules) for activating sensing surfaces 50 of mechanical resonators 40 and/or for processing data originating with a sensing surface 50 of a resonator 40. Generally for example, the signal processing circuit can comprise: a signal activation circuit 22 (generally optional, e.g., for providing an electronic stimulus to the sensing element during active sensing, as discussed in more detail below); a signal conditioning circuit 24 for processing data originating from the sensing element (generally preferred, e.g., for altering an electronic characteristic of a data signal, typically resulting in a conditioned data or data stream); and/or a data derivation circuit 26 for processing data originating from the sensing element (generally preferred, e.g., for identifying, selecting or interpreting a particular electronic characteristic of a data signal, typically resulting in derived data or data stream that is more closely related to the property (or properties) of interest (e.g., has higher information content and/or greater information value) than a raw data stream and/or a conditioned data or data stream).

Figure 3C:
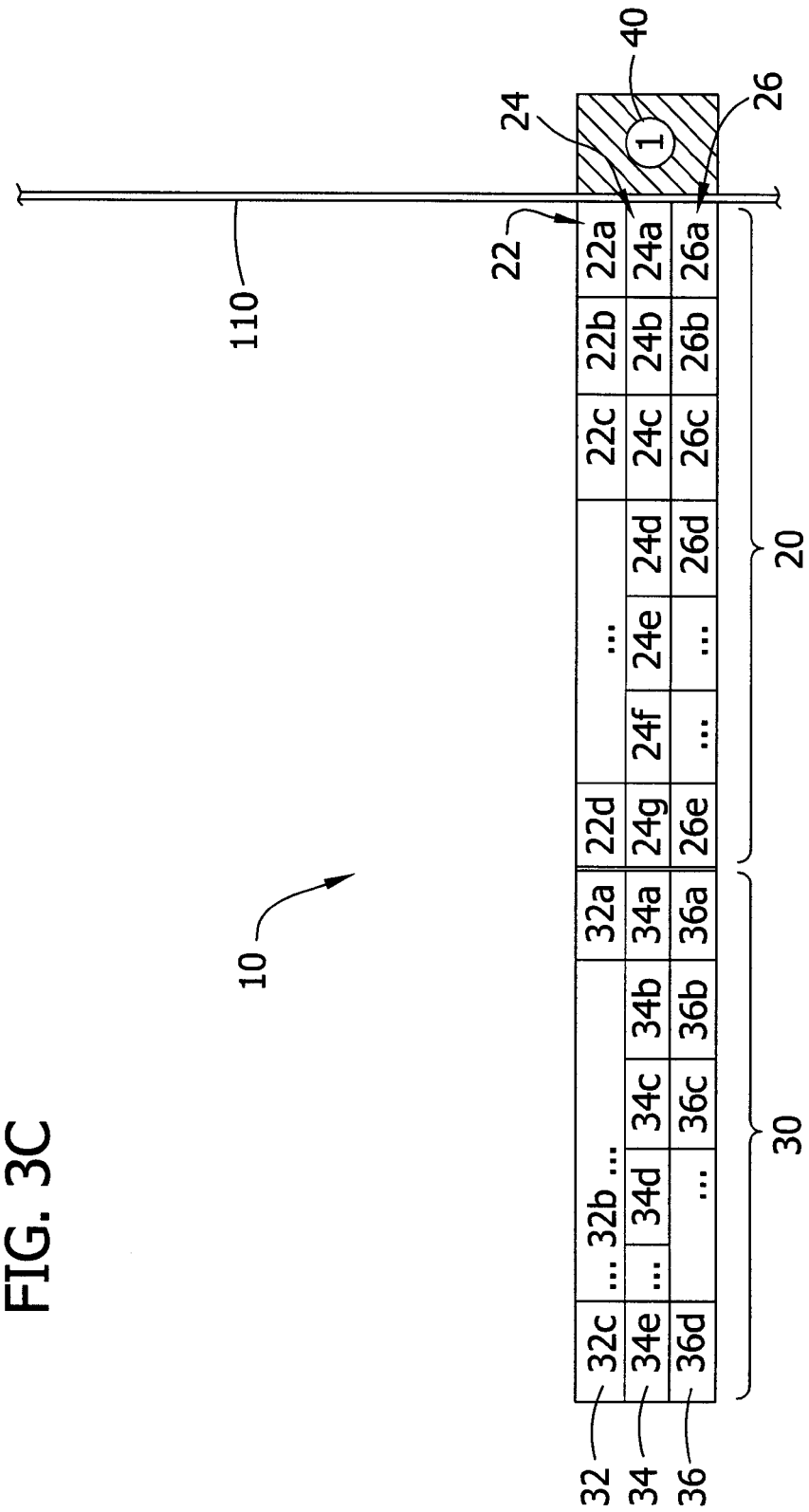

In particular, with further reference to FIG. 3C, the signal processing circuit 20 can comprise one or more circuits (or circuit modules) as signal conditioning circuits 24, such as for example: signal input circuitry 24a (e.g., for receiving a response signal from the sensing surface 50 of the resonator 40); amplifying circuitry 24b (e.g. including pre-amplifiers and amplifiers, for amplifying a signal); biasing circuitry 24c (e.g., for offsetting or otherwise changing a reference frame relating to the signal, including such as for reducing analog signal offsets in the response signal); converting circuitry 24d (e.g., analog-to-digital (A/D) converting circuitry for digitizing data or a data stream); microprocessor circuitry 24e (e.g., for microprocessing operations involving data originating from the sensing element and/or user-defined data); signal-processing memory 24f (e.g., typically being accessible to one or more signal processing circuits or circuit modules for providing data thereto, such as for example system-specific and/or sensing-element-specific identifying indicia, user-defined data for signal conditioning, etc.); and/or signal output circuitry 24g (e.g., for outputting a conditioned signal to another circuit module (e.g., to a data derivation circuit and/or to a data retrieval circuit).

Referring again to FIG. 3C, the signal processing circuit 20 can comprise one or more circuits (or circuit modules) as data derivation circuits 26, such as for example: signal input circuitry 26a (e.g., for receiving a response signal from the sensing surface 50 of the resonator 40 or from one or more data conditioning circuits 24); signal detection circuitry 26b (e.g., for identifying and/or detecting one or both of phase data and/or amplitude data and/or frequency data of the response signal); microprocessor circuitry 26c (e.g., for microprocessing operations involving data originating from the sensing element, typically involving a microprocessor configured for processing one or more software operations such as software algorithms or firmware algorithms (e.g., a data-fitting algorithm) for determining a parameter of the fluid that is associated with a property thereof, and/or typically for processing user-defined data (e.g., predefined data and/or substantially concurrently-defined data) in conjunction with the data originating from the sensing element, and/or typically involving user-initiated, user-controllable, and/or user-interactable processing protocols, typically for determining a parameter using a calibration with a fitting algorithm, for determining a parameter using a correlation algorithm, for determining a change in a detected signal characteristic (e.g., frequency, amplitude) or for determining a determined parameter); signal-processing memory 26d (e.g., typically including electronic data storage media, such as non-volatile memory (e.g., ROM, PROM, EE-PROM, FLASH memory, etc.), typically being pre-loaded with and/or being accessible for loading user-defined data (e.g., calibration data, correlation data, data defining approximated fluid properties, system-specific information, sensing-element specific information such as an identifying indicia, and/or typically being accessible to one or more signal processing circuits (or circuit modules) for use thereof, and/or signal output circuitry 26e (e.g., for outputting a conditioned signal to another circuit module (e.g., to a data derivation circuit and/or to a data retrieval circuit).

The data retrieval circuit 30 can comprise data storage circuitry 32 and/or data display circuitry 24, separately or in combination. The data retrieval circuitry 30 can likewise comprise data transmission circuitry 36.

The data storage circuitry 32 of the data retrieval circuit can comprise memory for capturing raw data stream or a data stream generated by the signal processing circuit (e.g., a conditioned data stream or a derived data stream). In such a case, in operation, collected data residing in the installed memory circuit can be transmitted to and either displayed in or stored in a ported unit, for later collection and/or analysis at a remote data repository. For example, a memory stick (jump drive) can be used to transfer data to a remote data repository.

The data retrieval circuit 30 can comprise (additionally or alternatively to the data storage circuit) data display circuitry 34 such as a light (e.g., an light-emitting diode (LED)) for indicating a status of a fluid under test) or such as a readout (e.g., an LED readout display) or such as a graphical user interface (e.g., computer monitor).

Likewise, in any of the aforementioned and/or following mentioned approaches and embodiments, referring again to 3A through 3B, the data retrieval circuitry 30 can comprise one or more modules for retrieving data—whether raw data or processed data. Generally, the data retrieval circuit 30 can comprise one or more circuits (or circuit modules), including a data storage circuit 32, a data display circuitry 34 and/or a data transmission circuitry 36. The data retrieval circuit 30 can be in electrical communication with the sensing element directly, or alternatively, via a signal processing circuit 20 that processes (e.g., amplifies, biases, converts, etc.) raw data coming from the sensing element.

With further reference to FIGS. 3C, the data storage circuit 32 can typically comprise: signal input circuitry 32a (e.g., for receiving raw data or a raw data stream from the sensing element, and/or for receiving conditioned data or a conditioned data stream from one or more data conditioning circuits 24, and/or for receiving derived data or a derived data stream from one or more data derivation circuits 26); a data storage media 32b (e.g., such as non-volatile memory (e.g., ROM, PROM, EE-PROM, FLASH memory etc.); and, signal output circuitry 32c (e.g., for outputting a stored data or stored data stream to another circuit module (e.g., to a data derivation circuit and/or to a data transmission circuit and/or to a data display circuit).

Data display circuit 34 as shown in FIG. 3C can configured to be effective for displaying data associated with one or more properties of a fluid, or for displaying a status of the fluid, where such status is based on data associated with a property of the fluid. Hence, data display circuit 34 can include a display device, and can typically comprise: signal input circuitry 34a (e.g., for receiving raw data or a raw data stream from the sensing element, and/or for receiving conditioned data or a conditioned data stream from one or more signal conditioning circuits 24, and/or for receiving derived data or a derived data stream from one or more data derivation circuits 26, and/or for receiving stored data or stored data stream from one or more data storage circuits 32); a data-display memory 34b (e.g., such as non-volatile memory (e.g., ROM, PROM, EEPROM, FLASH memory, etc., or random access memory (RAM), in either case typically for temporarily storing a data or data stream to-be-displayed); a microprocessor circuit 34c (e.g., for processing/modifying data, such as stored, to-be-displayed data); a visual display circuit 34d (e.g., digital computer monitor or screen; e.g., a status light such as a LED status light, e.g., a printer, e.g., an analog meter, e.g., a digital meter, e.g., a printer, e.g., a data-logging display device, e.g., preferably in some embodiments a graphical user interface, etc.); and, signal output circuitry 34e (e.g., for outputting a stored data or stored data stream—such as to another circuit module (e.g., to a data derivation circuit and/or to a data transmission circuit and/or to a data display circuit).

Data transmission circuit 36 as shown in 3C can be configured to be effective for transmitting data originating from the sensing element. Specifically, for example, the data transmission circuit 36 can include: signal input circuitry 36a (e.g., for receiving raw data or a raw data stream from the sensing element, and/or for receiving conditioned data or a conditioned data stream from one or more data conditioning circuits 24, and/or for receiving derived data or a derived data stream from one or more data derivation circuits 26, and/or for receiving stored data or stored data stream from one or more data storage circuits 32); an optional microprocessor circuit 36b (e.g., for processing/modifying data, such as stored, to-be-transmitted data, and/or for controlling data transmission protocols); transmission protocol circuitry 36c (e.g., for effecting and coordinating communication protocols, such as for example a hard-wired interface circuit (e.g., TCP/IP, 4-20 mA, 0-5V, digital output, etc.), or a wireless communication circuit involving an electromagnetic radiation (e.g., such as radio frequency (RF) short range communication protocols (e.g., Bluetooth™, WiFi-IEEE Standard 80211 et seq., radio modem), land-based packet relay protocols, satellite-based packet relay protocols, cellular telephone, fiber optic, microwave, ultra-violet and/or infrared protocols), or a wireless communication circuit involving magnetic fields (e.g., magnetic induction circuits); and signal output circuitry 36d (e.g., for outputting a transmission of stored data or stored data stream—such as to another circuit module (e.g., to a data derivation circuit and/or to a data storage circuit and/or to a data display circuit).

Data transmission is particularly preferred using a data transmission circuit 36 in connection with a ported sensor subassembly that comprises a signal-processing memory and the data transmission circuit. Where the signal-processing memory comprises user-defined data, such data can be configured to be accessible to the data transmission circuit for communicating the user-defined data from the ported sensor subassembly to the fluid system or to a remote data repository. In another preferred approach, the ported sensor subassembly can comprise a data transmission circuit for communicating data associated with one or more properties of the fluid from ported sensor subassembly to the fluid system or to a remote data repository. In another method, the ported sensor subassembly can comprise a data storage media accessible for storing data associated with one or more properties of the fluid, and in combination therewith, a data transmission circuit for communicating stored data from the data storage media to the fluidic system or to a remote data repository, in either case preferably using a wireless communication protocol.

In any event, preferably, generated data is stored (e.g., in memory), displayed (e.g., in a graphical user interface or other display device) or (meaning additionally or alternatively) transmitted (e.g., using hard-wired or wireless communications protocols) using the data retrieval circuit of the interfaced sensor. Although listed and represented in the figures in a particular (e.g., linear) order, the invention is not limited to use of such circuit modules in any particular order or configuration, and a person of ordinary skill in the art can determine a suitable circuit design for a particular fluidic system and a particular sensor, in view of the general and specific teaching provided herein.

With reference to FIG. 3D, illustrating a particularly preferred embodiment, the signal processing circuit 20 includes a signal conditioning circuit 24 that comprises (or in some embodiments consists essentially of) an amplifier circuit comprising one or more amplifiers or one or more preamplifiers, effective for or configured for amplifying one or more input signals received from one or both of the mechanical resonator 40 or the additional sensing elements 51. The sensor 10 of this embodiment preferably further comprises at least a data retrieval circuit 30, but most preferably comprises both a signal processing circuit 20 and a data retrieval circuit 30. This embodiment further comprise, an installed memory media, preferably such as a signal-processing memory as an accessible portion of a signal conditioning circuit 24 (not shown) and/or as an accessible portion of a data derivation circuit 26 (as shown) and/or as data storage circuit 32 (not shown). In a preferred approach, for example, the memory media can comprise electronic data storage media, such as non-volatile memory (e.g., ROM, PROM, EE-PROM, FLASH memory etc.), and can typically be pre-loaded with and/or accessible for loading user-defined data (e.g., calibration data, correlation data, data defining approximated fluid properties) as well as pre-loaded and/or accessible for loading user defined data that is system-specific information and/or sensing-element specific information, in each case such as an identifying indicia. The signal processing circuit 20 of this embodiment can further comprise (either as installed circuitry or as a ported circuitry subassembly) an optional signal activation circuit 22, a signal conditioning circuit 24 and a data derivation circuit 26, wherein the data derivation circuit 26 comprises microprocessor circuitry 26c configured for processing data originating from the mechanical resonators 40 and/or the additional sensing elements 51 such as additional temperature sensing elements in conjunction with user-defined data (e.g., calibration data) accessible from the installed memory media. The data retrieval circuit 30 of the sensor 10 of this particularly preferred embodiment preferably comprises, at least a data storage circuit 32 and preferably also either or both of a data display circuit 34 or a data transmission circuit 36.

The particular location of the signal processing circuitry 20 and/or data retrieval circuitry 30 of the installed sensor 40 is not critical. In some embodiments (e.g., in applications involving high-temperature and/or flammable fluids), it may be advantageous to provide the preinstalled circuitry 20, 30 external to the fluidic system (e.g., fixedly mounted on a surface of barrier 110 opposing the fluid-side surface of the barrier 110), and in electrical communication with one or more of the resonators 40 of sensor 10. In other embodiments the circuitry 20, 30 can be mounted on the fluid-side surface of the barrier 110.

Sensing Operations

The sensor can be advantageously applied to sense the fluid by collecting data, and typically a data stream that is fluid dependent, and that can be processed to identify and evaluate particular fluid property characteristics. The methods and systems and apparatus of the invention can be used to monitor fluid systems for various purposes. The inventions can be advantageously used, for example, to monitor fluids in any of the following field applications: materials or process research, materials or process development, materials or process quality assurance (QA), process monitoring/evaluation, process control, and service applications involving any of the foregoing.

As described above in connection with the generally preferred approaches and systems, the sensor is interfaced with one or more fluid systems. The sensor is operational for monitoring a property of a fluid within the fluid system. The fluid property can be monitored in real time, in near real time, or in time-delayed modes of operation. Further details of preferred fluid systems, fluids, properties, sensors and monitoring, including specific methodology approaches and apparatus features thereof are described herein (above and below), and each of the herein-described details are specifically considered in various combinations and permutations with the generally described aspects in this subsection of the specification.

In any of the aforementioned and/or following-mentioned approaches and embodiments, the signal processing circuitry can comprise one or more circuit modules for processing data originating from the resonators 40 (generally, directly or indirectly). The signal processing circuitry can comprise each such circuit module alone (i.e., individually) or in various combinations and permutations. The data being processed can be raw data (previously unprocessed data) typically coming either directly from the sensing element or from a data storage media (i.e., data memory circuitry) that captured the data directly from the sensing element. Alternatively, the data being processed by one or more circuit modules of the signal processing circuit can be previously processed data (e.g., from another module thereof).

Active/Passive Sensing

Regardless of the particular configuration for the interfaced sensor, the fluid is sensed, actively or passively, using the interfaced sensor during a first sensing period to generate data associated with one or more properties of the fluid. In passive sensing mode of operation, the flexural resonator sensing element is displaced by the fluid to generate a signal (e.g., such signal being generated by piezoelectric material of sensing element, with appropriate electrodes), without application of an electronic input stimulus to the flexural resonator. In an active sensing mode of operation, an electronic stimulus (e.g., input signal having a voltage and/or frequency) is provided to the flexural resonator sensing element to initiate (via piezoelectric properties) a mechanical response in the sensing element such that at least a portion of the sensing surface of resonator displaces at least a portion of the fluid. The mechanical response is fluid dependent, and the extent of that dependence can be measured electronically, as is known in the art. With further reference to FIGS. 3A through 3C, a signal activation circuit 22 can comprise, for an active sensing mode of operation, a signal input circuitry 22a (e.g., for receiving a data or a data stream or instructions on active sensing signals) one or more user-defined or user-selectable signal generators, such as a frequency generator circuitry 22b, and/or such as a voltage spike generator circuitry 22c, and in each case, e.g., for providing an electronic stimulus to the sensing element, in an active sensing configuration; and signal output circuitry 22d.

In a preferred operation involving an active sensing mode, a stimulus signal (e.g., such as a variable frequency signal or a spike signal) can be intermittently or continuously generated and provided to the sensing element. A property-influenced signal, such as a frequency response, is returned from the sensing element. The return signal (e.g., frequency response) can be conditioned and components of the signal (e.g., frequency response) can be detected. The method can further includes converting the frequency response to digital form, such that the digital form is representative of the frequency response received from the sensing element. Then, first calibration variables can be fetched from a memory. As used herein, the term "fetch" should be understood to include any method or technique used for obtaining data from a memory device. Depending on the particular type of memory, the addressing will be tailored to allow access of the particular stored data of interest. The first calibration variables can define physical characteristics of the sensor or sensing element. Second calibration variables can also be fetched from memory. The second calibration variables define characteristics of the sensor or sensing element in a known fluid. The digital form is then processed when the sensing element is in the fluid under-test, and the processing uses the fetched first and second calibration variables to implement a fitting algorithm to produce data that relates to the fluid properties or fluid characteristics of the fluid under-test.

In some embodiments involving an active sensing mode and using a mechanical resonator sensing element (such as a flexural resonator sensing element), it may be preferably to employ an active sensing mode of operation involving an input stimulus signal having a frequency of not more than about 1 MHz, and preferably not more than about 500 kHz, and preferably not more than about 200 kHz, and most preferably not more than about 100 kHz. In some embodiments, even lower frequencies can be employed in the operation of the mechanical resonator sensing element, including for example frequencies of not more than about 75 kHz. Specific operational ranges include frequencies ranging from about 1 kHz to about 1 MHz, preferably from about 1 kHz to about 500 kHz, preferably from about 1 kHz to about 200 kHz, preferably from about 1 kHz to about 100 kHz, preferably from about 1 kHz to about 75 kHz, more preferably from about 1 kHz to about 50 kHz, more preferably still from about 5 kHz to about 40 kHz, even more preferably from about 10 kHz to about 30 kHz and most preferably from about 20 kHz to about 35 kHz. In such embodiments, it may be preferably to provide an input stimulus signal that has a frequency that varies over time. In such embodiments, it may be preferably to provide two or more cycles of varying a frequency over time over a predetermined range of frequencies, and preferably over a frequency range that includes the resonant frequency for the flexural resonator sensing element. Such frequency sweeping offers operational advantages that are known in the art.

In a preferred operation involving a passive sensing mode, the mechanical resonators such as a flexural resonator, interacts with the fluid to generate a property-influenced signal. The signal from the sensing element is intermittently or continuously observed and/or retrieved by the signal processing circuit. The signal can be conditioned and components of the signal (e.g., frequency response, voltage, etc.) can be detected. The method can further include converting the response to digital form, such that the digital form is representative of the signal received from the sensor. Then, as above in the active mode, first and/or second calibration variables can be fetched from a memory. The first calibration variables can define physical characteristics of the sensor or sensing element. Second calibration variables can also be fetched from memory. The second calibration variables can define characteristics of the sensor or sensing element in a known fluid. The digital form can then processed when the sensing element is in the fluid under-test, and the processing uses the fetched first and second calibration variables to implement a fitting algorithm to produce data that relates to the fluid properties or fluid characteristics of the fluid under-test.

In preferred embodiments, one or more circuit modules of the signal processing circuit and/or the data retrieval circuit can be implemented and realized as an application specific integrated circuit (ASIC). See, for example, above-referenced U.S. Ser. No. 10/394,543 entitled "Application Specific Integrated Circuitry For Controlling Analysis For a Fluid" filed on Mar. 21, 2003 by Kolosov et al., and PCT Application. No. PCT/US04/008555 entitled "Application Specific Integrated Circuitry For Controlling Analysis For a Fluid" filed on Mar. 19, 2004 by Kolosov et al. Particularly preferred circuit configurations are described below, but should be considered generally applicable to each approach and embodiment of the inventions described herein.

User-Defined Data (e.g., Calibration)

Generally relevant to each of the methods, systems and apparatus of the inventions, user-defined data such as calibration data, correlation data, signal-conditioning data can be employed as part of a signal processing circuit (e.g., signal conditioning and/or data derivation circuitry). Likewise, additionally or alternatively, identifying indicia such as barcodes, electronic signatures (e.g., 64-bit serial numbers) can be used to identify one or more of: particular fluid systems, particular locations within a fluid system; particular fluid types; particular sensors; and/or particular sensing elements (including sensing element types (e.g., tuning fork flexural resonator), sensing element lot numbers for a set of co-manufactured sensing elements, and specific particular individual sensing elements). Such user-defined identifying indicia can be particularly useful in combination with user-defined calibration, correlation and/or signal conditioning data since such data can be specific to the fluid system, the location, the fluid type; the sensor (type or individual sensor) and/or the particular sensing elements (including sensing element types (e.g., tuning fork flexural resonator), sensing element lot numbers for a set of co-manufactured sensing elements, and specific particular individual sensing elements). The user-defined data can be fluid-property (e.g., temperature dependent), and therefore, there can be interaction between one or more sensing elements (e.g., temperature sensing element) and a user-defined data (e.g., calibration data) for a particular fluid in a particular system using a particular resonator. The user-defined data can generally be pre-defined data or can be concurrently-defined data, and the defining can be done by a person and/or by a computer.

The level of specificity of any particular user-defined data to any particular fluidic system, fluid, sensor or sensor element will depend on the particular user-application, the property of interest, the sensor type, the required degree of accuracy, etc.

In a preferred methods, apparatus and systems, in which a flexural resonator sensing element is employed alone or in conjunction with one or more other systems, it is preferable to have accessible user-defined calibration data that includes at least (i) flexural resonator sensing element-specific (e.g., calibration) data, as well as (ii) application-specific (e.g., fluid type) data (e.g., calibration data). It is also preferable to have specific user-defined identifying indicia.

In general, there are several approaches for managing a network of interfaced sensors across multiple fluidic systems, where each sensor/system may require its own specific signal conditioning data (e.g., offset information) and/or its own specific user-defined input to a data derivation circuitry (e.g. calibration data or correlation data or approximate fluid property values, etc.).

In one approach, discussed for example in connection with FIG. 3D, each installed sensing element can have a locally installed signal-processing memory module for storing the required user-defined data. A person porting a ported sensor subassembly can then initiate a sensing operation (or retrieve an accumulated or stored data stream) using signal processing circuitry of the ported sensor subassembly. The ported signal processing circuitry can communicate with the locally-installed signal-processing memory module to get the user-defined data (e.g. calibration data) specific for sensing the fluid at that location of that fluid system using that particular sensing element.

In an additional or alternative approach, a signal-processing memory module for storing user-defined data for data derivation can be included within the ported sensor subassembly. In some embodiments, the data can be a standard data set with a set of varying corrections for particular sensors or fluids or fluid conditions. Some sort of identifying indicia is preferably available at the site of the interfaced sensor for identifying it with particularity. In this instance, a person porting a ported sensor subassembly can then initiate a sensing operation (or retrieve an accumulated or stored data stream) by first interrogating (querying) the identifying indicia, and then using the read identifying indicia within the ported sensor subassembly to obtain the relevant user-defined data set for the fluid at that location of that fluid system using that particular sensing element.

Other variations on this approach can likewise be beneficially applied.

Flexural Resonator Sensing Elements and Operation Thereof

Figure 4A:
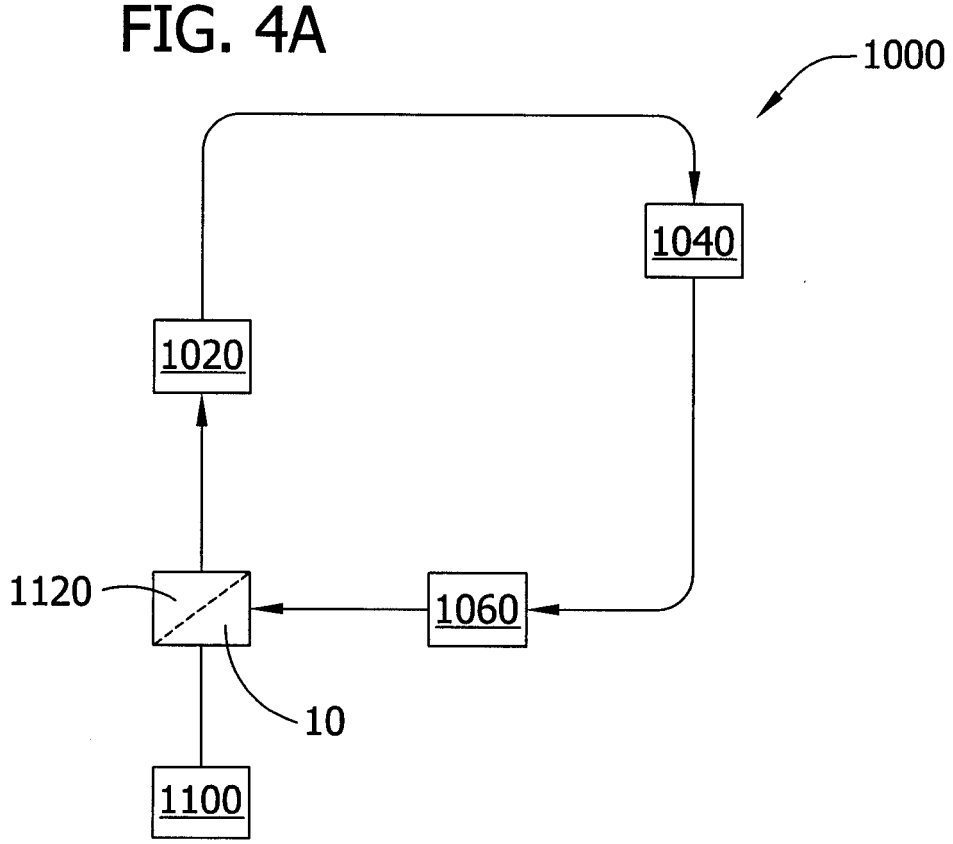
FIGS. 4A through 4I are schematic representations of a fluid system (FIG. 4A) and of several configurations for flexural resonator sensing elements (FIG. 4B through 4I).

As seen in FIG. 4A, one embodiment involves the incorporation of a sensor 10 according to the present invention into a fluid system 1000, such as an environmental control system, that includes one or more unit operation devices 1020, 1040, 1060 such as a compressor, an expansion valve, a condenser and an evaporator through which a thermal change fluid can be cycled via one or more passages, such as in a conduit. Other components may also be employed as desired, such as one or more suitable pumps, a filter, a dryer, a suitable flow cell, or a combination of two or more thereof. Likewise, any of the above components may be omitted from a system of the present invention. Suitable valving and process monitoring instrumentation may also be employed in the fluid system 1000.

One or more of the sensors 10 according to the present invention is adapted for permanent or temporary placement with multiple resonators 40 positioned within one of the system components or between one of the system components. For example one or more resonators 40 may be situated between various unit operation devices 1020, 1040, 1060. Likewise, one or more resonators 40 may additionally or alternatively be incorporated in another component, such as a conduit, coil, filter, nozzle, dryer, pump, valve or other component, or positioned upstream or downstream therefrom. The resonators may be located in the flow path of the fluid (e.g., in a conduit), a headspace or both. In a particular embodiment, the sensor resonators 40 are included along with (and optionally integrated therewith) a condition monitoring device such as a temperature measurement device, a pressure measurement device, a mass flow meter, or combinations of two or more of such devices. Without limitation, an example of a combined pressure and temperature sensor is discussed in U.S. Pat. No. 5,586,445 (incorporated by reference).

Sensing in accordance with the present invention is particularly attractive for evaluating one or more of properties of the fluid, such as the level of a fluid (e.g., indicative of a system leak, a blockage in the system, or the like), the superheat condition of a fluid (e.g., the level of superheat), subcooling of a fluid, concentration of a desired component (e.g., refrigerant) in the fluid, or the presence or absence or concentration of an undesired component (e.g., contaminants) in the fluid. In particular, the sensor is effectively employed to monitor (continuously or periodically) small changes in conditions of the fluid, such as viscosity, density, viscosity/density product, dielectric constant, conductivity or combinations of two or more thereof, which are indicative of a change of one or more of the above-noted properties, or of a change in state of the fluid or the presence of contaminants, and to output the results thereof.

Optionally, the mechanical resonators can be in signaling communication with a processing unit 1100 (which may include a user interface) for controlling operation of the fluid system. The processing unit 1110 may be microprocessor integrated with the sensor 10, for example, as part of the signal processing circuitry as described above. The processing unit 1100 optionally can optionally also be in signaling communication with a condition monitoring device 1120 (shown as part of an integrated assembly with the sensor 10. Thus, data obtained from the sensor 10 may be processed along with other data to assist in monitoring and establishing operating conditions of the fluid system.

Thus, for example, in one aspect of the present embodiment, the sensor 10 according to the present invention is employed to monitor at least one property of a fluid (e.g., the simultaneous monitoring of viscosity and density). Data generated from the sensor, along with other data (e.g., temperature, pressure, flow rate, or combinations thereof), for example, from the condition monitoring device 1120, can be sent to the processing unit 1100. From the data provided, the processing unit 1110, which typically will be programmed with a suitable algorithm, will process the data. In a process control embodiment, the processing unit can effect least one operation of the fluid system selected from switching a subsystem of the fluid system (e.g., a unit operation device 1020, 1040, 1060) or one or more components thereof between an "on" or "off" state, shutting or opening a valve in the fluid system, changing a flow rate of the fluid, changing a pressure of the fluid, changing the operating speed or condition of one or more components of the fluid system, or otherwise controlling operation of the fluid system or a component thereof, providing a visual output signal, providing an audible output signal, or a combination thereof.

It will be appreciated that the above configuration of FIG. 4A permits the use of one or more modes of active sensing operations, such as excitation at one or more frequencies around resonance frequency of the resonator, or the time decay of oscillation after an electrical or mechanical impulse (e.g., a voltage spike). Passive operations can include, for example, observing passive oscillations due to ambient noise, vibrations, electromagnetic interference, etc.

The monitoring of fluid properties according to the invention may be performed under normal operating conditions of the machine into which the present sensor is placed. The present invention is particularly advantageous in that it operable over a broad range of temperatures. Thus, in one specific aspect, it is contemplated that the monitoring step occurs at a temperature below −40° C. or possibly the monitoring step occurs at a temperature above 400° C. Generally the monitoring will occur between these extremes.

During or following monitoring, the response of the sensor may be compared against another value, such as a prior response of the resonator, a response of another resonator located elsewhere in the system, a known reference value for the fluid, or a combination of two or more such comparisons. The observed response may be stored in memory or otherwise recorded. Data about a particular fluid can be stored in memory of a suitable processor, which can be retrieved in response to a triggering event, such as inputting by a technician or reading of a fluid type by an optical detector, such as a bar code scanner.

As the fluid property changes over time, analysis can be made and the response compared with those of the fresh fluid. The identification of a difference between responses may then be used as a trigger or other output signal for communicating with diagnostics hardware, which provides an audible or visual signal to the operator. Additionally or alternatively, such a signal may be outputted to a remote telemetry device, such as one located external of the system. Thus, as with any of the embodiments herein a "wireless" communications system can be employed, pursuant to which a signal that is outputted may be a radiofrequency signal or another electromagnetic signal. Comparison against reference values from the original fluid is not the only approach for generating a communication to a user about the fluid condition. For example, certain expected values may be pre-programmed into a device, which then compares the real-time values obtained. Alternatively, such comparisons are not made, but rather upon obtaining a certain threshold response, an output signal is generated for triggering a user notification, for triggering a system control unit to alter one or more functions of the system or a combination thereof. It is also contemplated that a sensor in a controlled fluid sample may be employed as an internal reference.

It is also possible that the response obtained from the monitoring is stored in a memory, with or without communicating the response to the user. In this manner, a service technician can later retrieve the data for analysis.

Figure 4B:
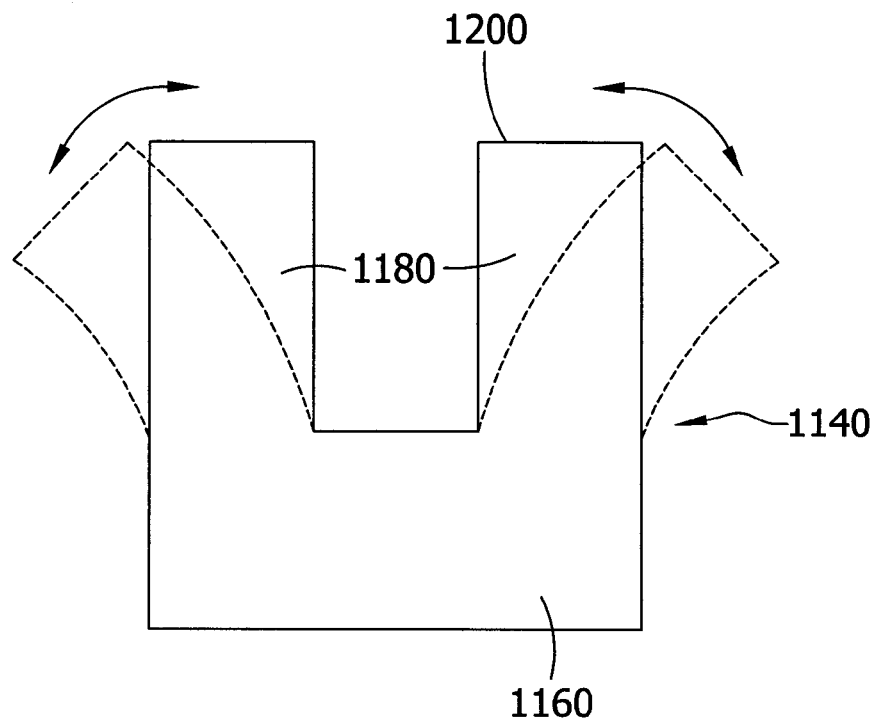

Turning now to FIG. 4B there is shown an illustration of one preferred resonator element 1140 in accordance with the present invention. The resonator element 1140 preferably includes a base 1160 that has at least two tines 1180 having tips 1200 that project from the base. The shape of the tines and their orientation relative to each other on the base may vary depending upon the particular needs of an application. For example, in one embodiment, the tines 1180 are generally parallel to each other. In another embodiment the tines diverge away from each other as the tips are approached. In yet another embodiment, the tines converge toward each other. The tines may be generally straight, curved, or a combination thereof. They may be of constant cross sectional thickness, of varying thickness progressing along the length of the tine, or a combination thereof.

Resonator sensing element(s) are suitably positioned in an element holder. Alternatively, the elements (with or without a holder) may be securably attached to a wall or barrier or other surface defining one of the fluid systems or passages into which it is placed. In yet another embodiment, the element is suitably suspended within a passage such as by a wire, screen, or other suitable structure.

Element holders may partially or fully surround the sensing elements as desired. Suitable protective shields, baffles, sheath or the like may also be employed, as desired, for protection of the elements from sudden changes in fluid flow rate, pressure or velocity, electrical or mechanical bombardment or the like to help locate an element relative to a fluid or combinations thereof. It should be appreciated that resonator elements may be fabricated from suitable materials or in a suitable manner such that may be employed to be re-useable or disposable.

Examples of approaches to materials combinations, or the packaging of sensing elements that may be employed in accordance with the present invention are disclosed, without limitation in commonly-owned U.S. Provisional Application Ser. Nos. 60/456,767 and 60/456,517 (both filed Mar. 21, 2003) (and incorporated by reference). Thus, one particular approach contemplates affixing a sensing element having a exposed sensing surface to a platform, wherein a spaced relationship is created between the exposed sensing surface and the platform. A suitable protective layer may be applied to cover the platform and/or the sensing element while maintaining an exposed sensing surface. The latter exposed sensing surface may be prepared by the use of a consumable protective layer (e.g., a polymer, starch, wax, salt or other dissolvable crystal, low melting point metal, a photoresist, or another sacrificial material) that is used to block the exposed sensing surface prior to applying the protective layer.

A plurality of the same type or different types of resonators of resonators can be used in combination. For example, a low frequency resonator may be employed with a high frequency resonator. In this manner, it may be possible to obtain a wider range of responses for a given sample.

The size of the sensing elements, especially mechanical resonator sensing elements such as flexural resonator sensing elements is not critical to the invention. In some applications, however, it should be appreciated that one advantage of the present invention is the ability to fabricate a very small sensor using the present resonators. For example, one preferred resonator has its largest dimension smaller than about 2 cm, and more preferably smaller than about 1 cm. One resonator has length and width dimensions of about 3 mm by 8 mm, and possibly as small as about 1 mm by 2.5 mm. Geometry of the resonator may be varied as desired also. For example, the aspect ratio of tines of the tuning forks, or geometrical factors of other resonators can be optimized in order to achieve better sensitivity to the properties of the gas phase, liquid phase or its particular components (e.g., a lubricant). For example, the aspect ratio of a tuning fork tine may range from about 30:1 to about 1:1. More specifically, it may range from about 15:1 to about 2:1.

Figure 4C:
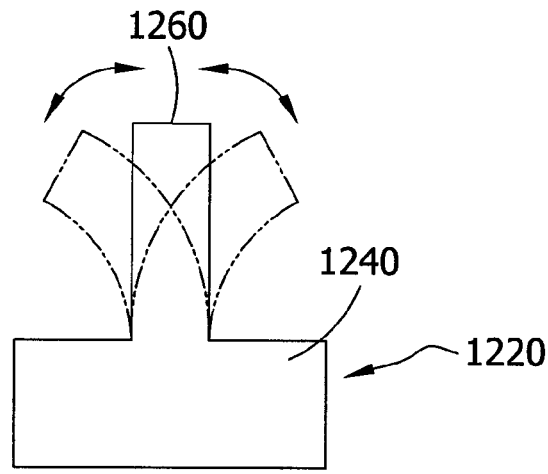
Figure 4D:
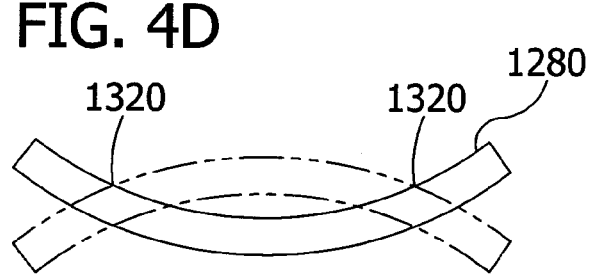
Figure 4E:
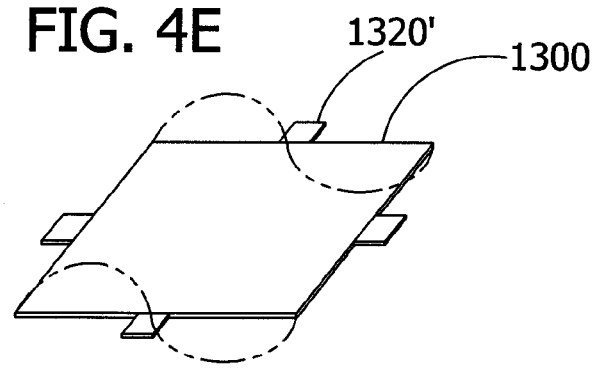
Figure 4F:
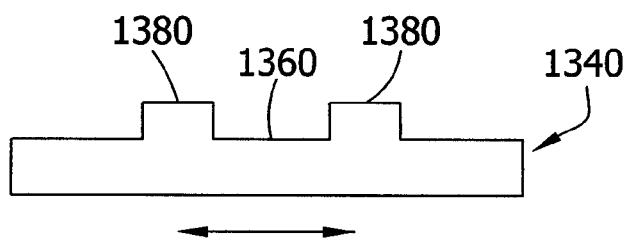

It is thus seen that a preferred resonator is configured for movement of a body through a fluid. Thus, for example, as seen in FIG. 4B, the resonator may have a base and one or a plurality of tines projecting from the base. It is preferred in one aspect that any tine has at least one free tip that is capable of displacement in a fluid relative to the base. FIG. 4C illustrates a cantilever 1220 having a base 1240 and a free tip 1260. Other possible structures, seen in FIGS. 4D and 4E contemplate having a disk 1280, a plate 1300 or the like that is adapted so that one portion of it is displaceable relative to one or more variable or fixed locations 1320 (1320'). As seen in FIG. 4F, in yet another embodiment a resonator 1340 is contemplated in which a shear surface 1360 of the resonator has one or more projections 1380 of a suitable configuration, in order that the resonator may be operated in shear while still functioning consistent with the flexural or torsional resonators of the present invention, by passing the projections through a fluid.

Figure 4G:
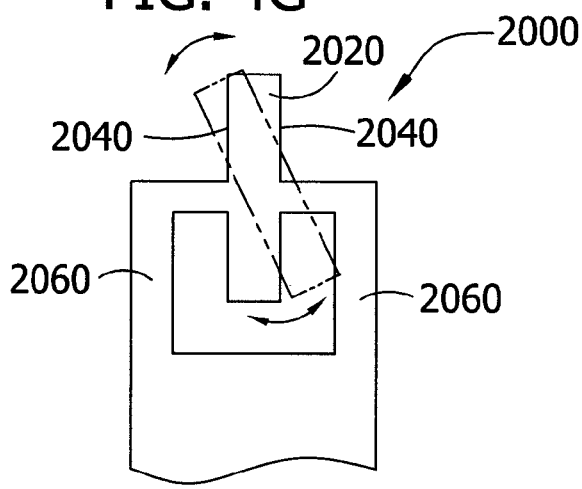
Figure 4H:
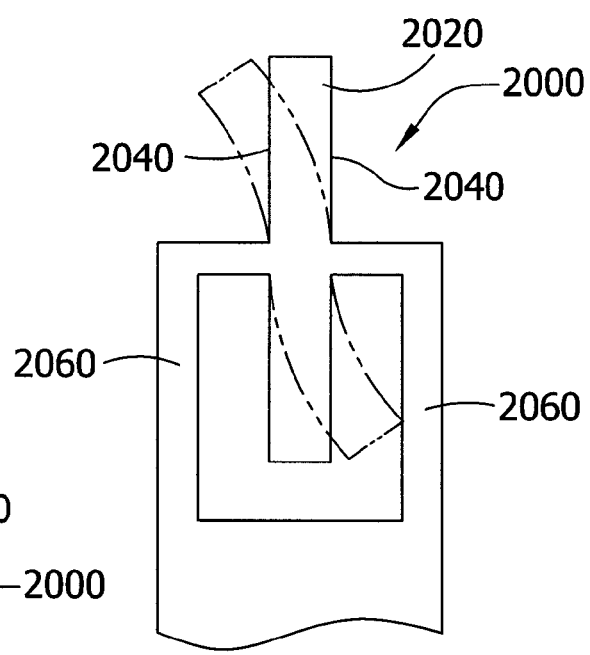
Figure 4I:
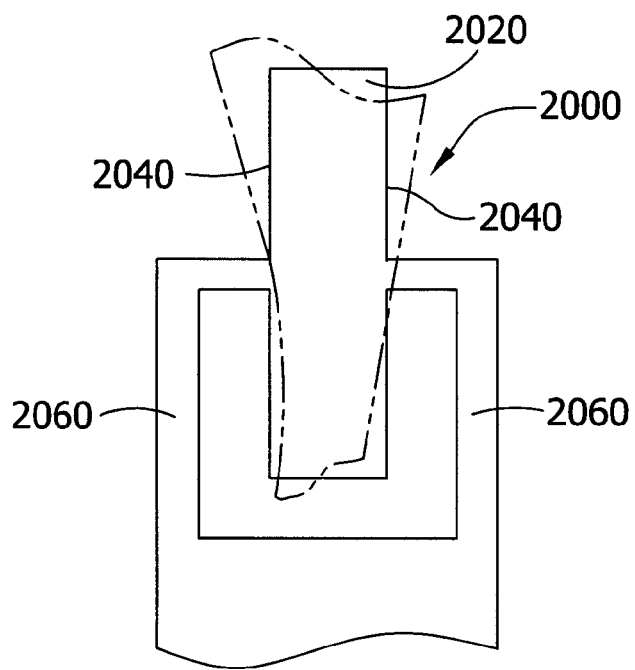

In still other embodiments, and referring to FIG. 4G, 4H and 4I, it is contemplated that a resonator 2000 may include an elongated member 2020 supported on its sides 2040 by a pair of arms 2060. As shown respectively in FIGS. 4G through 4I, the elongated member may be configured to oscillate side-to-side, back and forth, in twisting motions or combinations thereof.

The flexural resonator, such as the embodiment of FIG. 4B, may be constructed as a monolithic device. Yet another structure of the present invention contemplates the employment of a laminate or other multi-layer body that employs dissimilar materials in each of at least a first layer and a second layer, or a laminate comprised of layers of piezoelectric material of different orientations or configurations. According to this approach, upon subjecting one or more of the layers to a stimulus such as temperature change, an electrical signal or other stimulus, one of the materials will respond differently from the other and the differences in responses will, in turn, result in the flexure of the resonator. In yet another embodiment, it is contemplated that plural resonators can be assembled together with an electrode at least partially sandwiched therebetween. In this manner, it may be possible to further protect electrodes from harsh conditions, while still achieving the desired flexure. One specific example might include a two or more lithium niobate or quartz tuning forks joined together with a gold electrode therebetween. Other configurations (e.g., an H-shaped resonator) and material combinations may be employed as well, as disclosed in U.S. Provisional Application Ser. Nos. 60/456,767 and 60/456,517 (both filed Mar. 21, 2003), incorporated by reference.

As can be seen, the selection of the specific resonator material, structure, or other characteristic commonly varies depending upon the specific intended application. Nonetheless, it is preferred that for each application, the resonator is such that one or a combination of the following features (and in one highly preferred embodiment, a combination of all features) is present: a coating, if placed upon the resonator in a thickness greater than about 0.1 micron, will not substantially detract from resonance performance; the resonator is operable and is operated at a frequency of less than about 1 MHz, and more preferably less than about 100 kHz; the resonator is substantially resistant to contaminants proximate to the sensor surface; the resonator operates to displace at least a portion of its body through a fluid; or the resonator responses are capable of de-convolution for measuring one or more individual properties of density, viscosity, viscosity/density product, conductivity or dielectric constant.

The resonator may be uncoated or coated or otherwise surface treated over some or all of its exterior surface. A preferred coating is a metal (e.g., a conductive metal similar to what may be employed for electrodes for the sensor, such as silver, gold, copper, aluminum or the like), plastic, ceramic or composite thereof, in which the coating material is substantially resistant to degradation from the fluid to which it is to be exposed or to surface build-up, over a broad temperature range. For example, one preferred embodiment, contemplates the employment of a base resonator material and a performance-tuning material. Among the preferred characteristics of the resonators of the present invention is the base material is generally thermally stable. For example, in one preferred embodiment, the material exhibits a dielectric constant that is substantially constant over a temperature range of about 0° C. to about 100° C., more preferably about −20° C. to about 150° C., and still more preferably about −40° C. to about 200° C. For example, it is contemplated that a preferred material exhibits stability to a temperature of at least about 300° C., and more preferably at least about 450° C. In another aspect, the dielectric constant of the performance-tuning material preferably is greater than that of quartz alone, such as by a factor of 5 or more, more preferably by a factor of 10 or more and still more preferably by a factor of 20 or more.

Figure 5A:
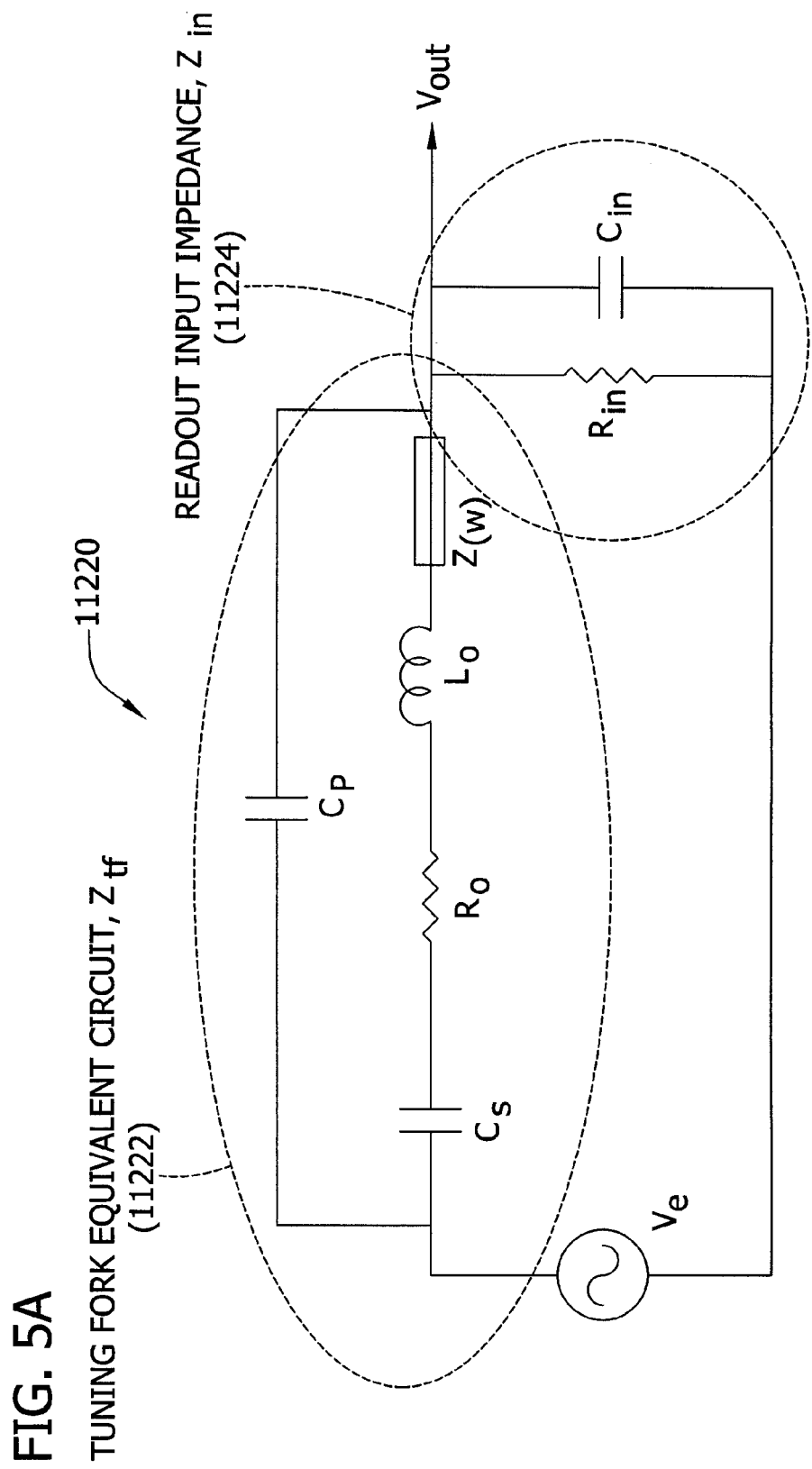

FIG. 5A illustrates a circuit diagram 11220 for a tuning fork equivalent circuit 11222 and a read-out input impedance circuit 11224. The frequency generator is coupled to the tuning fork equivalent circuit 11222 to a parallel connection of a capacitance Cp as well as a series connection of a capacitor Cs, a resistor Ro, an inductor Lo, and an equivalent impedance $Z(\omega)$. The read-out impedance circuit includes a parallel resistor Rin and a capacitor Cin. The output voltage is thus represented as Vout.

The equations shown in FIG. 5B can define the equivalent circuit. In equation (2), the Vout of the equivalent circuit is defined. In equations (3) and (4), the impedance Zin and Ztf are derived. Equation (5) illustrates the resulting impedance over frequency $Z(\omega)$. As can be appreciated, the voltage Vout, graphed verses the frequency $Z(\omega)$, necessitates the determination of several variables.

The variables are defined in equation (1) of FIG. 5B. In operation, the tuning fork's frequency response near the resonance is used to determine the variables that will define the characteristics of the fluid-under-test. The algorithm that will be used to determine the target fluid under-test characteristic parameters will require knowledge of data obtained during calibration of a tuning fork. In addition to access to calibration data, the algorithm will also utilize a data fitting process to merge approximated variables of the target fluid under-test, to the actual variable characteristics (i.e., density, viscosity, dielectric constant) for the fluid under-test.

In the circuit, it is assumed that Cs, Ro, Lo are equivalent characteristics of a preferred resonator in a vacuum, Cp is the equivalent parallel capacitance in a particular fluid under-test, $\rho$ is the fluid density, $\eta$ is fluid viscosity, $\omega$ is oscillation frequency. Cp is a function of k, as shown in equations (6) through (10). The constant "k" is, in one embodiment, a function of the tuning fork's geometry, and in one embodiment, defines the slope of a curve plotting (Cpmeasured, Cpcal, and Cpvaccum) verses ($\epsilon$measured, $\epsilon$cal, and $\epsilon$vacuum), respectively. In a physical sense, the constant "k" is a function of the tuning fork's geometry, the geometry of the tuning fork's electrode geometry, the tuning fork's packaging (e.g., holder) geometry, the material properties of the tuning fork, or a combination of any of the above factors. The resulting value of Cp will be used to determine the dielectric constant $\epsilon$ as shown by the equations.

Further, it can be appreciated that that viscosity and density can be de-convoluted based on the equations defined in FIG. 5C. For some sensors, the value of Cp measured is typically on the order of about 1 to 3 orders of magnitude greater than the value of Cs. Accordingly, in order to improve the ability to measure $Z(\omega)$, desirably trimming circuitry is employed as part of or in association with the signal conditioner, such as a trimming circuits. In order to more efficiently process the signal being received from the tuning fork, the signal 232 is signal conditioned to eliminate or reduce the signal offset and thus, increase the dynamic range of the signal produced by the tuning fork. Thus, the data being analyzed can be more accurately processed.

FIGS. 6A through 6C and 7A through 7D represent one set of preferred approaches and embodiments for realizing a signal processing circuitry for a flexural resonator sensor. In particular, the described approaches and embodiments are considered in the context of an interfaced sensor applied with a fluid system within an engine, and in particular, in combination with an control unit (CU), which directs overall control of multiple aspects of engine operation. This should be understood as being an example demonstrating an application and manner of realizing the present inventions, and should not be limiting on the inventions described herein.

Figure 6A:
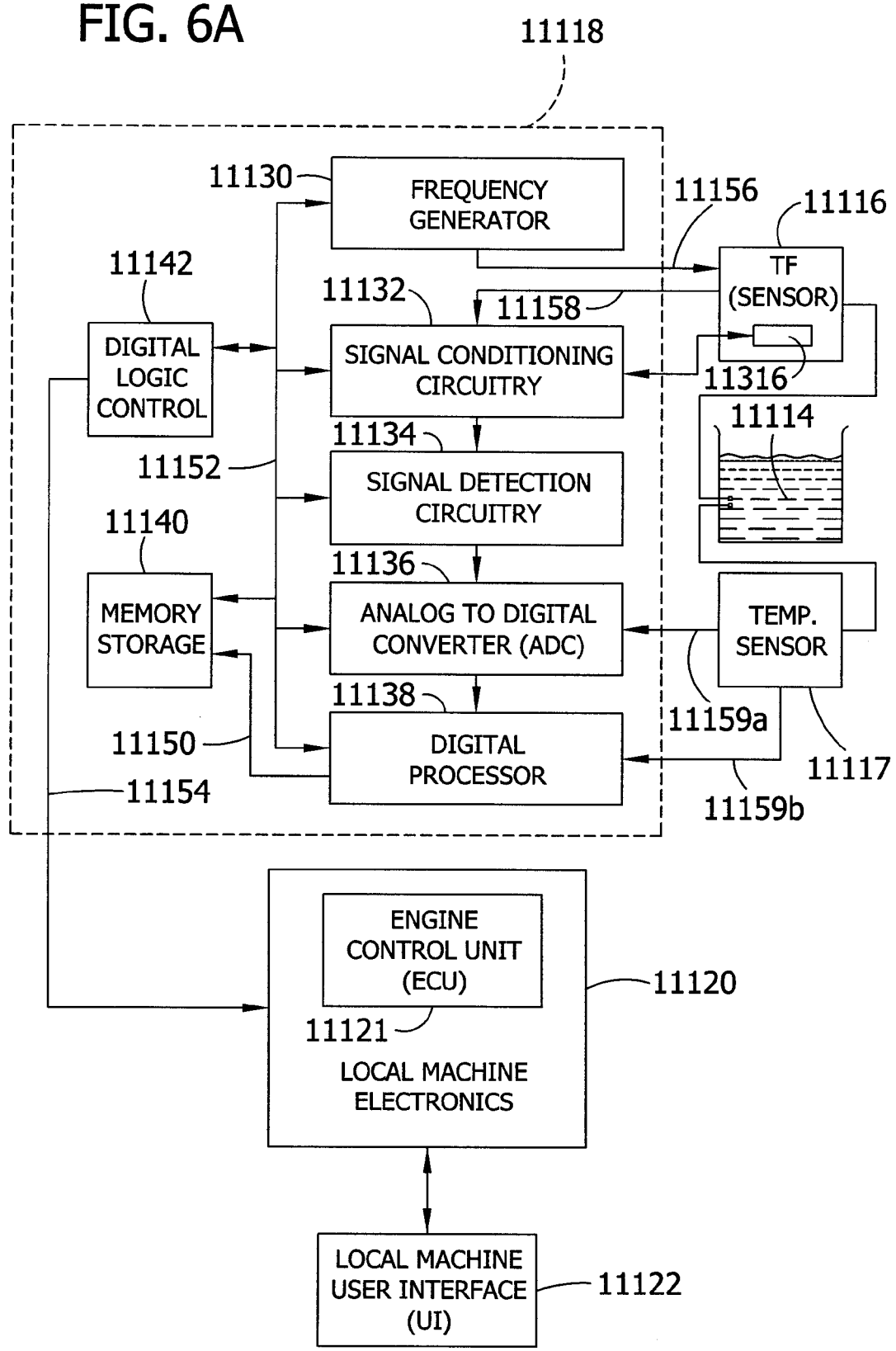

FIG. 6A illustrates a block diagram of the circuit formed, for example, in an application specific integrated circuit (ASIC) 11118 and its components, as an example of a signal processing circuit. The ASIC 11118 is designed to provide stimulus to the tuning fork 116 and receive and process data to provide information regarding the characteristics of a fluid under-test. In one embodiment, the ASIC will include a frequency generator 11130 that is configured to provide a frequency stimulus to the tuning fork 11116 by way of communication line 11156. The generated frequency is preferably a variable frequency input signal, such as a sinusoidal wave or square wave, that sweeps over a predetermined frequency range. The sweeping range will preferably include the resonance frequency range of the sensor. Preferably, the frequency is less than 100 kHz, and more preferably, is in the range of about 5 kHz and about 50 kHz, and most preferably, is in the range of about 20 kHz to about 35 kHz.

The tuning fork response over the frequency range is then monitored to determine the physical and electrical properties of the fluid under-test. The response from the tuning fork 11116 is provided to a signal conditioning circuitry block 11132, by way of a communication line 11158. In one preferred embodiment, the tuning fork 11116 will also include a capacitor 11316, which will be described in greater detail below. The capacitor 11316 is also coupled to the signal conditioning circuitry 11132. The signal conditioning circuitry 11132 is provided to receive the analog form of the signal from the tuning fork 11116 and condition it so that more efficient signal processing may be performed before further processing.

The signal conditioning circuitry 11132 will receive the analog output from the tuning fork 11116, and is designed to substantially eliminate or reduce signal offsets, thus increasing the dynamic range of the signal that is to be further processed. In this manner, further processing can concentrate on the signal itself as opposed to data associated with the signal offset.

Signal detection circuitry (SDC) 11134 is also provided, and it is coupled to the signal conditioning circuitry 11132. Signal detection circuitry 11134 will include, in one embodiment, a root mean squared (RMS) to DC converter, that is designed to generate a DC output (i.e., amplitude only) equal to the RMS value of any input received from the signal conditioning circuitry 11132. The functional operation of a RMS-to-DC converter is well known to those skilled in the art. In another embodiment, the signal detection circuitry 11134 may be provided in the form of a synchronous detector. As is well known, synchronous detectors are designed to identify a signal's phase and amplitude when preprocessing of an analog signal is desired in order to convert the analog signal into digital form. Once the signal detection circuitry block 11134 processes the signal received from the signal conditioning circuitry 11132, the signal detection circuitry 11134 will pass the data to an analog-to-digital converter (ADC) 11136. The analog-to-digital converter 11136 will preferably operate at a sampling rate of up to 10 kHz while using a 10-bit resolution. The analog-to-digital converter (ADC) can, of course, take on any sampling rate and provide any bit resolution desired so long as the data received from the signal detection circuitry is processed into digital form.

The ADC 11136 will also receive information from the temperature sensor 11117 to make adjustments to the conversion from the analog form to the digital form in view of the actual temperature in the fluid under-test 11114. In an alternative embodiment, the temperature sensor 11117 can be omitted, however, the temperature sensor 11117 will assist in providing data that will expedite the processing by the ASIC 11118.

The digital signal provided by the analog-to-digital converter 11136 is then forwarded to a digital processor 11138. The digital processor 11138 is coupled to memory storage 11140 by way of a data bus 11150 and a logic bus 11152. Logic bus 11152 is also shown connected to each of the frequency generator 11130, the signal conditioning circuitry 11132, the signal detection circuitry 11134, and the analog-to-digital converter 11136. A digital logic control 11142 is directly coupled to the logic bus 11152. The digital logic control 11142 will thus communicate with each of the blocks of the ASIC 11118 to synchronize when operation should take place by each one of the blocks. Returning to the digital processor 11138, the digital processor 11138 will receive the sensed data from the tuning fork 11116 in digital form, and then apply an algorithm to identify characteristics of the fluid under-test 11114.

The algorithm is designed to quickly identify variables that are unknown in the fluid undertest. The unknown variables may include, for example, density, viscosity, the dielectric constant, and other variables (if needed, and depending on the fluid). Further, depending on the fluid undertest 11114 being examined, the memory storage 11140 will have a database of known variables for specific calibrated tuning forks. In one embodiment, the memory storage 11140 may also hold variables for approximation of variables associated with particular fluids. In another embodiment, the memory storage 11140 will store serial numbers (or some type of identifier) to allow particular sets of data to be associated with particular tuning forks. In such a serial number configuration, the storage memory can hold unique data sets for a multitude of unique tuning forks. When a tuning fork is sold, for example, the purchaser need only input its assigned serial number into an interface, and the data set associated for that tuning fork will be used during operation. From time to time, it may be necessary to upload additional data sets to the storage memory 11140, as new tuning forks (with unique serial numbers) are manufactured.

The process for using variable data from prior calibrations and from fluids that may closely resemble the fluid undertest, is described in greater detail below. In general, however, the digital processor 11138 may quickly access the data from the memory storage 11140, and digitally process an algorithm that will generate and output variables that define the fluid under-test 11114.

The digital processor then communicates through the digital logic control 11142 and communication line 11154, the identified variables that characterize the fluid undertest 11114 to the local machine (or process monitoring and/or control) electronics 11120 (or some recipient computer, either locally or over a network). In one embodiment, the local machine or process electronics 11120 includes a control unit (CU) 11121, that directly receives the data from the digital logic control 11142 through signal 11154. The control unit 11121 then receives those data and, in accordance with its programmed routines, provides feedback to the local machine or process/user interface 11122.

For example, the control unit 11121, may set a different threshold for when the fluid undertest 11114 has degraded or otherwise changed. For example, different processes, and therefore, different control units for each process, may define a particular viscosity, density and dielectric constant (or one or a combination thereof) that may be indicative of the system under study. However, this programmable threshold level setting ordinarily differs among different processes and/or different process plants. Thus, the control unit 11121 provides to the local machine or process/user interface 11122 the appropriate signals depending on the programming of the particular process/plant in which the control unit 11121 is resident.

The ASIC 11118 has been shown to include a number of component blocks, however, it should be understood that not all components need be included in the ASIC as is discussed below. In this example, the digital processor 11138 may be physically outside of the ASIC 11118, and represented in terms of a general processor. If the digital processor 11138 is located outside of the ASIC 11118, the digital logic control 142 takes the form of glue logic that is able to communicate between the digital processor 11138 that is located outside of the ASIC 11118, and the remaining components within the ASIC 11118. If the processor 11138 is outside of the ASIC, the processor is still in communication with the control unit 11121.

Figure 6B:
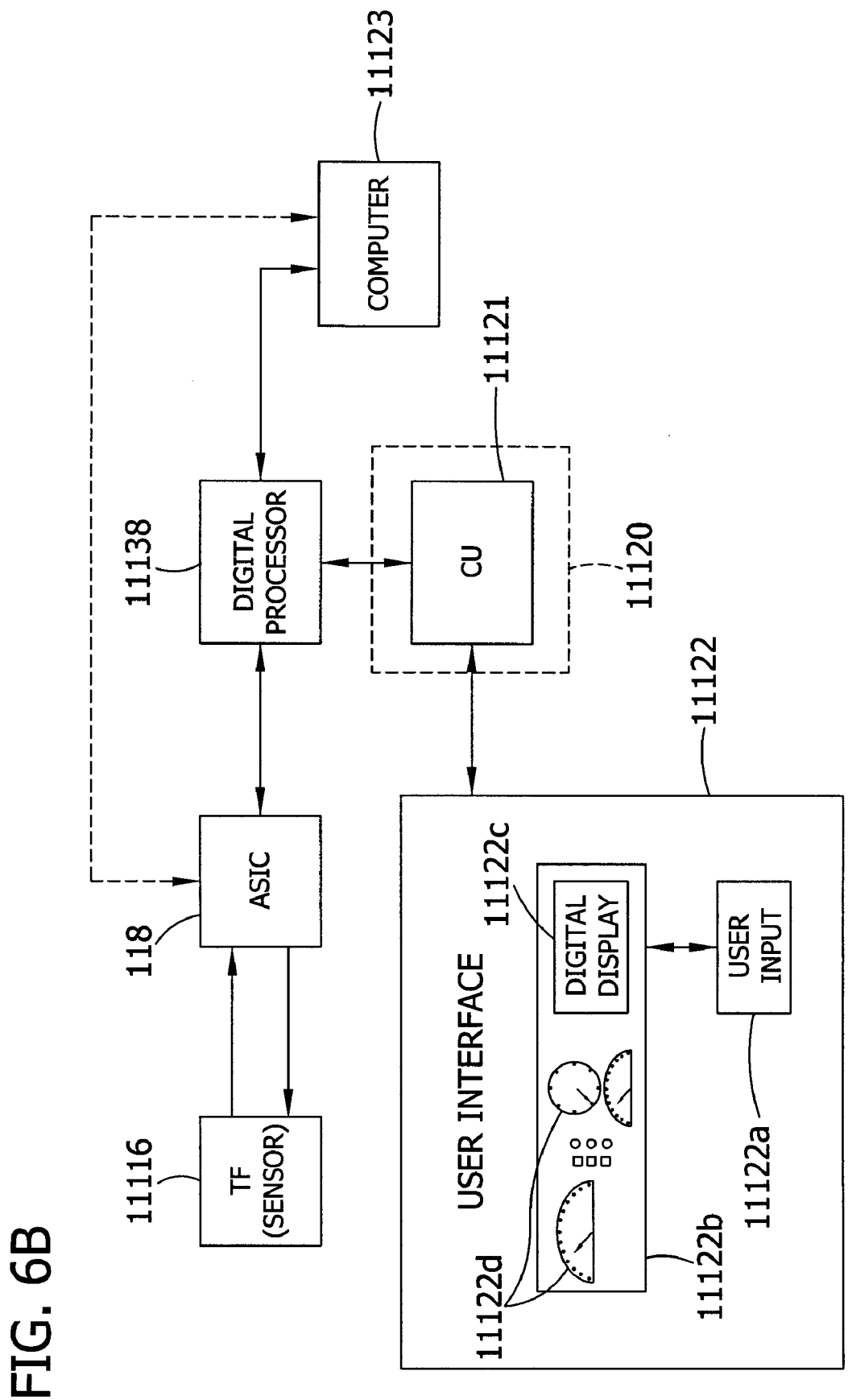

FIG. 6B illustrates an example in which the digital processor 11138 is outside of the ASIC 11118. In such an embodiment, the digital processor 11138 may be integrated into a printed circuit board that is alongside of the ASIC 11118, or on a separate printed circuit board. In either case, the ASIC 11118 is in communication with the tuning fork 11116 to provide stimulus and to process the received analog signals from the tuning fork 11116. The ASIC receives the analog signals coming from the tuning fork 11116 and converts them to a digital form before being passed to the digital processor 11138.

If the digital processor 138 is outside of the ASIC 11118, the digital processor 11138 is still able to communicate with the control unit 11121 of the local machine or process electronics 11120. The control unit 11121 communicates with the local machine or process/user interface 11122. In this example, the user interface may include a user display 11122*b*. The user display 11122*b* may include analog and digital indicators 11122*d*. The analog and digital indicators 11122*d* may indicate the qualities of the fluid under-test and can be displayed in terms of a gauge reading to indicate to the user when the fluid under-test has degraded or needs to be changed, or where a control variable needs to be adjusted to bring a target variable back to a control set point or adjusted set point.

In another embodiment, the user display 11122*b* may include a digital display 11122*c* (e.g., monitor) that may provide a digital output or display of the condition of the fluid under test to the user through an appropriate graphical user interface (GUI). The user interface 11122 may also include a user input 11122*a*. The user input 11112*a* may be an electronic interface that allows a service technician, for example, to provide updated calibration information for a tuning fork that is inserted in a particular system, or provide adjusted approximations for new fluids that may be used in connection with a particular system.

By way of the user input 11122*a*, a service technician or process operator may input new data to the ASIC 11118 through the control unit 11121. As mentioned above, the ASIC 11118 includes a memory storage 11140 for storing calibration data, and in some embodiments, storing approximated characteristics for fluids that may undergo sensing by tuning fork 11116.

FIG. 6C illustrates another detailed block diagram of the ASIC 11118, in accordance with certain embodiments of the present invention. In this example, the ASIC 11118 shows a number of blocks that may be integrated into or kept out of, the ASIC 11118. Blocks that may be kept outside of the ASIC include blocks 11175. As a high level diagram, the tuning fork 11116 is connected to an analog I/O 11160. The analog I/O is representative of blocks 11132, 11134, and 11136, in FIG. 6A above. The analog I/O block 11160 therefore performs signal conditioning and conversion of the data received from the tuning fork 11116.

Frequency generator 11130, as discussed above, provides the variable frequency input signal to the tuning fork 11116 through the analog I/O 160. Glue logic 11162 is provided to integrate together the various circuit blocks that reside on the ASIC 11118. As is well known, glue logic includes signaling lines, interfacing signals, timing signals, and any other circuitry that is needed to provide inputs and outputs to and from the chip that defines the ASIC 11118. All such glue logic is standard and is well known in the art. The ASIC 11118 further includes user defined data (ROM) 11140. As mentioned above, the user-defined data 11140 may include calibration data, as well as approximated variable data for particular fluids that may become fluids undertest. The user defined data to be stored in this memory can come from any source. For example, the data may be obtained from a fluid manufacturer, a tuning fork manufacturer, a contractor party, etc. Still further, the data may be obtained in the form of a data stream, a database or over a network.

For example, FIGS. 6D and 6E provide exemplary data that may be stored within the user-defined data 11140'. As shown in FIG. 6D, a tuning fork 1.1 (designated as such to emphasize varieties in tuning forks) may provide calibration variables, as well as approximated fluid characteristics for a particular type of fluid. In the example of FIG. 6D, the selected fluid type 3 has approximated fluid characteristics for density, viscosity, and dielectric constant for a particular temperature, which is depicted in this figure to be 25° C. As used herein, the term "approximated fluid characteristics" represent starting point values of fluid characteristics before the fitting algorithm is started. Thus, the starting point values are initial values defined from experience, previous tests, or educated guesses. Consequently, the starting point values, in one embodiment, approximate the actual fluid characteristic values of the fluid undertest. In this manner, convergence to the actual fluid characteristics can be expedited.

In still another embodiment, it may be possible to start with the approximated fluid characteristics at some set of fixed values (which can be zero, for example). From each fixed value, the fitting algorithm can move the value until the actual fluid characteristic value is ascertained.

Continuing with the example, the approximated fluid characteristics for the same fluid type 3 may have different approximated fluid characteristics due to the rise in temperature to 40° C., as shown in FIG. 6E. The calibration variables are also updated to reflect the values for a particular temperature for the tuning fork 1.1. As new fluids types are used in connection with a fluidic system, it may be necessary to update the approximated fluid characteristics for the different temperature ranges so that the user-defined data can be updated in the ASIC 11118.

Referring back to FIG. 6C, a digital I/O 11140' is provided to interface with a computer 11123, and a test I/O interface 11164 is provided to enable testing of the ASIC 11118 during design simulation, during test bench testing, during pre-market release, and during field operation. The ASIC 11118 also includes a timer 11172 to provide coherent operation of the logic blocks contained in ASIC 11118. As mentioned above, the ROM block 11166, the RAM block 11168, the CPU core 11170, and the clock 11174, can optionally be included in the ASIC 11118 or removed and integrated outside of the ASIC 11118. The ROM 11166 includes programming instructions for circuit interfaces and functionality of the ASIC 11118, the RAM 11168 provides the CPU core 11170 with memory space to read and write data being processed by the CPU core 11170, and the clock 11174 provides the ASIC with proper signal alignment for the various signals being processed by the blocks of the ASIC 11118.

FIGS. 7A through 7D depict alternative configurations for various circuit modules of the ASIC 11118.

Downstream Data Processing

The methods and systems and apparatus of the invention can be used as described herein to monitor fluids in fluid systems to generate data associated with one or more properties of the fluids. The data generated can be used directly, for example, as described herein for status evaluation, fluid property logging, fluid property tracking, etc., among other uses. Such data can also be subsequently further processed for further subsequent uses (i.e., downstream) for various purposes. Such downstream processing of the data or data stream (represented for example by a signal or signal stream), typically but not necessarily in connection with other data from other independent sources, can be effectively applied to generate higher level information or knowledge based on the directly generated data, for example for purposes such as one or more of: process monitoring, process control (e.g., involving automated or manual control schemes, such as feedback or feed forward control schemes), fluid maintenance (e.g., fluid replacement (whole or partial), fluid enhancement (e.g., adding one more additives or removing one or more contaminants), fluid operating conditions (e.g., temperature, pressure, flowrate, etc.), predictive maintenance, materials or process research, materials or process development, quality control, fluid analysis, and especially maintenance or service applications involving any of the foregoing, among others.

Based on the descriptions set out hereinabove, it may be seen that mechanical resonators, and especially flexural resonators, may be used in the monitoring and control of industrial manufacturing and refining processes. It has been found that the resonators have further and highly advantageous applications in the evaluation and design of such processes, for example in the evaluation of the kinetics of a chemical or biological reaction. As in the case of a manufacturing process, the resonator is contacted with a fluid representative of the reaction, e.g., a fluid reaction medium in which the reaction is or has been conducted, a fluid comprising a source of a reactant for the reaction, a fluid comprising a catalyst or source of catalyst (e.g., a heterogeneous catalyst or homogeneous catalyst such as a phase transfer catalyst) for the reaction, a fluid comprising a product of the reaction, a fluid comprising a by-product of the reaction, a fluid that is separated from a fluid reaction medium during or after the reaction. Where the reaction is conducted in a liquid medium, the fluid with which the sensor is contacted may be, e.g., the liquid medium, a solution comprising a reactant and/or product of the reaction in the reaction medium, a dispersion comprising a reactant and/or a product of the reaction dispersed in the reaction medium, another liquid phase comprising a source of a reactant, a sink for removal of a reaction product, or a source of a phase transfer catalyst, a vapor phase evaporated from the liquid medium, another liquid phase resulting from a phase separation occurring during the course of the reaction, and a dispersion comprising another liquid phase. The sensor is stimulated while in contact with the fluid to be monitored, and the response of the resonator is monitored. Based on data thereby obtained, a kinetic parameter of the reaction may be derived. For example, the conversion of a reactant and/or the formation of a product and/or by-product may be monitored based on a change in the value of the density, viscosity, kinematic viscosity, or dielectric constant of said fluid. Thus, the rate constant for the reaction may be determined by the rate of change in the density, dielectric constant or viscosity. Based on either theoretical or empirical relationships, the composition of the reaction mass may be a known function of its viscosity, density, kinematic viscosity or dielectric constant either linear or non-linear. Based on the response of a mechanical resonator that is calibrated with such established relationships, in a reaction mass of known initial composition, the concentration of a reactant, product or by-product may be uniquely determined in real time from a material balance for the reaction, without the need for either on-line or off-line chemical analyses of samples. From the change in such concentrations as a function of time, e.g., from the rate of disappearance of a reactant or the rate of formation of a product or by-product, the instantaneous reaction rate may be determined at any time during the reaction. Based on the shape of the curve, the order of the reaction and kinetic rate constant can be determined.

To estimate the order of reaction, the reaction rate may be separately determined at two or more separate concentrations of the specified reactant in the fluid reaction medium. As described in Examples 8 to 10 hereinbelow, the order of the reaction may then be determined by a comparison of the determined reaction rates at the respective concentrations. For example, a logarithm of the rate of the reaction may be plotted vs. the corresponding logarithm of the concentration of the specified reactant; and the order of the reaction determined from slope of the plot so obtained. For such purposes it is preferred that the concentration(s) of other reactant(s) be substantially similar at the separate concentrations of the specified reactant at which the reaction rate is determined.

Once the order of the reaction is known, the kinetic rate constant may be estimated from the reaction rate equation:

$$-dc_A/dt = kc_A^a c_B^b$$

for the reaction:

$$A + B \rightarrow C$$

where:
$c_A$=the instantaneous concentration of reactant A
$c_B$=the instantaneous concentration of reactant B
a=the order of the reaction with respect to A
b=the order of the reaction with respect to B
t=time
k=the reaction rate constant Using this relationship, the determination of the rate constant may be based on the instantaneous rate at any given concentration of a reactant whose rate of disappearance is monitored, again applying the reaction material balance to determine the instantaneous concentrations of other reactants which appear as terms in the equation.

EXAMPLES

Experiments employing the methods and systems of the invention were performed for demonstrating use of mechanical resonator sensors in separation operations involving distillation and other unit operation.

Example 1

This example demonstrates the applicability of the methods and systems of the invention to a solvent switching operation. In the experimental set-up for this example, a mechanical resonator sensor was used, with a sensing surface of the mechanical resonator positioned in a process vessel.

In this example, neat ethyl acetate was switched over to neat n-heptane using a constant-volume distillation operation in a batch process vessel. Briefly, 100 mL of ethyl acetate was charged to a 250 mL round bottom 4-neck flask, equipped with a magnetic stirrer. A condenser and distillate receiver were connected in series to one neck of the flask. A thermocouple was placed into the flask via a separate second neck. A syringe pump, for continuous feed of n-heptane to the flask, was connected to the flask via a coring needle and septum through a third neck of the flask. Finally, a mechanical resonator sensor comprising a calibrated quartz tuning fork resonator was placed into the flask via the final neck, such that a sensing surface of the tuning fork resonator contacted the fluid (initially, neat ethyl acetate). Data acquisition was obtained using a computer connected to a communication board associated with the tuning fork resonator.

Once boiling visibly started, a heating mantle around the flask was set at constant power to maintain a constant distillation rate, and the syringe pump of n-heptane was set at a constant feed rate such that the volume in the distillation flask remained constant. Density, dielectric constant and viscosity were monitored by the mechanical resonator sensor comprising the tuning fork resonator, and these data were updated every 30 seconds. The distillation was stopped after 250 mL (i.e., 2.5 batch volumes) of heptane had been added.

Figure 8:
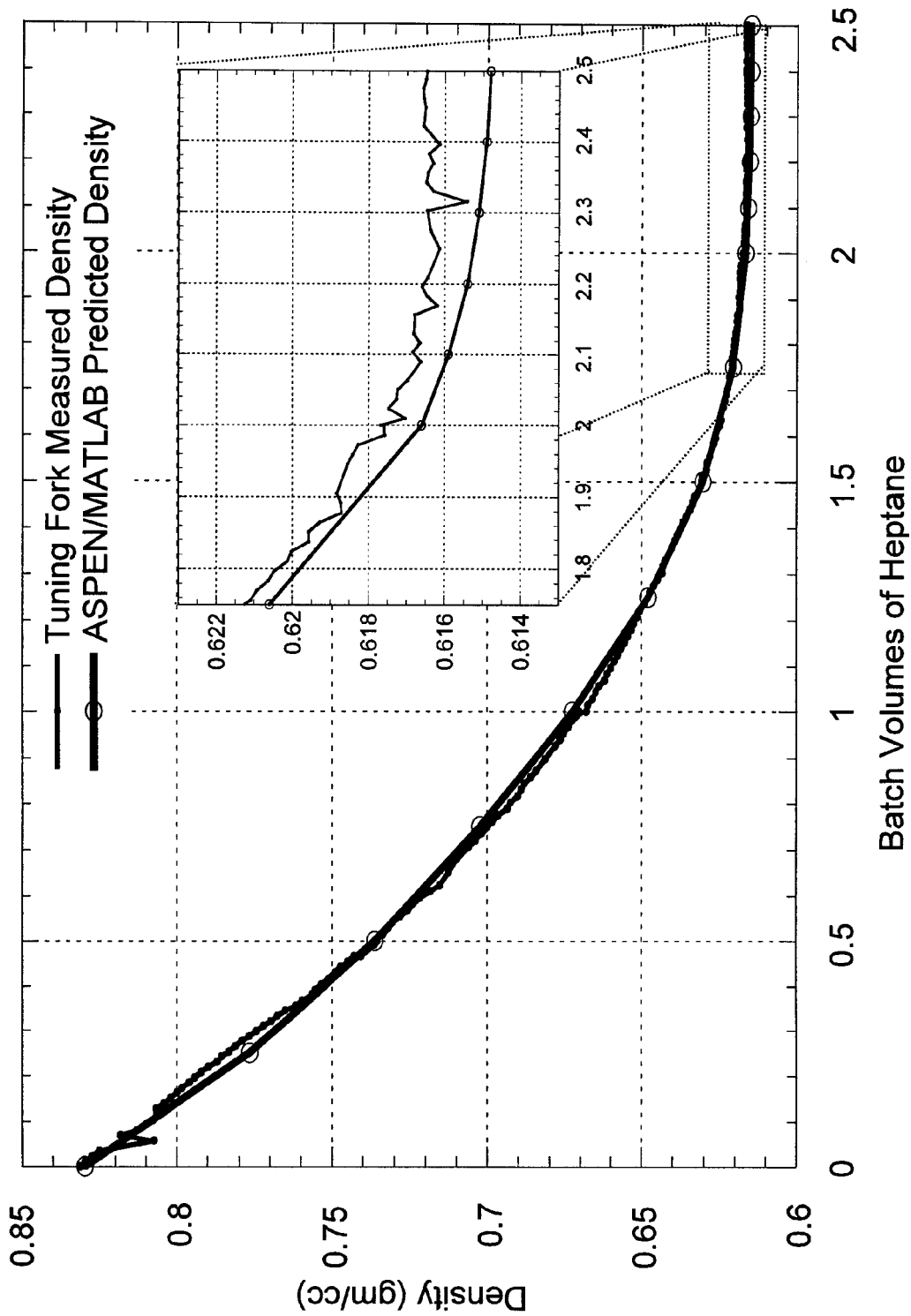
FIG. 8 is a plot illustrating the monitoring data for density (blue data, as illustrated) resulting from the solvent-switching experiment involving ethyl acetate and n-heptane, as described in Example 1, together with expected data values based on a computer simulation (ASPEN/METLAB), shown superimposed in FIG. 8 (red data, as illustrated). The data near the end-point is also shown, on a larger scale, in the insert plot of FIG. 8.

The monitored data for density are shown in FIG. 8 (blue data, as illustrated). The monitored data agreed well with expected data values, based on a computer simulation ASPEN/METLAB), also shown superimposed in FIG. 8 (red data, as illustrated). The data near the end-point is also shown, on a larger scale, in the insert plot of FIG. 8.

Samples for gas chromatograph (GC) analysis were removed at discrete intervals during the distillation experiment (for comparison purposes). These data are shown below, in Table 1-1. These data show that after 2.0 batch volumes of heptane had been added, about 0.1% by weight residual ethyl acetate was present in the flask, and that 2.5 batch volumes of heptane had been added, the GC revealed non-detectable residual ethyl acetate.

The monitored density data (FIG. 8A) corresponds with the GC data, as indicated by the relatively constant density profile measured after around 2.0 batch volumes of heptane had been added.

TABLE 1-1

Representative GC Results for Residual Ethyl Acetate

| Batch Volumes Heptane Added | Residual Ethyl Acetate (wt %) |
|---|---|
| 1.5 | 7.26 |
| 1.75 | 1.17 |
| 2 | 0.1 |
| 2.25 | 0.03 |
| 2.5 | ND |

Example 2

This example also demonstrates the applicability of the methods and systems of the invention to a solvent switching operation. The experimental set-up for this example used a mechanical resonator sensor, and simulated placement of the mechanical resonator downstream of a condenser, such as in a condenser discharge line, of a distillation system.

In this example, a solvent switch from THF to ethyl acetate was simulated by considering the suitability for measuring small amounts of THF in ethyl acetate (thereby effectively simulating residual amounts of THF that would be present near the end-point of the solvent switch). Specifically, ~20 ml ethyl acetate was provided in a scintillation vials. Different amounts of THF (0-5 wt %) were dissolved into the ~20 mL of ethyl acetate by shaking the scintillation vials. The vials were configured with a mechanical resonator sensor comprising a calibrated quartz tuning fork resonator, such that a sensing surface of the tuning fork resonator contacted the fluid. Data acquisition was obtained using a computer connected to a communication board associated with the tuning fork resonator. The mechanical resonator sensor having the quartz tuning fork resonator was used to measure the density, viscosity and dielectric constant of each of the resulting solution mixtures at ambient temperature and pressure conditions.

Figure 9:
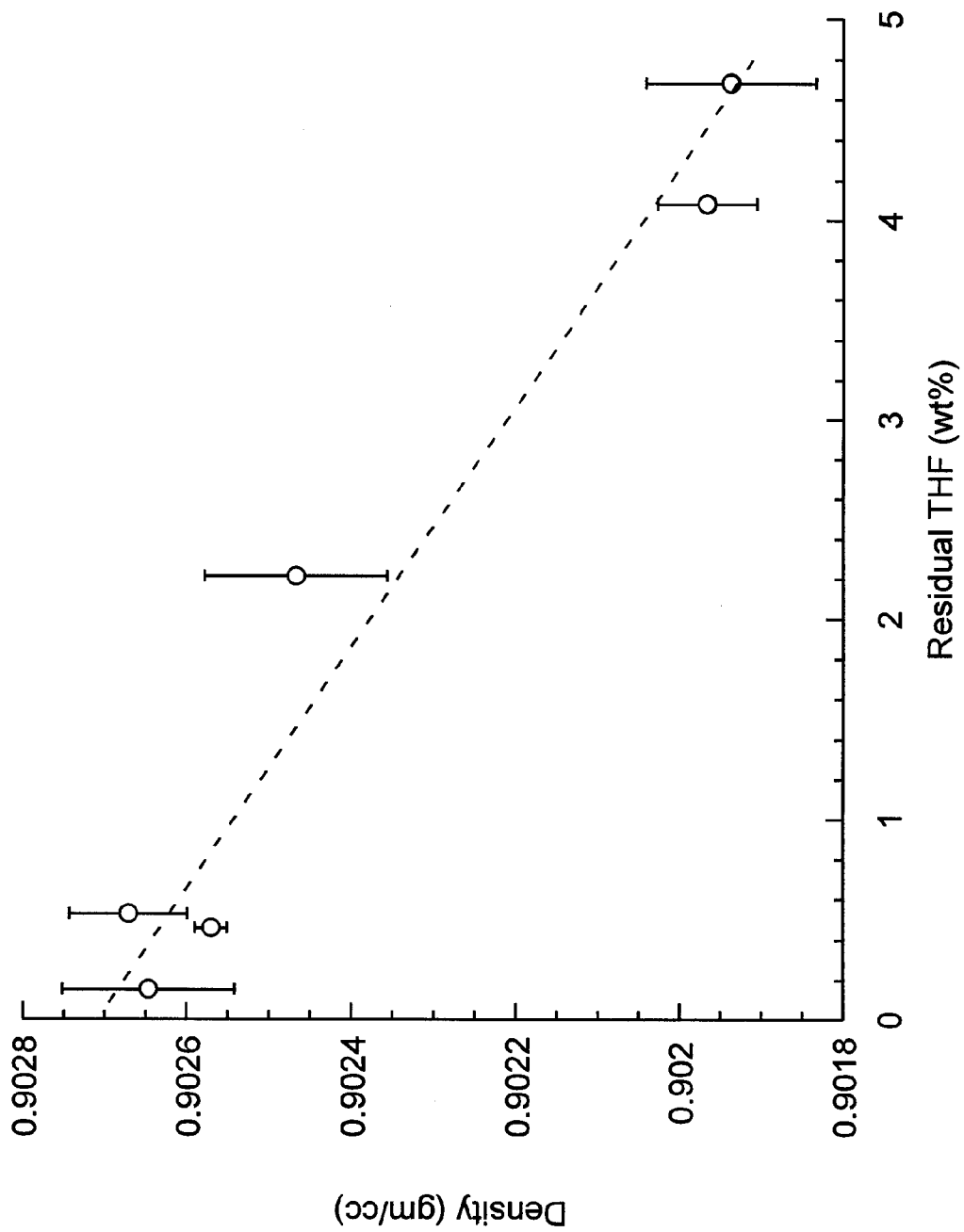
FIG. 9 is a plot illustrating the monitoring data for density at low residual amounts of THF in ethyl acetate, as described in Example 2.

The monitored data for density are shown in FIG. 9. These data show discernable differences in density at low residual amounts of THF, and thereby demonstrate that the mechanical resonator sensors can be suitably used in the methods and systems of the invention as applied toward solvent switching from THF to ethyl acetate.

Example 3

This example demonstrates the applicability of the methods and systems of the invention to a solvent switching operation involving a solution, in which the solute precipitates out of solution as a result of the solvent switch. This example also demonstrates the suitability of the methods and systems of the invention for monitoring a precipitation reaction.

In this example, the methods and set-up was the same as in Example 1, except that ~20 g of salicylic acid acetate (aspirin) was provided to the process vessel to form a solution of the salicylic acid acetate in the 100 ml ethyl acetate. The solution comprising ethyl acetate solvent was then switched over to a solution comprising n-heptane using a constant-volume distillation operation in a batch process vessel, substantially as described in connection with Example 1. The salicylic acid acetate precipitated out of solution after adding about 6.5 batch volumes of heptane.

Figure 10:
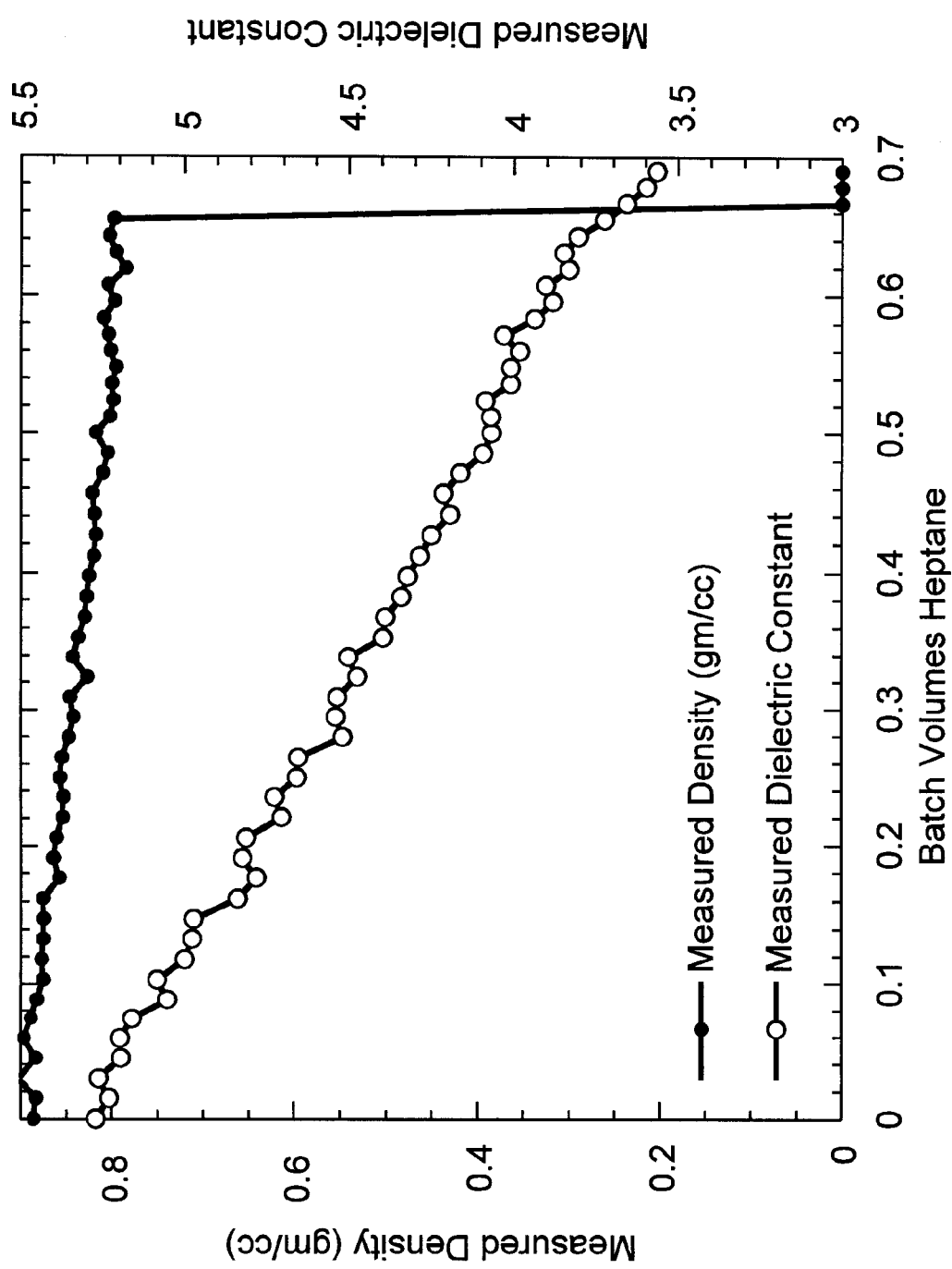
FIG. 10 is a plot illustrating the monitoring data for density (blue data) and dielectric (red data) resulting from an experiment involving a solvent switching operation, in which a solute precipitates out of solution as a result of the solvent switch, as described in Example 3.

The monitored data for density (blue data) and dielectric (red data) are shown in FIG. 10. The density data clearly shows the precipitation event, as reflected by the sudden decrease in solution density that occurred after about 6.5 batch volumes of heptane had been added. The dielectric data also shows discernable differences in dielectric constant throughout the experiment.

Example 4

This example demonstrates the applicability of the methods and systems of the invention to a solute concentration operation. The experimental set-up for this example used a mechanical resonator sensor, and simulated placement of the mechanical resonator in a process vessel during a concentration operation.

For this experiment, solutions comprising different known concentrations of salicylic acid acetate (aspirin) in ethyl acetate solvent were formed, by heating in a round bottom flask. The solutions with different concentrations of solute simulated a solution during different times of a distillation operation. The density, viscosity and dielectric constant were measured for each solution at 60° C. (+/−0.5C) using a mechanical resonator sensor comprising a quartz tuning fork resonator. A sensing surface of the tuning fork resonator contacted the fluid. Data acquisition was obtained using a computer connected to a communication board associated with the tuning fork resonator.

Figure 11:
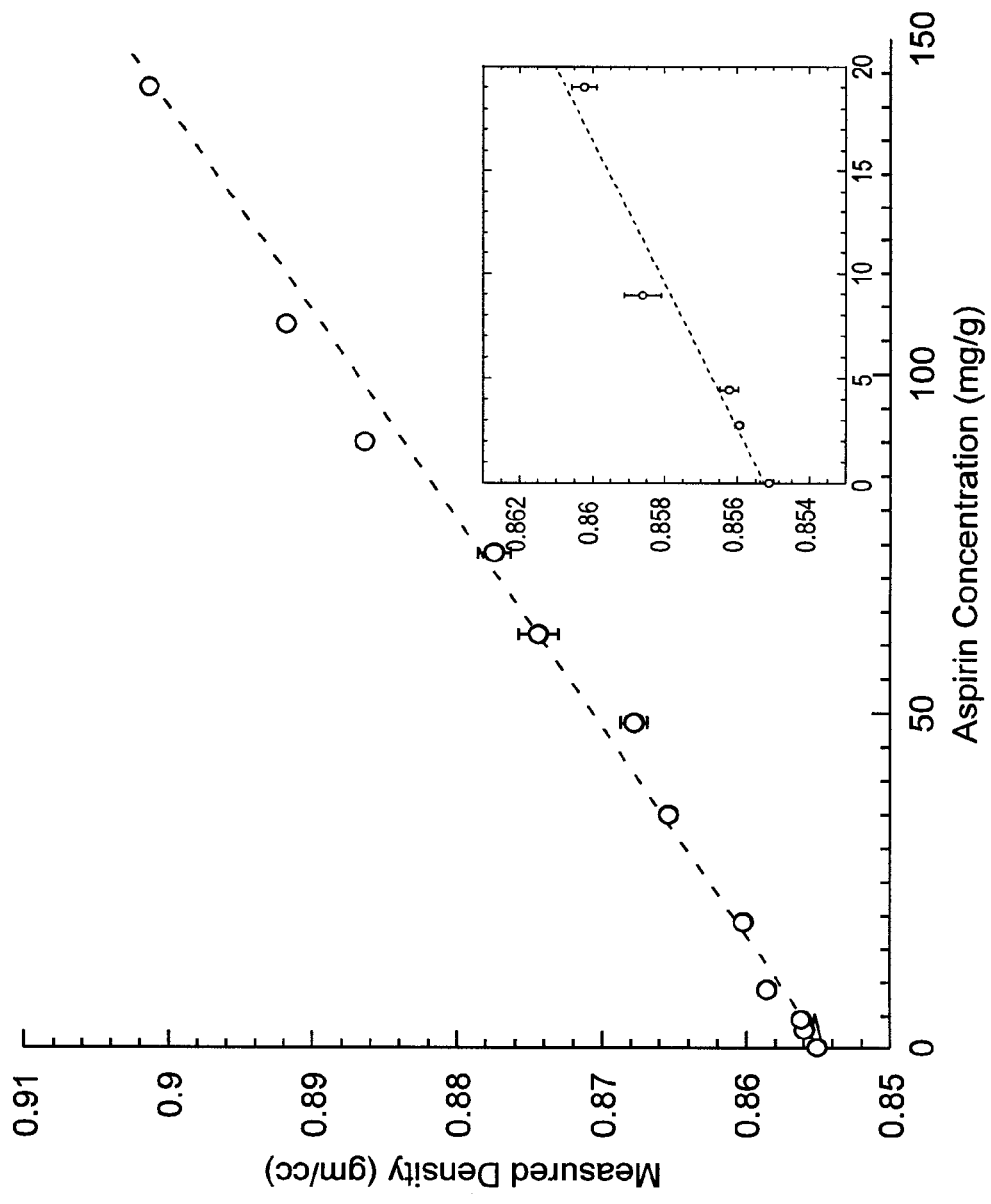
FIG. 11 is a plot illustrating the monitoring data for density for an experiment representing a solute concentration operation, as described in Example 4. The data at low solute concentrations are also shown, on a larger scale, in the insert plot of FIG. 11.

The monitored density data are shown in FIG. 11. These data show readily-detectable differences in density over a broad concentration range of solute. The data at low solute concentrations is also shown, on a larger scale, in the insert plot of FIG. 11. As such, this data demonstrates that the mechanical resonator sensors can be suitably used in the methods and systems of the invention as applied toward solute concentration operations.

Example 5

α-Phellandrene (34.1 g) was added to maleic anhydride (24.5 g) in a 250 ml multi-neck round bottom flask fitted with a reflux condenser. Ether (130 ml) was added to the flask and the resultant mixture was stirred with a magnetic stir bar. A tuning fork resonator was placed into the liquid medium through a rubber septum in a ground glass joint of the flask. Using a heating mantle and a temperature controller the mixture was then heated with stirring to 35° C. and reaction allowed to proceed for at least 3 hours, during which the response of the tuning fork was measured using an acquisition time of 30 seconds. A Diels-Alder adduct was formed which did not precipitate during the course of the reaction:

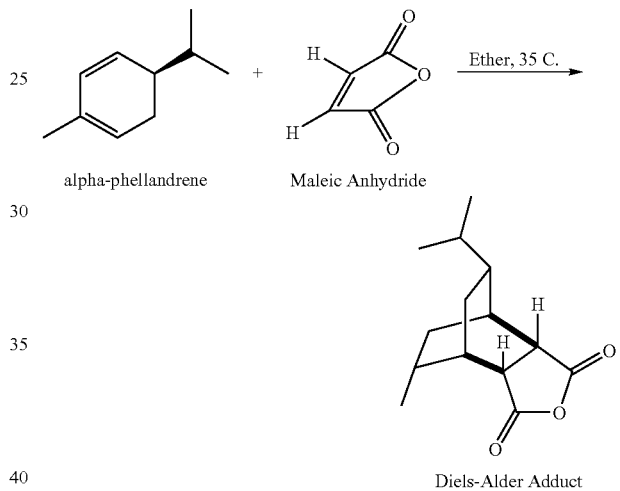

alpha-phellandrene    Maleic Anhydride

Diels-Alder Adduct

Figure 13:
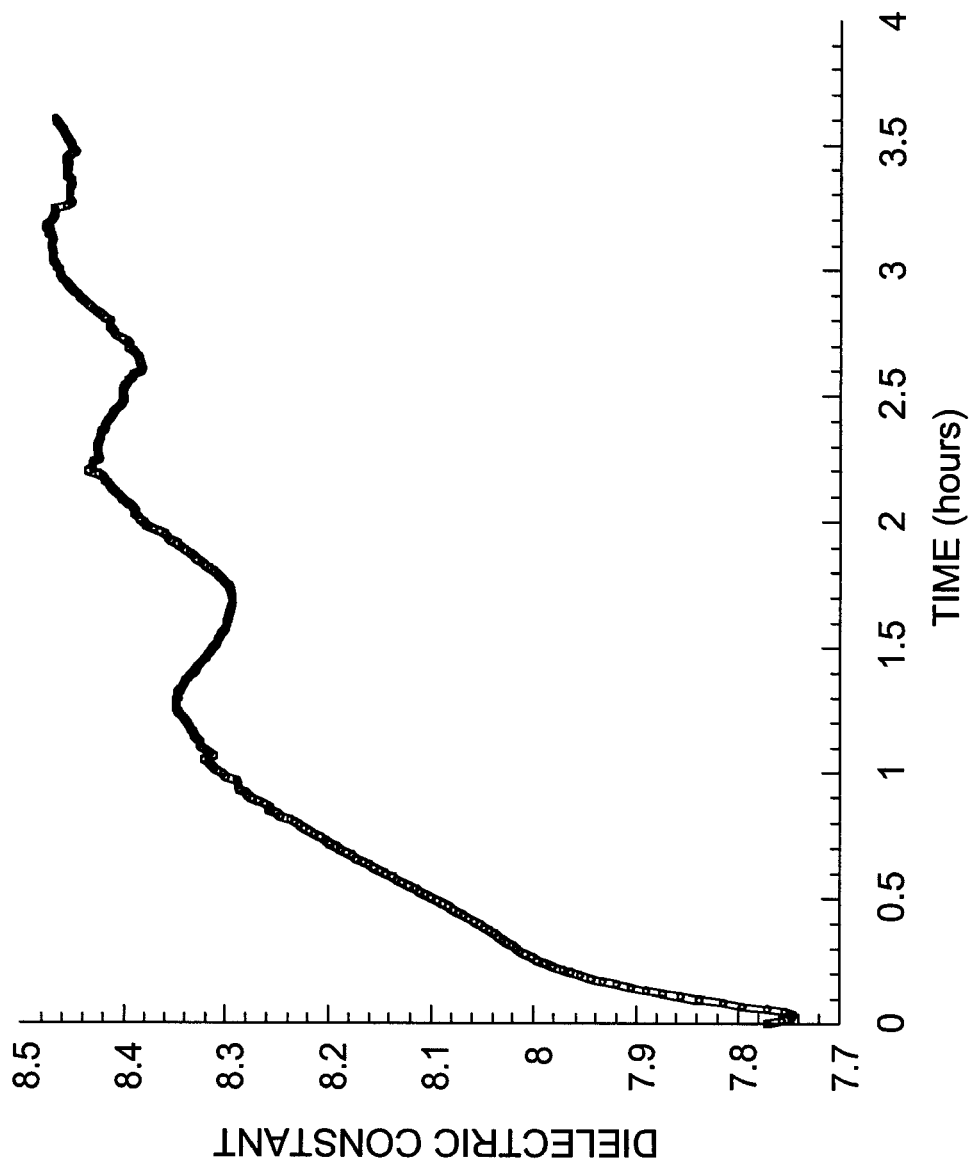
FIG. 13 is a plot illustrating the dielectric constant response (raw data) of a tuning fork resonator vs. time during fast reaction of α-phellandrene with maleic anhydride in an ether reaction medium as described in Example 5.
Figure 14:
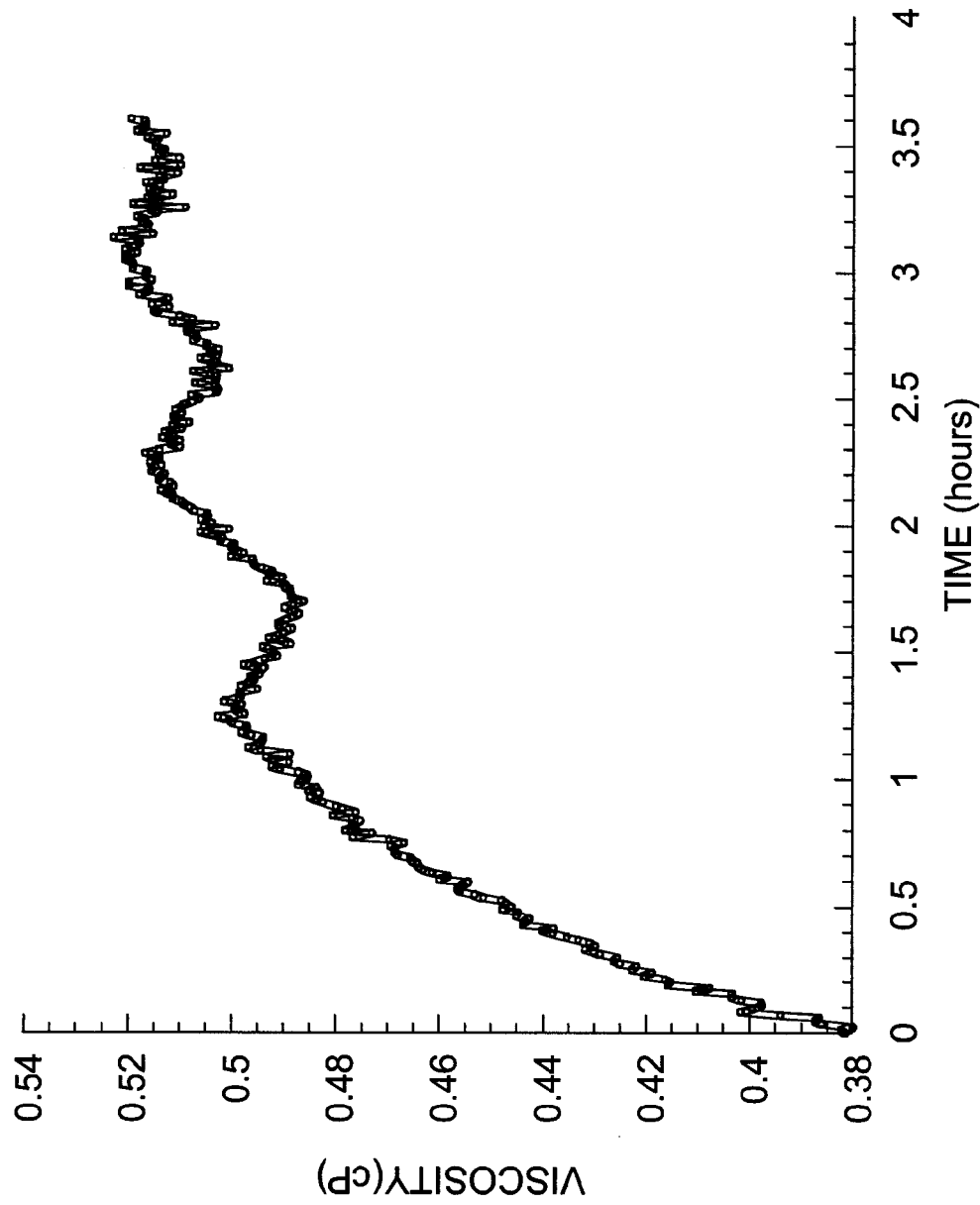
FIG. 14 is a plot illustrating the viscosity response (raw data) of a tuning fork resonator vs. time during the reaction of Example 5.
Figure 15:
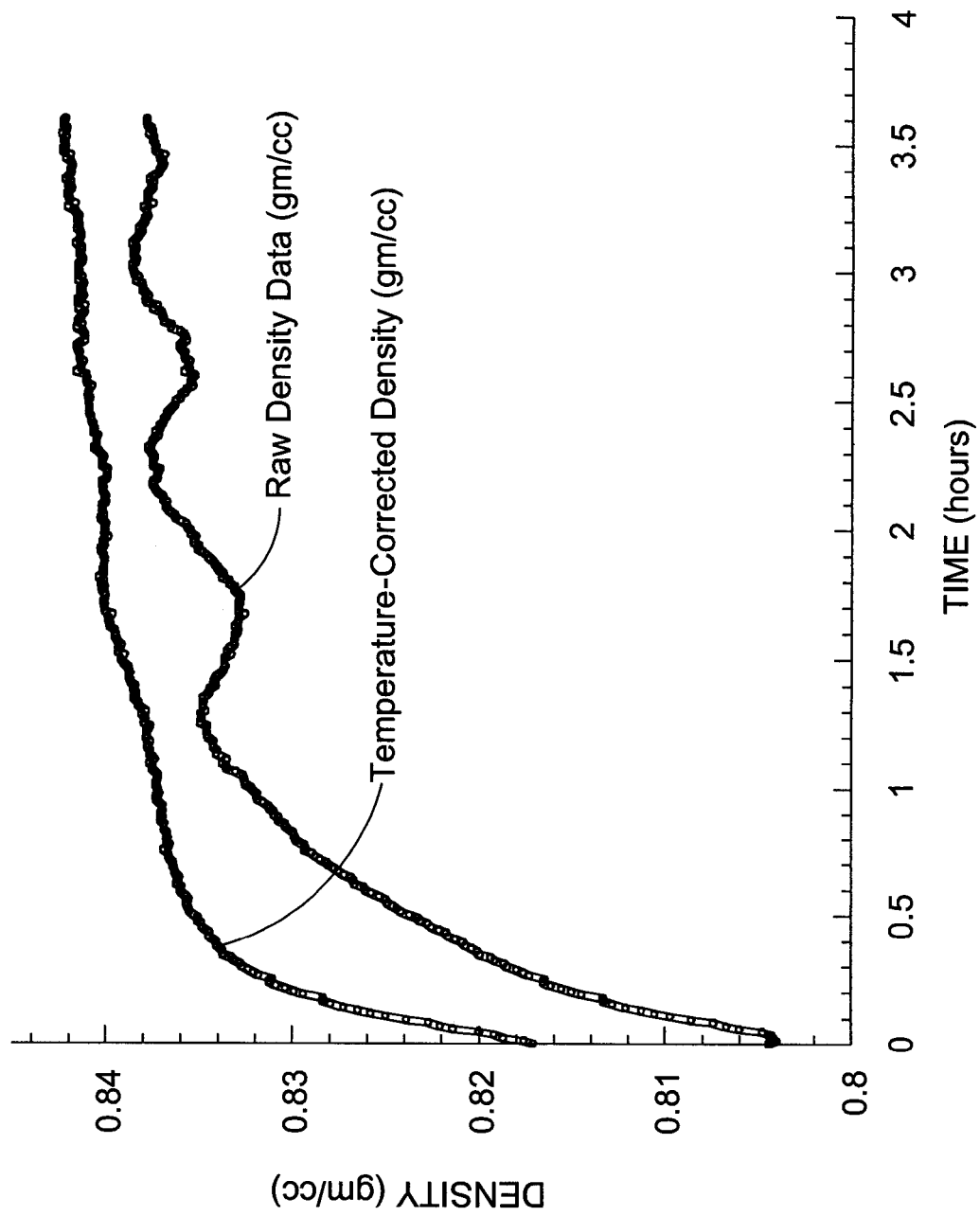
FIG. 15 is a plot illustrating the density response of a tuning fork resonator vs. time during the reaction of Example 5, including plots of both raw data and temperature corrected values.

Set forth in FIGS. 13 to 15, respectively, are the dielectric response, viscosity response and density response of the resonator as a function of time during the reaction. Temperature control during the reaction was relatively uneven (±5° C.), and this may be seen to have created fluctuations in the responses. The upper curve of FIG. 15 reflects an adjustment of the raw data by a temperature correction factor based on the temperature dependence of the density of the ether reaction medium. Similar correction could be applied to the raw data of FIGS. 13 and 14 for dielectric constant and viscosity, if reaction medium dependence on temperature for these properties was previously determined.

Example 6

Maleic anhydride and 1,4-dioxane were introduced into a round bottom flask that was sealed with a septum but vented via a needle which pierced the septum. Furan was added to the maleic anhydride solution with continuous stirring. Initial concentrations of maleic anhydride and furan are set forth for "Experiment 1" in Table 2. After approximately 5 hours, a Diels-Alder adduct product precipitated from the liquid reaction medium.

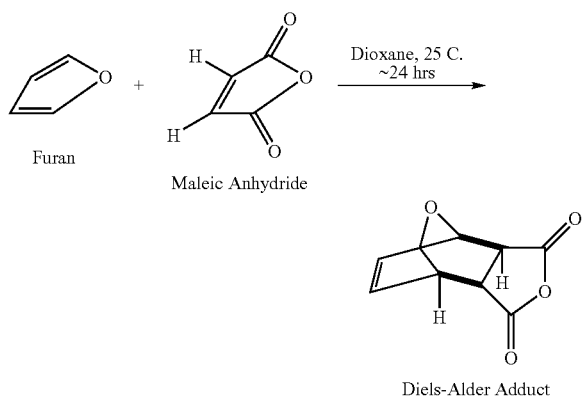

Figure 19:
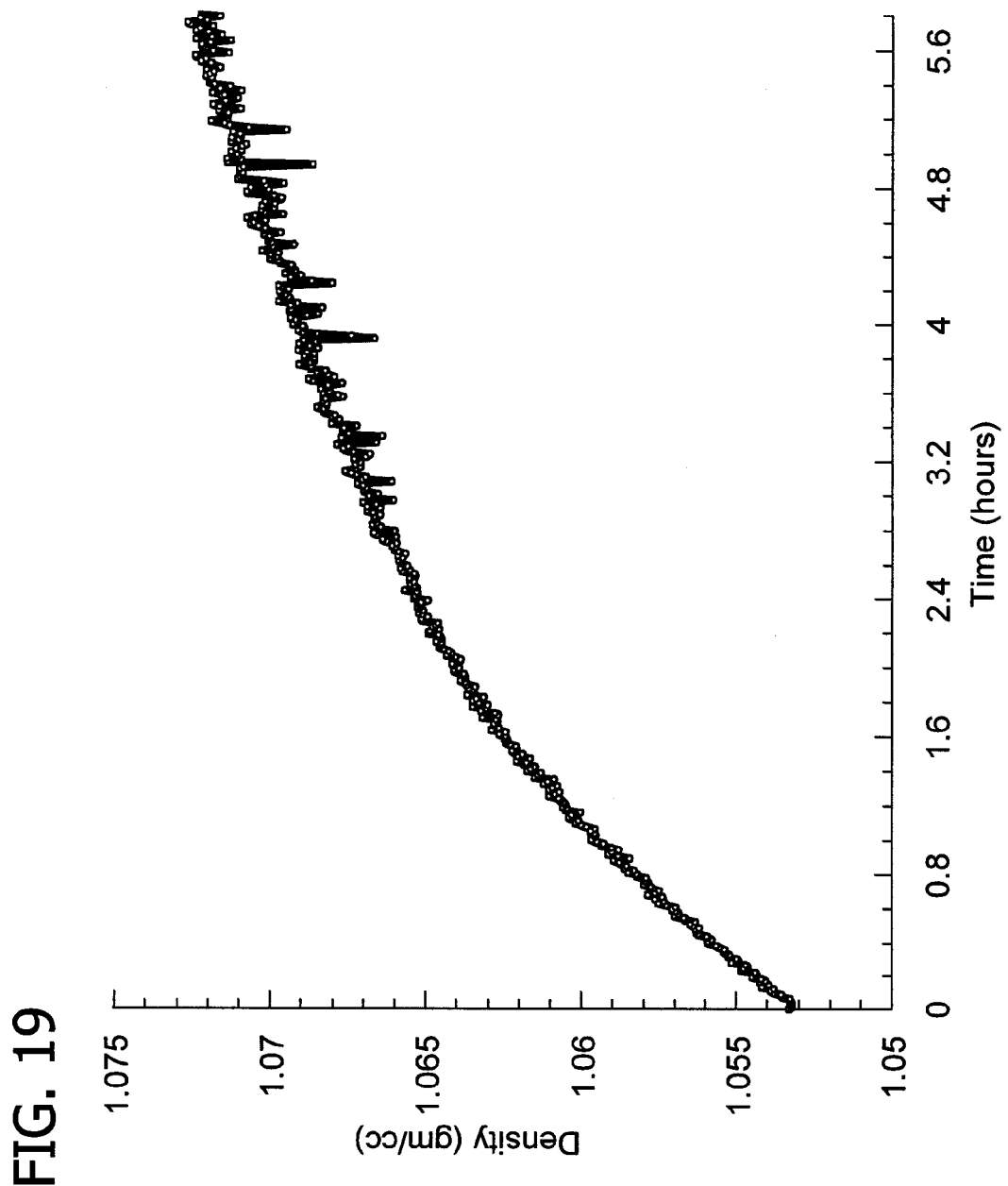
FIGS. 19, 20 and 21 present the density, viscosity and dielectric constant responses of FIGS. 17, 16 and 18, respectively, on an enlarged unit time scale during the period prior to precipitation.
Figure 20:
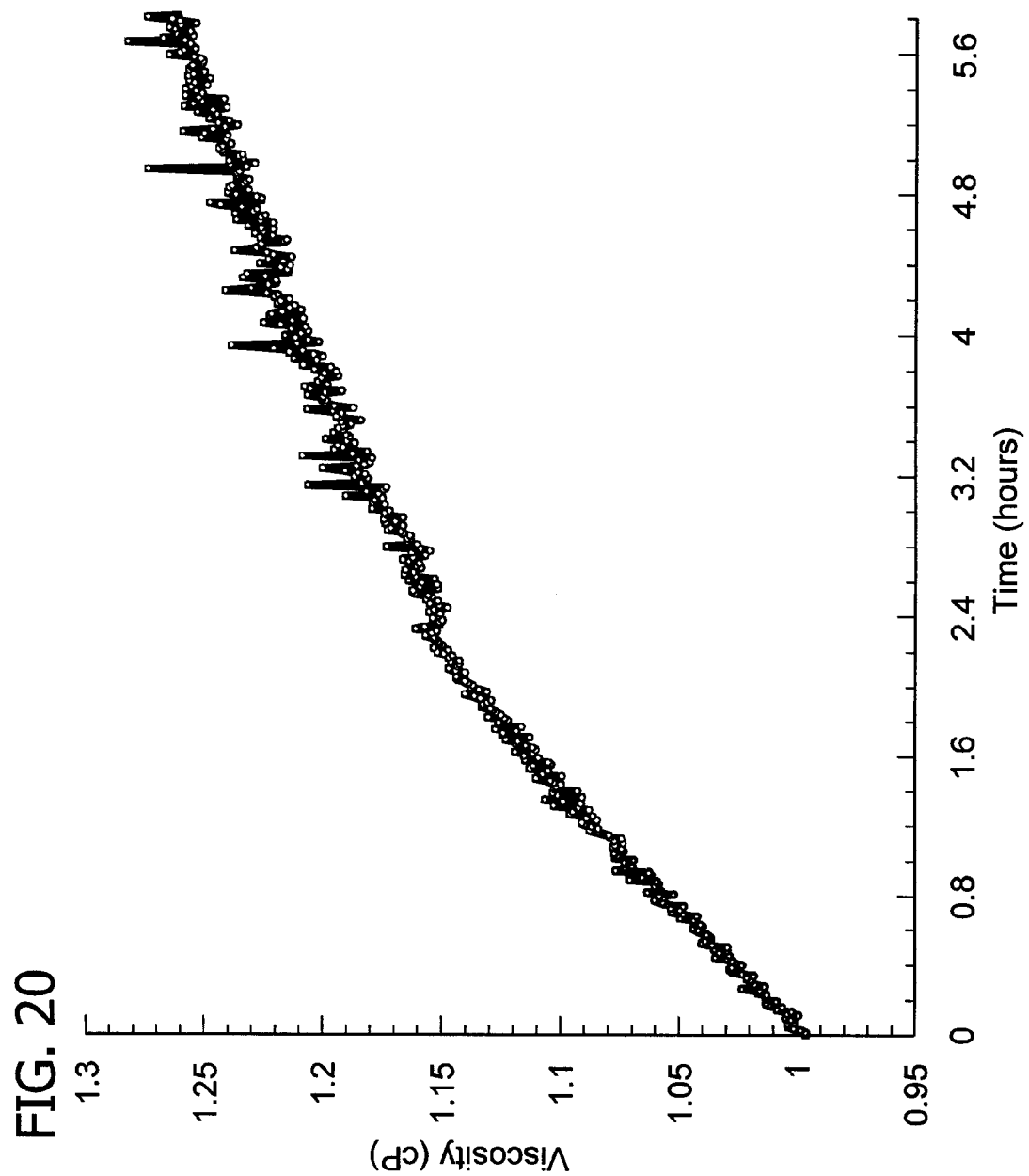
Figure 21:
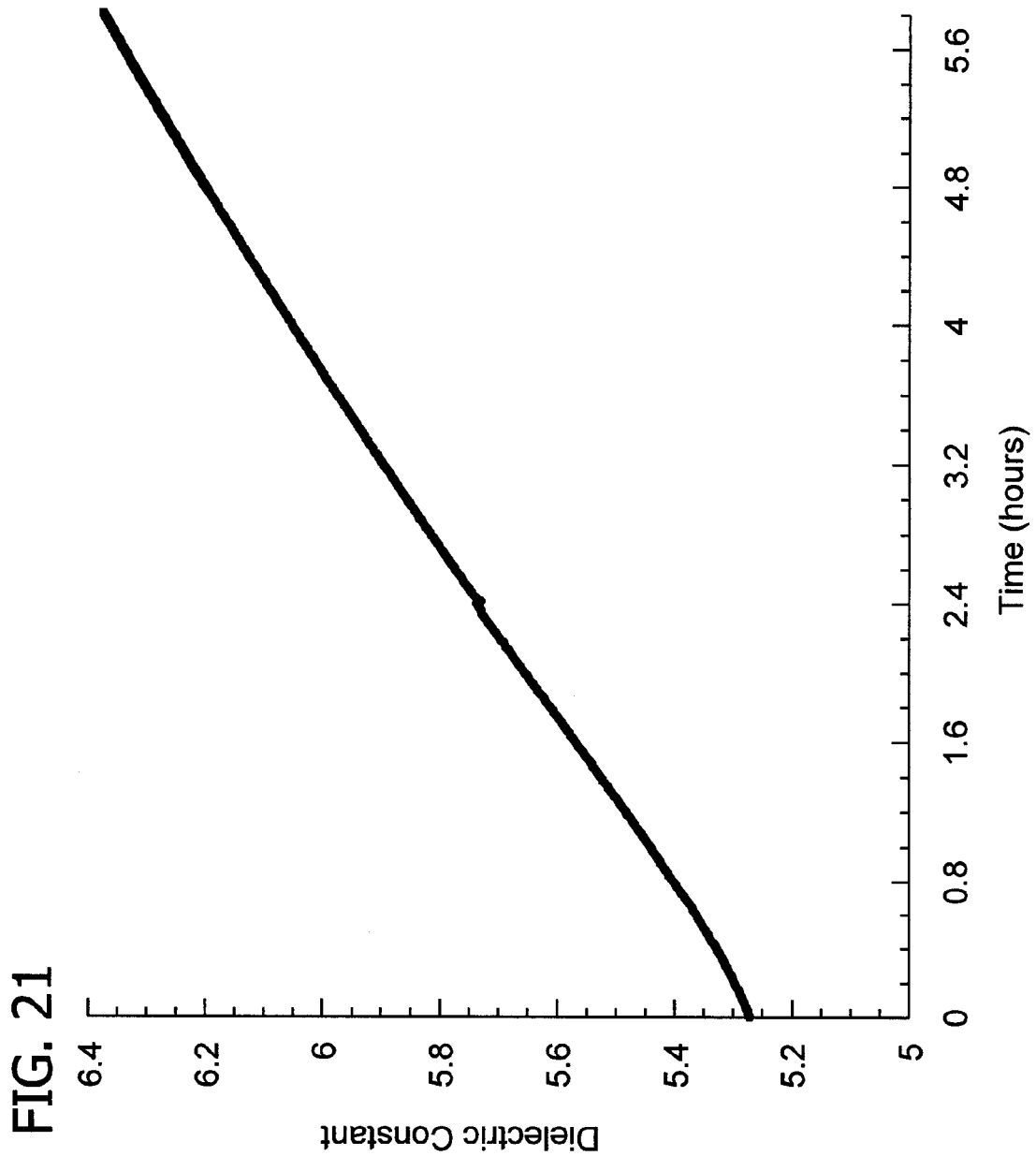

The response of a tuning fork in contact with the reaction medium was measured over a period of 24 hours using an acquisition time of 30 seconds. Set forth in FIGS. 16-18, respectively, are the viscosity response, density response, and dielectric constant response as measured using the tuning fork during the course of the reaction. Deposition of adduct on the tuning fork likely changed calibration parameters significantly. However, reasonable values for the dielectric response continued to be measured even after the step change that resulted from precipitation. Set forth in FIGS. 19-21 are data plots showing the density, viscosity and dielectric responses, respectively, for the period prior to precipitation.

Assuming that the rate of formation of adduct and the rates of consumption of maleic anhydride and furan are the same, and additivity of volume, the rate of reaction may be expressed per equation (1) of FIG. 22, and the rate of density change may be related to the rate of reaction as shown in equations (2) and (3) of FIG. 22, where:

$\rho$=the density of the reaction mass at time t
$\rho_0$=the initial density of the reaction mass
$\rho_{MA}$=the density of maleic anhydride at the reaction temperature
$\rho_{FUR}$=the density of furan at the reaction temperature
V=the Volume of the condensed phase reaction mixture at time t Several additional reactions of maleic anhydride and furan were conducted under the conditions generally described above, except that the initial concentrations of maleic anhydride and furan were varied. Each reaction was monitored with the tuning fork in the manner described above. Set forth in Table 2 are the initial conditions for each run; and set forth in Table 3 are the initial density readings for each run, the initial rate of change of the density with time for each run, and the initial rate of reaction as calculated using equations (1) to (3) above.

TABLE 2

| Experiment Number | Initial Maleic Anhydride Concentration (mg/g) | Initial Furan Concentration (mg/g) |
|---|---|---|
| 1 | 220 | 153 |
| 2 | 123 | 171 |
| 3 | 238 | 83 |
| 4 | 135 | 94 |

TABLE 3

| Experiment Number | Initial Density Reading | Initial Rate of Change of Density (gm/cc/hr) | Calculated Initial Rate of Reaction (l/hr) |
|---|---|---|---|
| 1 | 1.0800 | 0.0145 | 0.01023 |
| 2 | 1.0531 | 0.0067 | 0.00497 |
| 3 | 1.0962 | 0.0052 | 0.00356 |
| 4 | 1.0619 | 0.0019 | 0.00139 |

Figure 23:
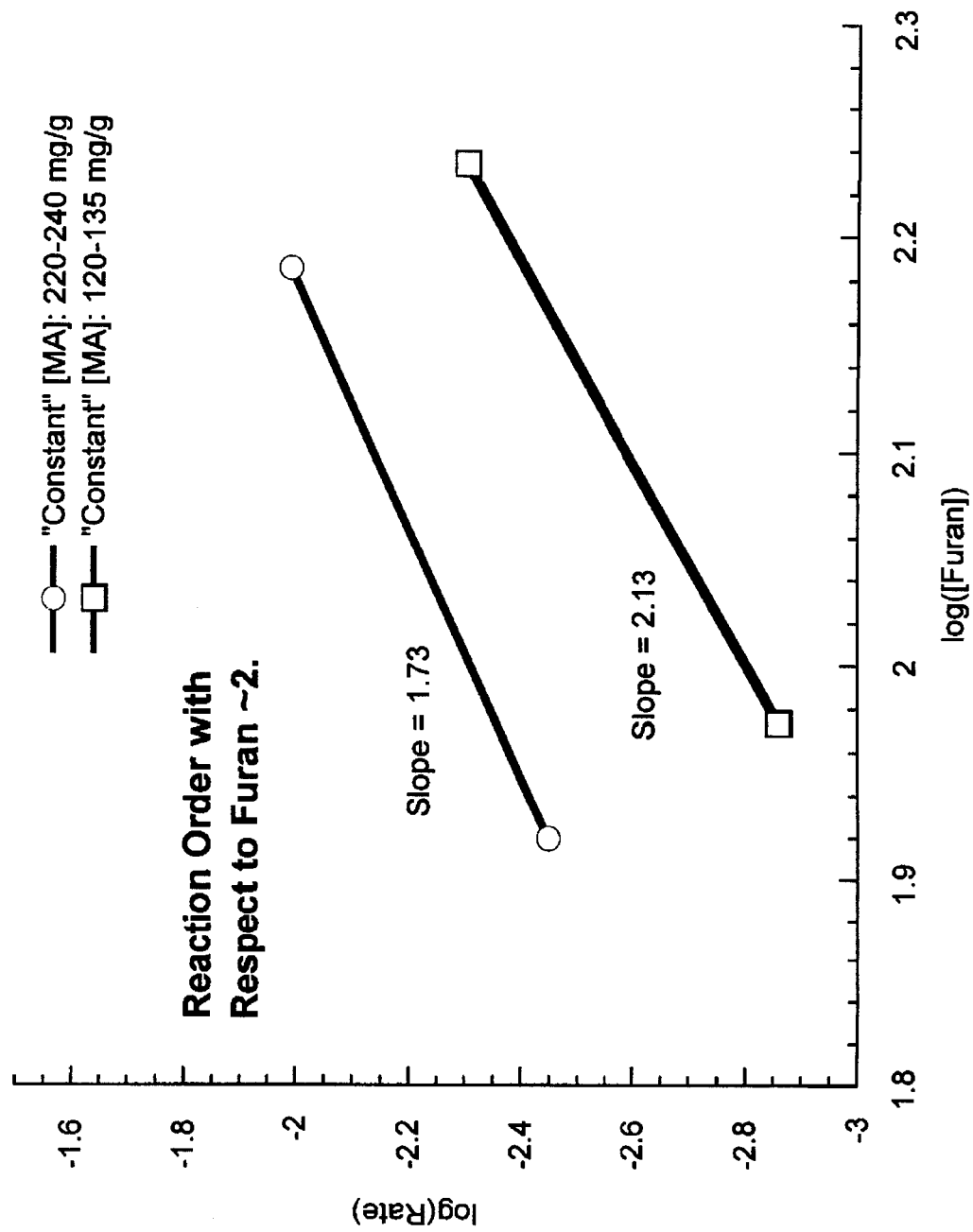
FIG. 23 sets forth plots of the logarithm of the instantaneous reaction rate vs. the logarithm of the furan concentration for various combinations of initial furan concentration and initial maleic anhydride concentration as described in Example 6, depicting slopes at substantially constant maleic anhydride concentration which are indicative of the order of the reaction with respect to furan.

It may be seen that reactions were run within two separate relatively narrow ranges of initial maleic anhydride concentration, i.e., Experiments 1 and 3 were run in a "constant" initial range of approximately 220-240 mg/g while Experiments 2 and 4 were run in a "constant" initial range of approximately 120-135 mg/g. By varying the initial furan content relatively widely within each narrow range of initial maleic anhydride concentration, the varying initial reaction rates may be determined at each maleic concentration level. Thus, by plotting the log of the initial reaction rate against the log of the initial furan content, a relationship may be derived, the slope of which reflects the approximate order of the reaction with respect to furan. Such plots, as illustrated in FIG. 23, indicate that the reaction is essentially second order with respect to furan.

Figure 24:
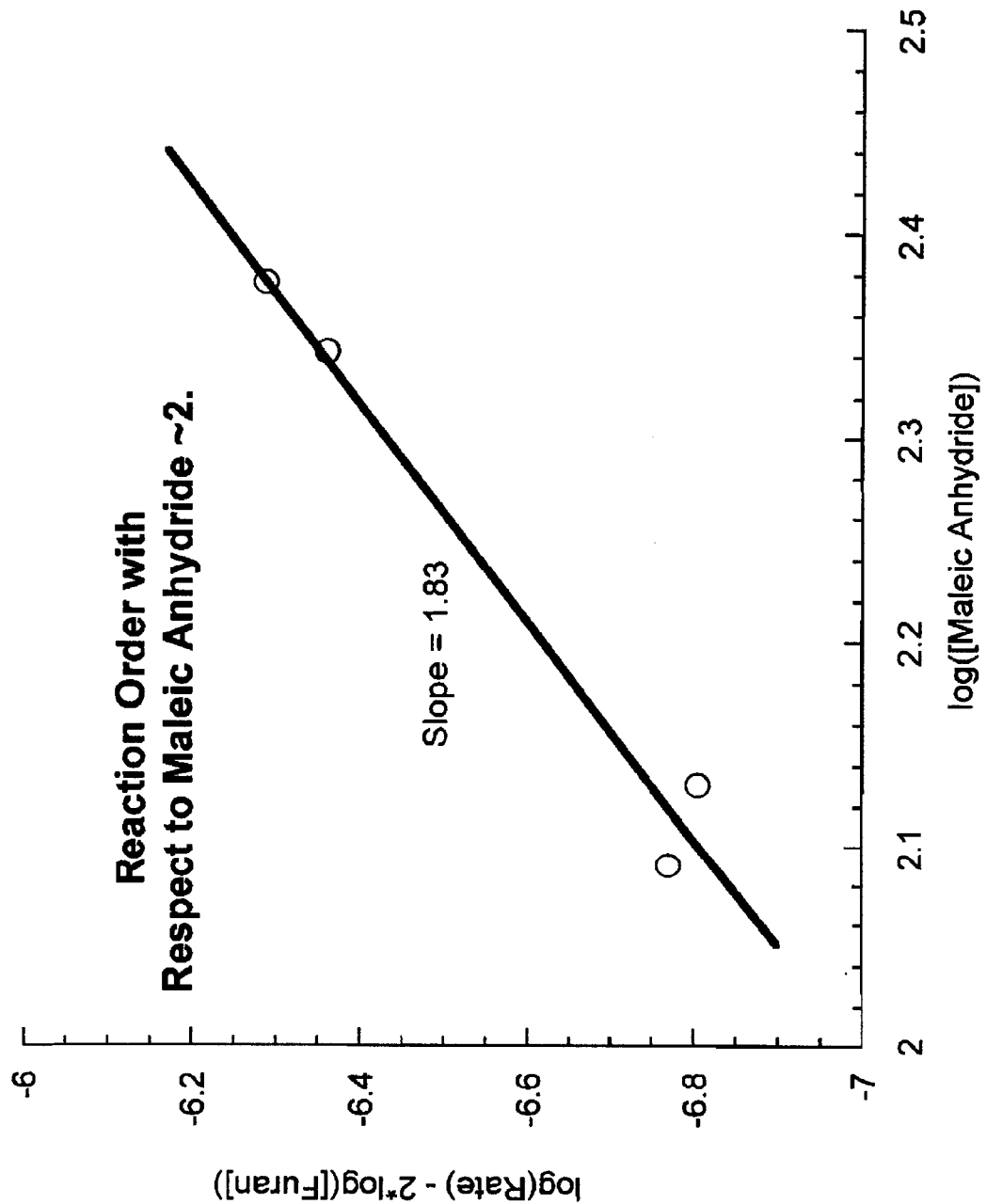
FIG. 24 is a plot of the logarithm of instantaneous reaction rate vs. the logarithm of instantaneous maleic anhydride concentration in the reactions of Example 6, and includes a plot depicting a slope indicative of the order of the reaction with respect to maleic anhydride.

As shown in FIG. 24, a similar relationship can be plotted for the log of the reaction rate vs. the log of the initial maleic anhydride concentration. In this case, since the order of the reaction with respect to furan has been determined, a single curve can be plotted by taking the contribution of the furan concentration to the reaction rate into account. Based on the reaction rate equations set forth above, where b=2:

$-dc/dt = kc_A{}^a c_B{}^b$ where:

$c_A$=the instantaneous concentration of maleic anhydride
$c_B$=the instantaneous concentration of furan
a=the order of the reaction re maleic anhydride
b=order of reaction re furan=2
$-dc/dt$ =the rate of the reaction=$-dc_{A/dt}=-dc_B/dt$ and thus:

$\log[-dc/dt] = a[\log(c_A)] + 2[\log(c_B)]$
$a[\log(c_A)] = \log[-dc/dt] - 2[\log(c_B)]$ This relationship is plotted in FIG. 24, with the slope "a" reflecting the order of reaction with respect to maleic anhydride, which may be seen to be roughly second order as well.

Figure 18:
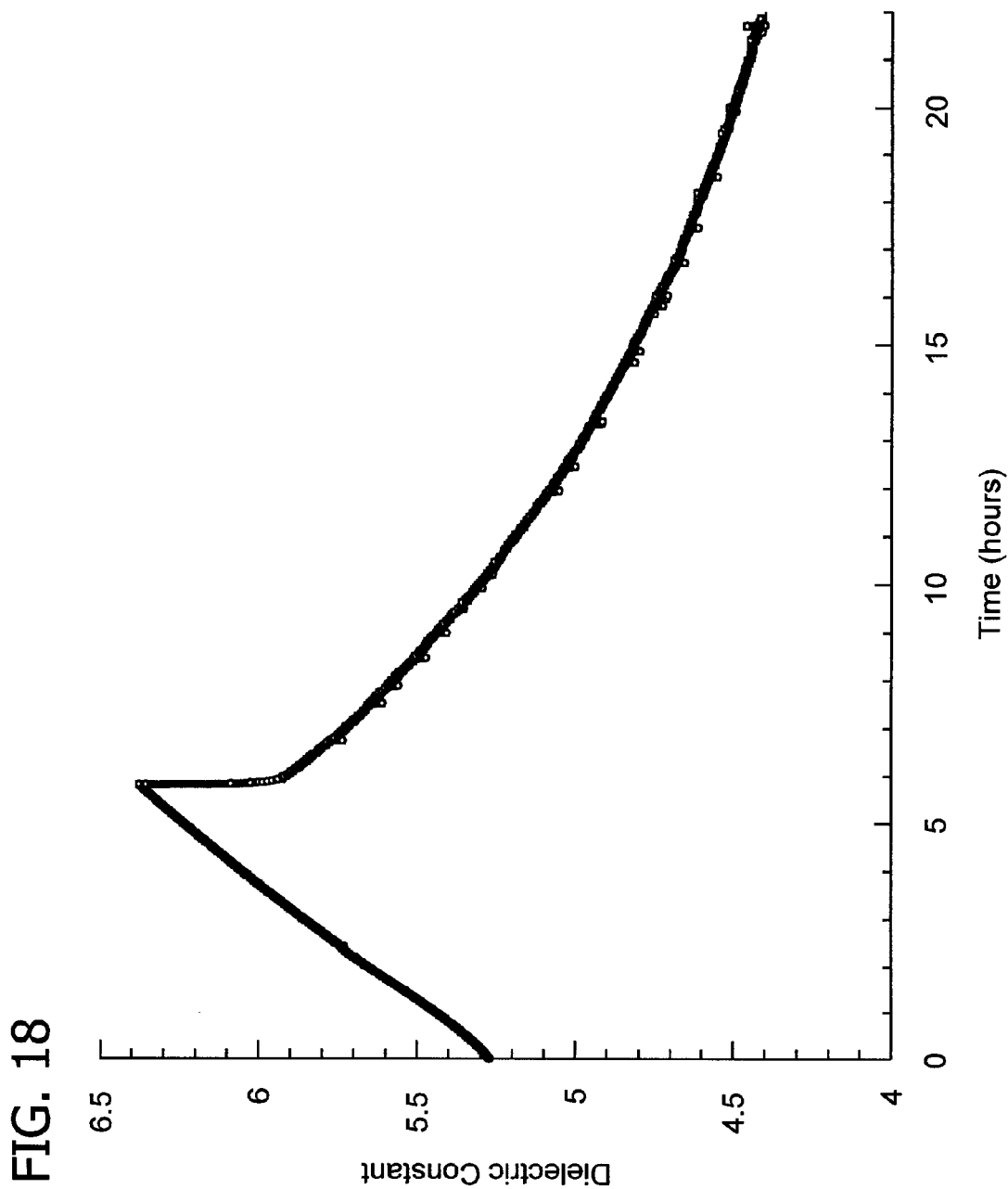
FIG. 18 is a plot illustrating the dielectric constant response of a tuning fork resonator vs. time during the reaction of Example 6.
Figure 25:
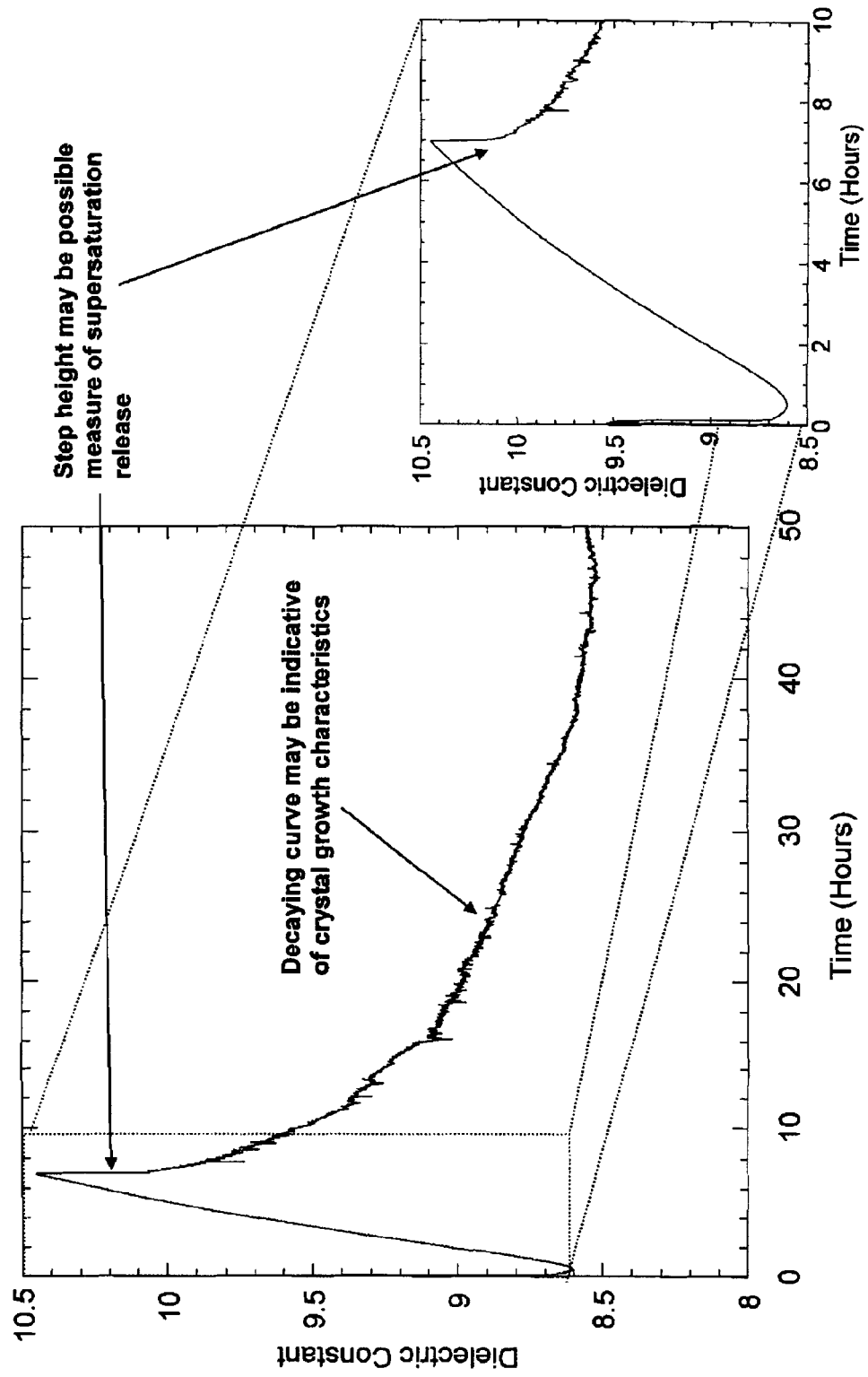
FIG. 25 is a plot of dielectric constant vs. time during the slow reaction of furan with maleic anhydride in a dioxane medium as described in Example 6, and includes an excerpt on an enlarged unit scale of dielectric constant vs. time for the reaction mixture through the early stages of precipitation.

FIGS. 18 and 25 reflect a discontinuity (step change) in the dielectric response at the point at which precipitation commences, possibly reflecting relatively massive nucleation from the dioxane medium which had become supersaturated with the adduct reaction product. The decay curve generated after the discontinuity is believed to reflect crystal growth after the initial precipitation.

Figure 16:
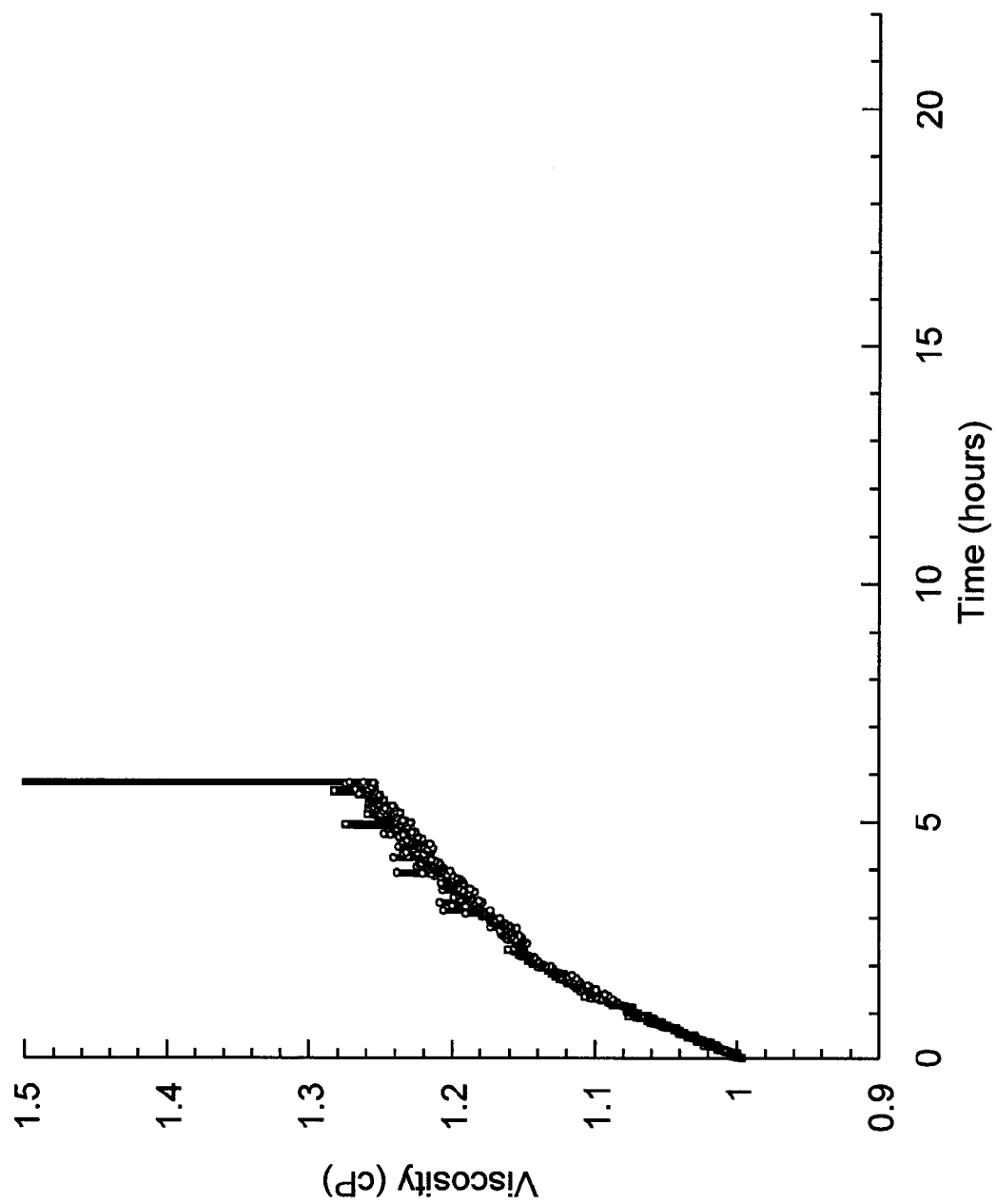
FIG. 16 is a plot illustrating the viscosity response of a tuning fork resonator vs. time during slow reaction of furan and maleic anhydride in a dioxane medium with precipitation of the Diels-Alder adduct, as described in Example 6.
Figure 17:
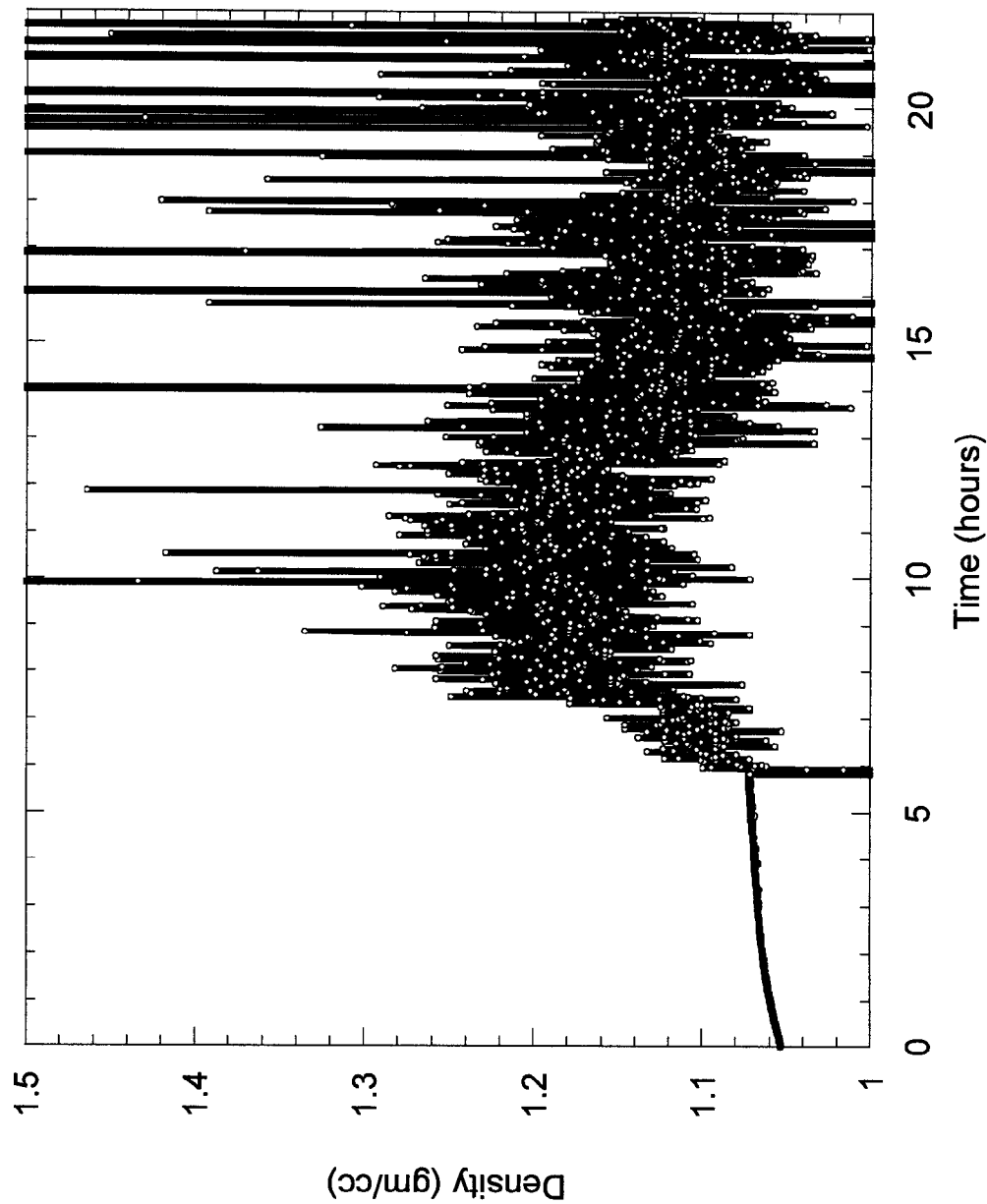
FIG. 17 is a plot illustrating the density response of a tuning fork resonator vs. time during the reaction of Example 6.

Comparing FIGS. 13 to 15 vs. FIGS. 16 to 18 (and 25), the relatively smooth curves for all three parameters, i.e., density, viscosity and dielectric constant, in Example 5 appear to be consistent with the absence of precipitation, which was, in fact, not observed in the reaction of α-phellandrene with maleic anhydride at the stated concentrations in the ether medium. By comparison, the profiles of FIGS. 16-18 are qualitatively similar to those of FIGS. 13-15 for the Example 6 reaction period prior to precipitation, while the dielectric constant step change may be a measure of supersaturation release, and the dielectric constant profile after precipitation may be indicative of crystal growth and useful in monitoring the progress of crystallization.

Thus the tuning fork sensor's ability to simultaneously monitor density, dielectric constant and viscosity provides multiparametric data from the reactions that indicates its value in monitoring and characterizing reactions.

Example 7

In accordance with the experimental procedure for this example, sodium bicarbonate is shaken with a desired test solvent to form a slurry in a Wheaton bottle. The solids are separated by vacuum filtration of the slurry through a medium-porosity glass frit. The wet solids (~150 g) are charged to a 250 ml single-neck round bottom flask. The flask is then fitted to a modified "Rotovap" setup as reflected schematically in FIG. 26 but further comprising a condenser (not shown) for solvent vapor removed from the wet solids. A quartz tuning fork is placed in the glassware conduit upstream of the condenser via a vacuum feed-through. The flask is then rotated at 30 rpm in a temperature controlled water bath while a vacuum controller maintains the pressure within the flask within ±1% of the set point. The tuning fork response is transmitted to a network analyzer.

Figure 27:
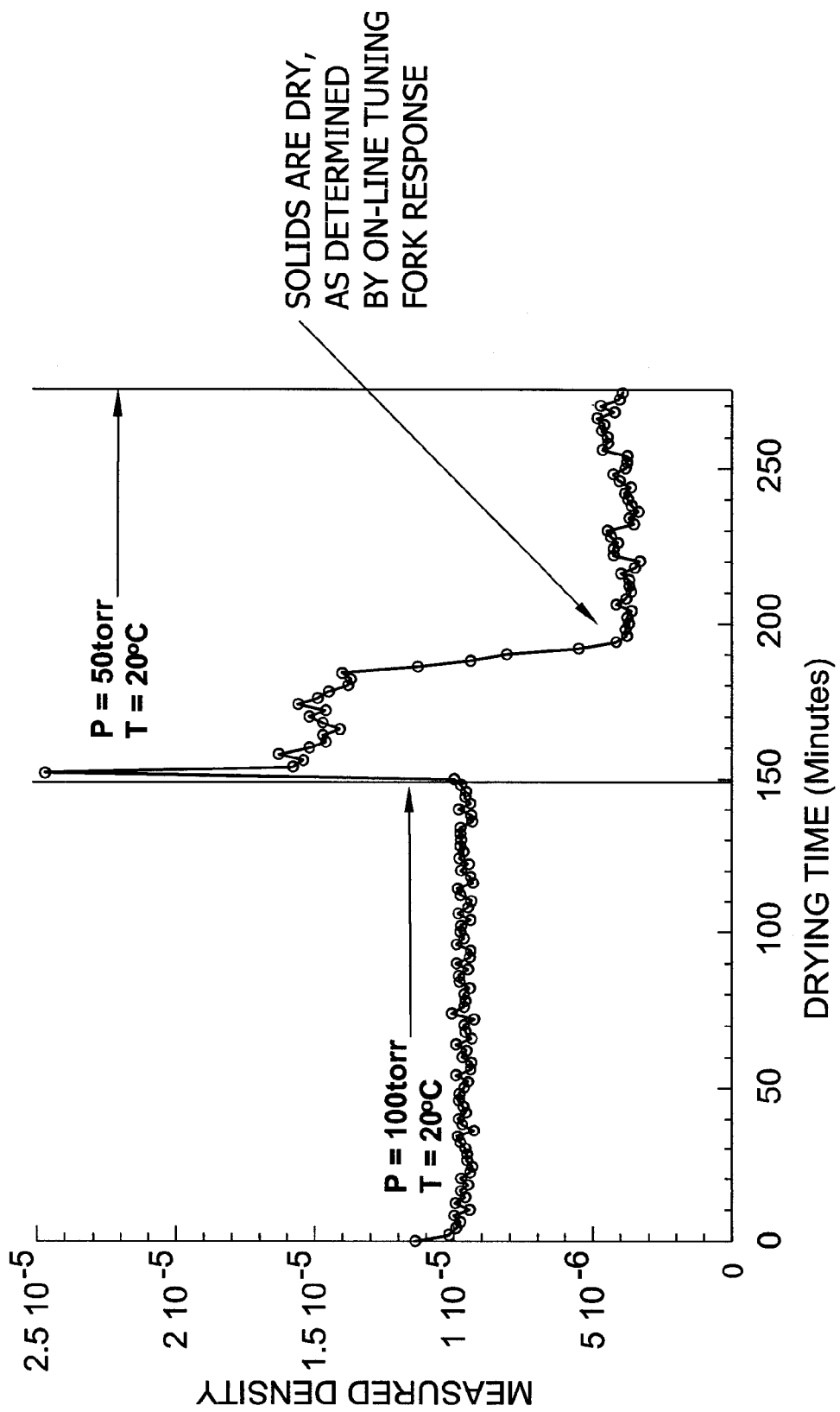
FIG. 27 is a plot of the density response of a tuning fork resonator in the vapor line from the dryer as a function of time during the removal of isopropyl acetate from a wetcake consisting of particulate sodium bicarbonate wetted with isopropyl acetate as described in Example 7.

FIG. 27 illustrates the density response during a vacuum drying cycle for sodium carbonate solids wetted with isopropyl acetate, in which the temperature of the wet solids was maintained at about 20° C. and the dryer was evacuated to an absolute pressure of 100 torr for the first 150 minutes, then reduced to 50 torr for approximately another 125 minutes. As expected, the density response varied with the absolute pressure. A decent signal to noise ratio was observed, even at the lower pressure of 50 torr. After a spike in density immediately upon reduction of the absolute pressure from 100 torr to 50 torr, the density substantially stabilized at a level somewhat higher than the steady state density at 100 torr. After about 180 minutes, the solvent was substantially exhausted and a significant drop in density was observed reflecting an increase in the fraction of the relatively low density non-condensables flowing past the tuning fork after substantial exhaustion of the relatively high density isopropyl acetate.

In this example, identification of the end point is quite definitive.

Example 8

Figure 28:
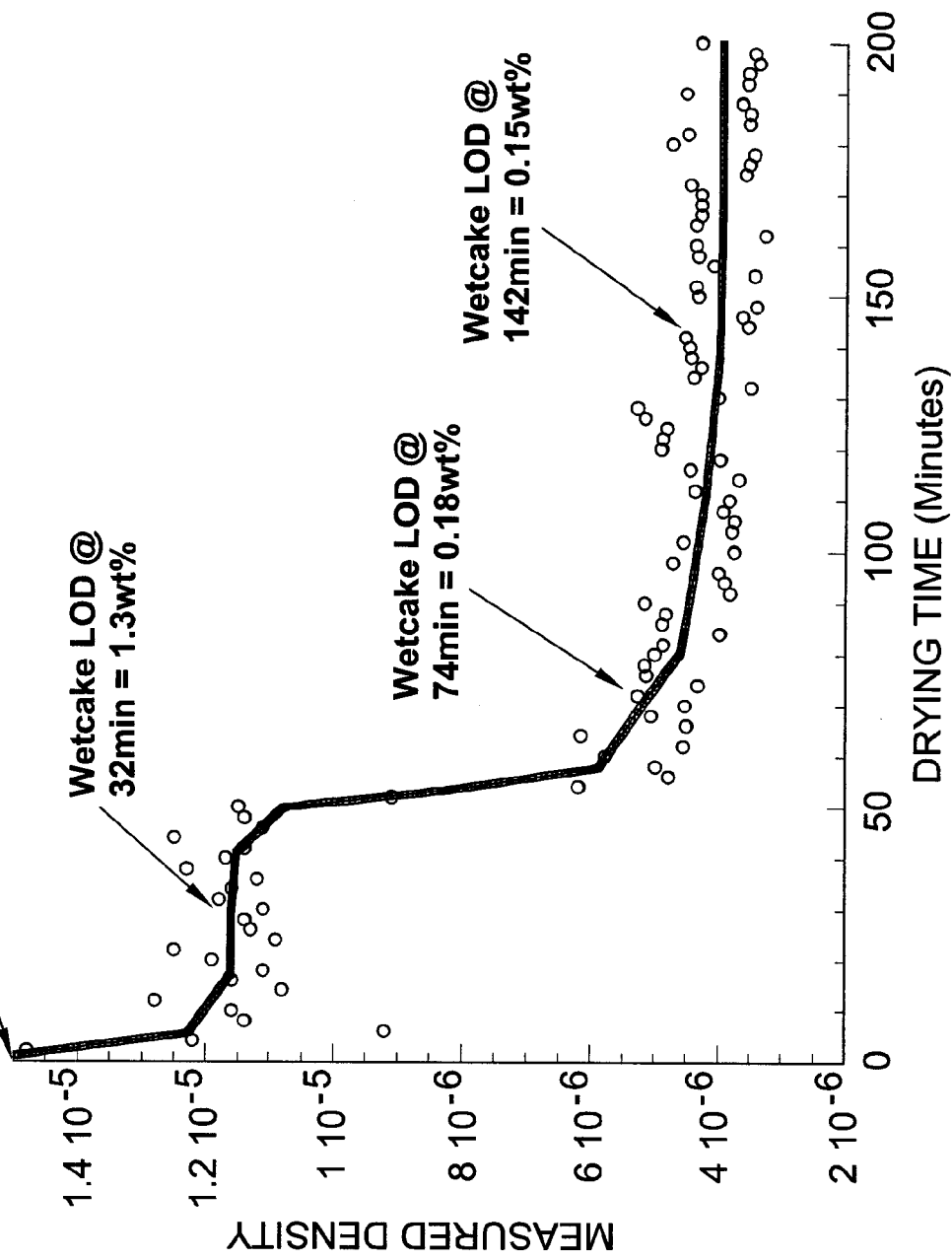
FIG. 28 is plot of the density response of a tuning fork resonator in the vapor line from the dryer as a function of time during the removal of isopropyl acetate from a wetcake consisting of particulate sodium bicarbonate wetted with isopropyl acetate as described in Example 8 superimposed upon which are determinations of wet cake loss-on-drying ("LOD").

Sodium bicarbonate wetted with isopropyl acetate was prepared and dried, and the density of the vapor stream exiting the drying chamber was monitored, in a manner substantially as described in Example 7, except that the pressure was maintained at about 50 torr substantially throughout the drying cycle. As illustrated in FIG. 28, samples of the wetcake were taken at three times during the drying, once after about 32 minutes drying time during the period in which the measured density plateaued at a value on the order of about $1.2 \times 10^{-5}$ g/cc, once after about 74 minutes of drying time which was several minutes after a sharp drop in density to about $5 \times 10^{-6}$ g/cc, and finally after about 142 minutes during a terminal period in which the density had plateaued at approximately $4 \times 10^{-6}$ g/cc. As further indicated in FIG. 28, the loss-on-drying ("LOD") of the 32 minute sample was 1.3 wt. %, the LOD of the 74 minute sample was 0.18 wt. %, and the LOD of the 142 minute sample was 0.15 wt. %. Thus, there is a strong correlation between the decline in density of the off vapor stream (and thus the isopropyl acetate content thereof) vs. the LOD of the solid sodium bicarbonate from which the vapor stream has been instantaneously removed. These data further demonstrate that the tuning fork response can be correlated with LOD to a detection level on the order of 0.1 wt. % residual solvent.

Example 9

The solids drying operation of Example 8 was repeated except that signal to noise ratio was increased by increasing the DAQ time from 2 min/sweep to 4 min/sweep. The plot of vapor density vs. time for this operation is shown in FIG. 29.

Examples 8 and 9 demonstrate the utility of a tuning fork resonator for distinguishing between saturated vapor and dry vapor conditions during operation of a drying process for removal of a solvent such as isopropyl acetate from solids such as sodium bicarbonate.

Example 10

Figure 30:
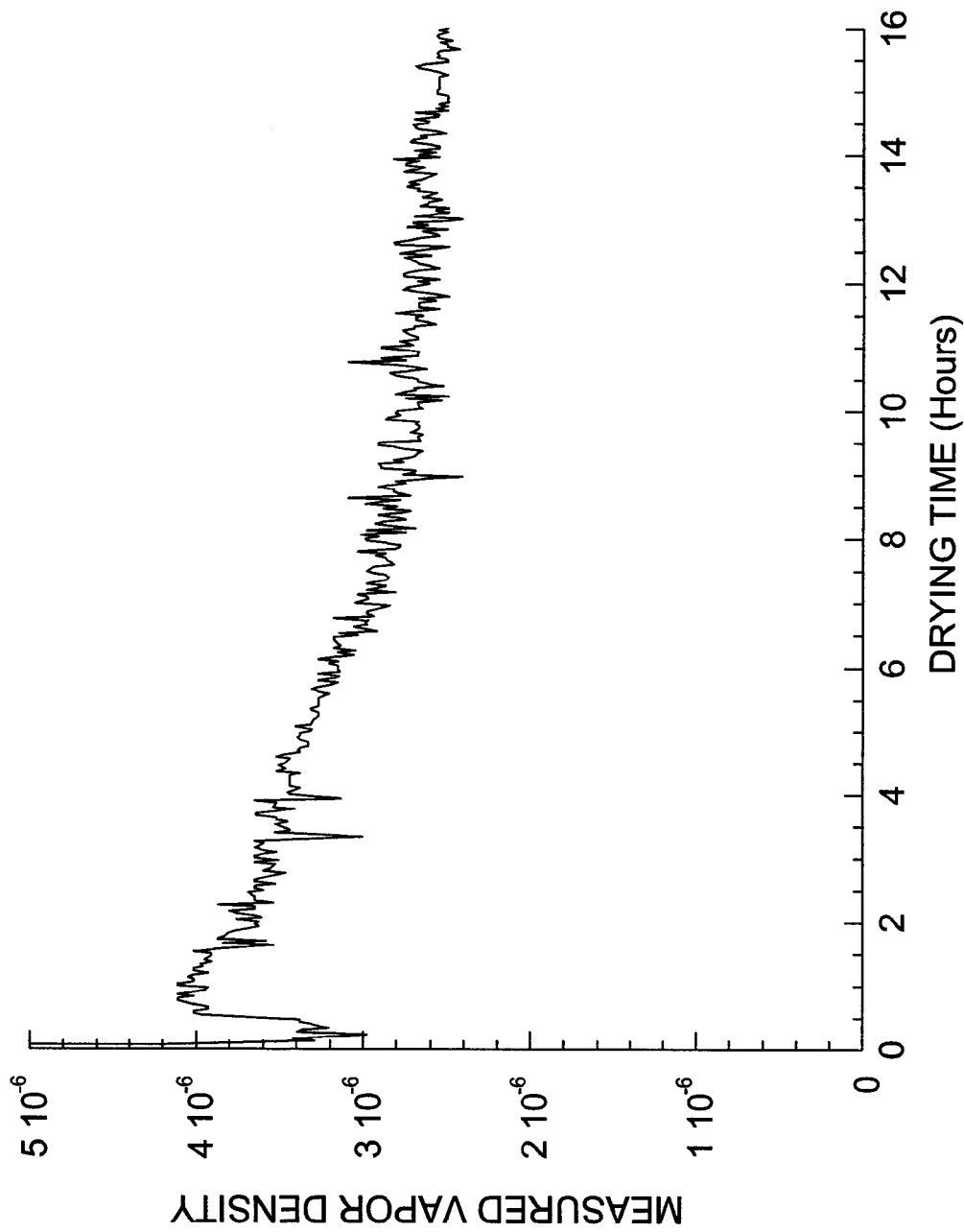
FIG. 30 is a plot of the density response of a tuning fork in the vapor line from the dryer as a function of time during removal of water and isopropyl acetate from a wetcake consisting of sodium bicarbonate wetted with both isopropyl acetate and water, as described in Example 10.

The solids drying operation of Example 8 was repeated except that the sodium bicarbonate was wetted with a bi-component solvent system comprising both isopropyl acetate and water. Results of this operation are illustrated in FIG. 30. It may been seen that the results in this case are significantly noisier than a system in which the solvent is isopropyl acetate alone. The less definitive density response can be attributed to the fact that the molecular weight of isopropyl acetate is 60.1 while the molecular weight of water is 18, thus bracketing the molecular weight of air which is 28.8.

Based on the disclosure herein, those skilled in the art may readily devise data reduction software effective to improve the resolving power of the tuning fork sensing method for solvents similar to air. However, resolution is generally better for relatively heavy solvents, having molecular weights substantially higher than air, than for lighter organic solvents or water. Signal to noise ratio can be enhanced if the background non-condensable gas is selected as having a molecular weight that is as far different from the molecular weight of the solvent as may be practical. For example, He enhances signal to noise where a heavy solvent is involved, while Ar may be preferred for lighter solvents.

Example 11

The applicability of a tuning fork resonator for monitoring a solvent switch operation was demonstrated by preparing specimens of binary and ternary solvent mixtures in relative proportions that would typically prevail in the course of solvent switch, specifically downstream of a condenser in fluid communication with the still pot. Each of three separate systems was exemplified with a series of samples at varying concentrations, i.e.: ethyl acetate/n-heptane (binary system; density range 0.902 to 0.684) reflective of the course of a solvent switch in which ethyl acetate is replaced by n-heptane; tetrahydrofuran(THF)/ethyl acetate (binary system; density range 0.8892 to 0.902) reflecting the course of a solvent switch operation in which THF is replaced by ethyl acetate; and THF/ethyl acetate/n-heptane (ternary system) reflective of the course of a solvent switch operation in which THF and ethyl acetate are replaced by n-heptane. To prepare each of the samples, neat solvents were weighed into scintillation vials to produce the various mixtures of varying concentration, each with 0.1 mg precision.

A tuning fork resonator was immersed in each open scintillation vial without temperature control. Using the tuning fork resonator, four repeat measurements of density were made for each sample mixture (30 second acquisition time for each measurement). The temperature of each sample was also measured. Each density measurement was temperature corrected to a standard 20° C. using the published thermal coefficient of expansion (TCE) of the least volatile solvent at the temperature of measurement.

Figures 31, 32:
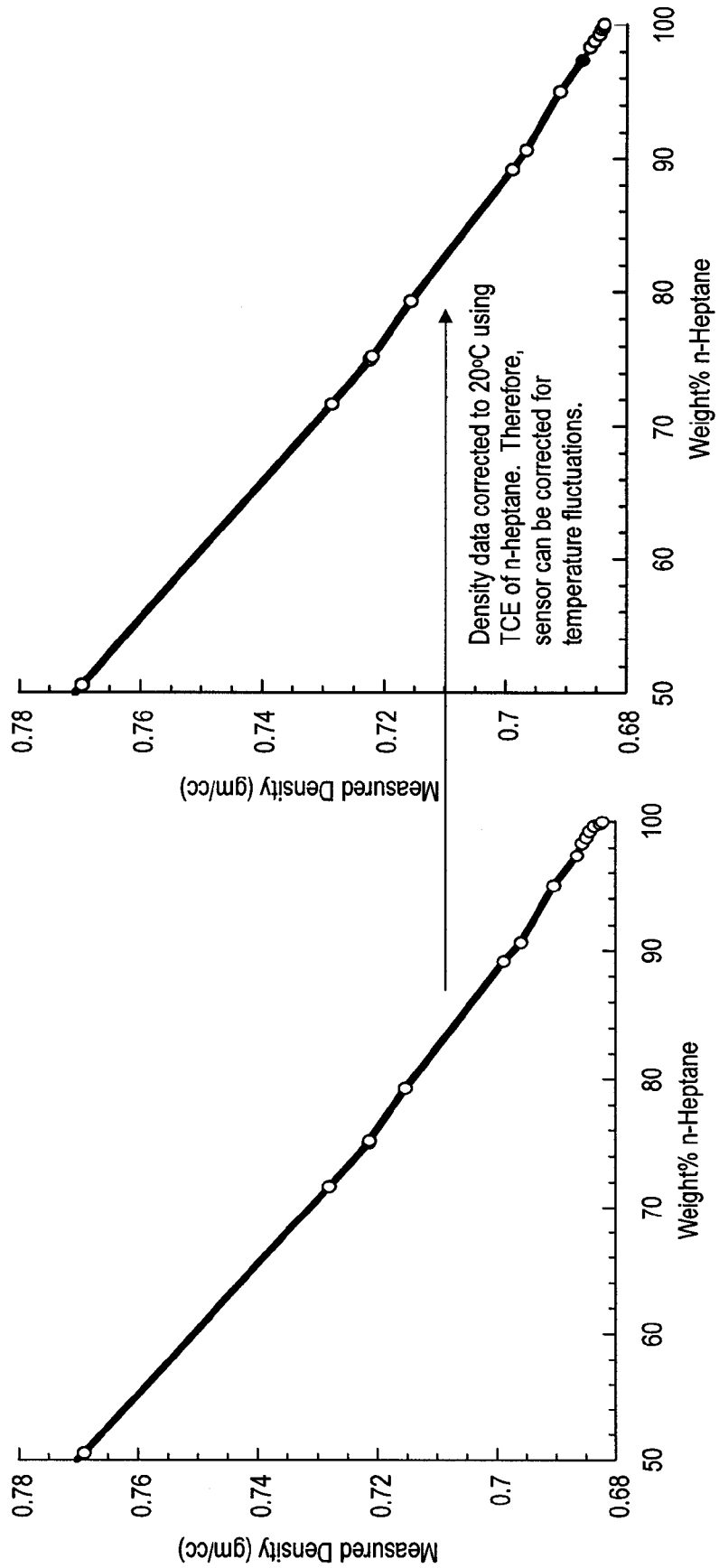
FIG. 31 is a plot of density as measured by a tuning fork resonator as function of wt. % n-heptane, without temperature compensation, in a series of sample mixtures used in Example 11 to simulate the composition of liquid out of the condenser associated with the still pot during a solvent switch distillation in which n-heptane is substituted for ethyl acetate.
FIG. 32 is plot of density vs. wt. % n-heptane obtained in the same simulation depicted in FIG. 31, except that the density responses in FIG. 32 have been corrected to 20° C. based on the thermal coefficient of expansion of n-heptane as obtained from literature.
Figure 33:
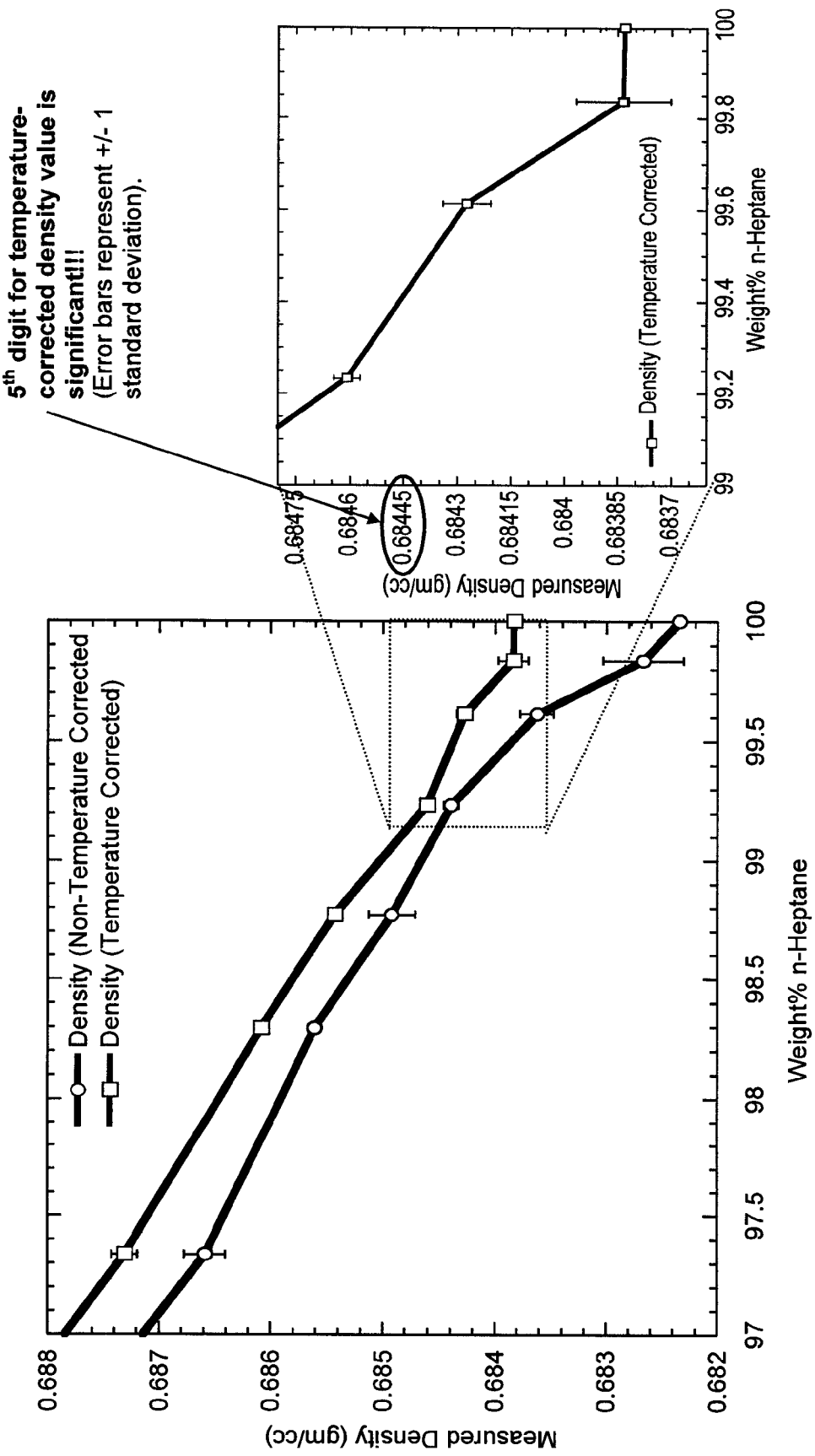
FIG. 33 depicts two plots of density vs. wt. % heptane from the simulation of Example 11, both near the end point of the simulated distillation, the first showing both uncorrected and temperature-corrected data in the range of 97% to 100% by weight n-heptane, the other showing only temperature corrected data and in the range of 99.0 to 100% n-heptane.

As illustrated in FIGS. 31 and 32, where a large change in density results from replacement of ethyl acetate with n-heptane, a generally linear response was observed for density vs. weight % n-heptane in the binary ethyl acetate/heptane system, both at actual measurement temperature (FIG. 31) and after correction to 20° C. (FIG. 32). FIG. 33 directly compares the density vs. n-heptane concentration at high n-heptane content, i.e., near the end point of the solvent switch operation, as measured by the tuning fork resonator without temperature correction, and after correction to 20° C. It may be noted that the limit of correction is better than 0.5 wt. % for the temperature corrected density response.

Figure 34:
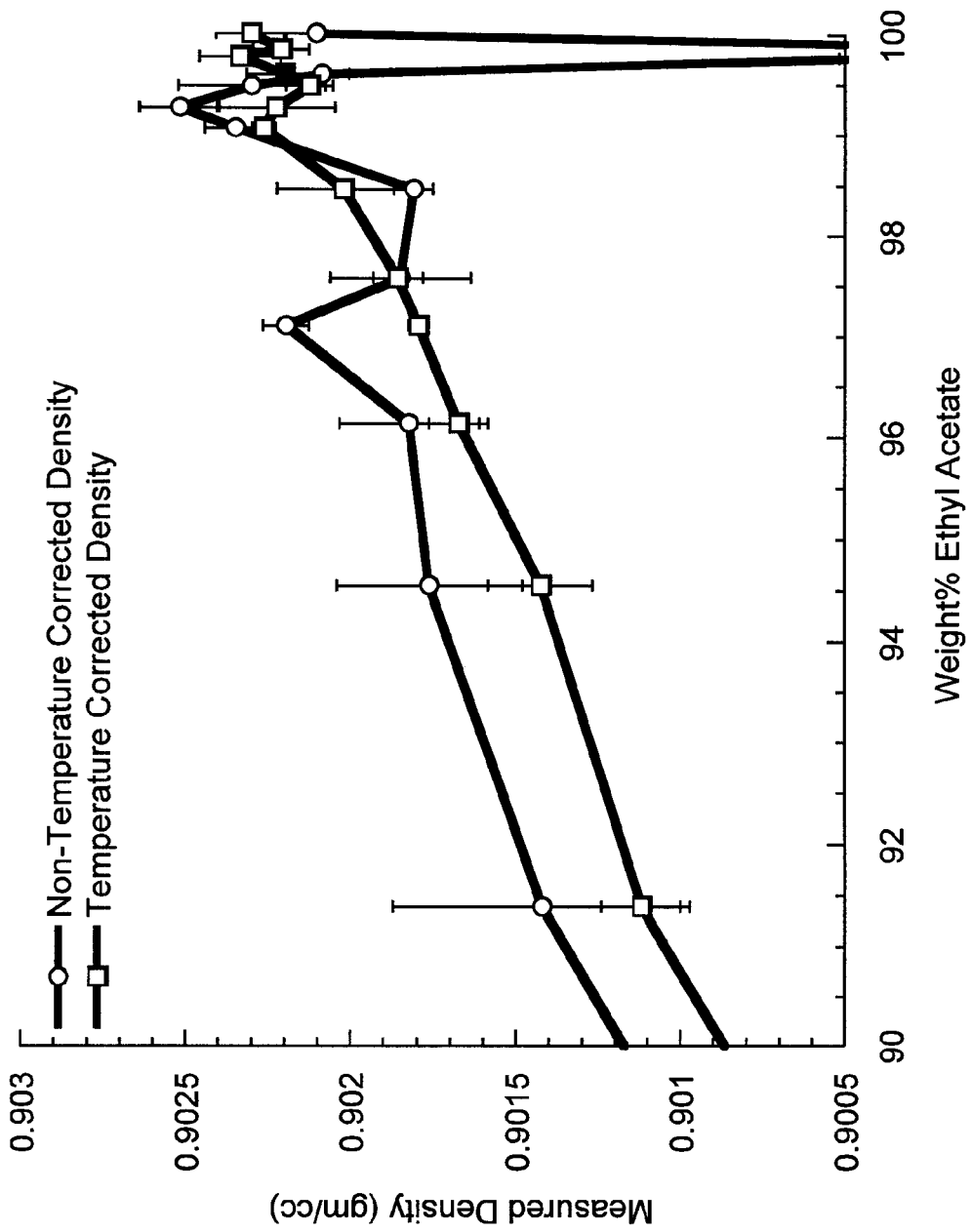
FIG. 34 is a plot of density as measured by a tuning fork resonator as function of wt. % n-heptane in another series of sample mixtures used in Example 11 to simulate the composition in the still pot during a solvent switch distillation in which ethyl acetate is substituted for tetrahydrofuran (THF), showing both the uncompensated and temperature compensated response in the range of 90% to 100% by weight ethyl acetate.

By comparison, where the density range is relatively narrow, as in the replacement of THF with ethyl acetate, the limit of detection expands to about 2 wt. %, still a reasonable degree of precision for most applications. See the density response vs. wt. % ethyl acetate as presented in FIG. 34, both on a non-corrected and temperature corrected basis.

Figure 35:
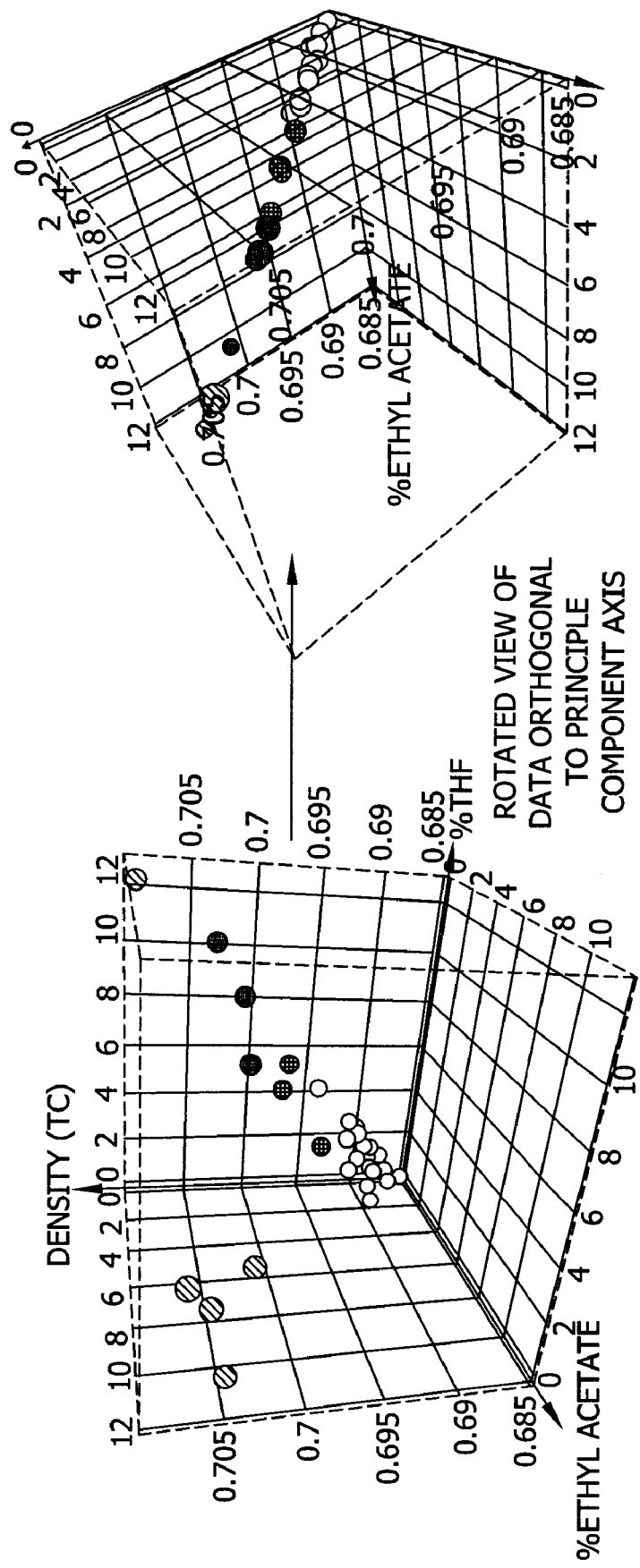
FIG. 35 depicts two dimensional representations of a three dimensional plot of temperature corrected density (as measured with a tuning fork resonator) vs. residual ethyl acetate and THF content near the end point of a solvent switch replacement of ethyl acetate and THF with n-heptane as simulated by a further series of samples prepared and tested per Example 11, the representation on the right consisting of a rotated view orthogonal to the principal component axis.

FIG. 35 presents two dimensional representations of a three dimensional plot of temperature corrected density vs. residual (ethyl acetate/THF) content for the ternary system near the end point of the simulated replacement of ethyl acetate and THF with n-heptane by solvent switch. The second view is rotated from the first orthogonal to the principal component axis. In this system, the limit of detection based on density is better than 1 wt. % residual (ethyl acetate +THF), i.e., >99 wt. % n-heptane.

Figure 36:
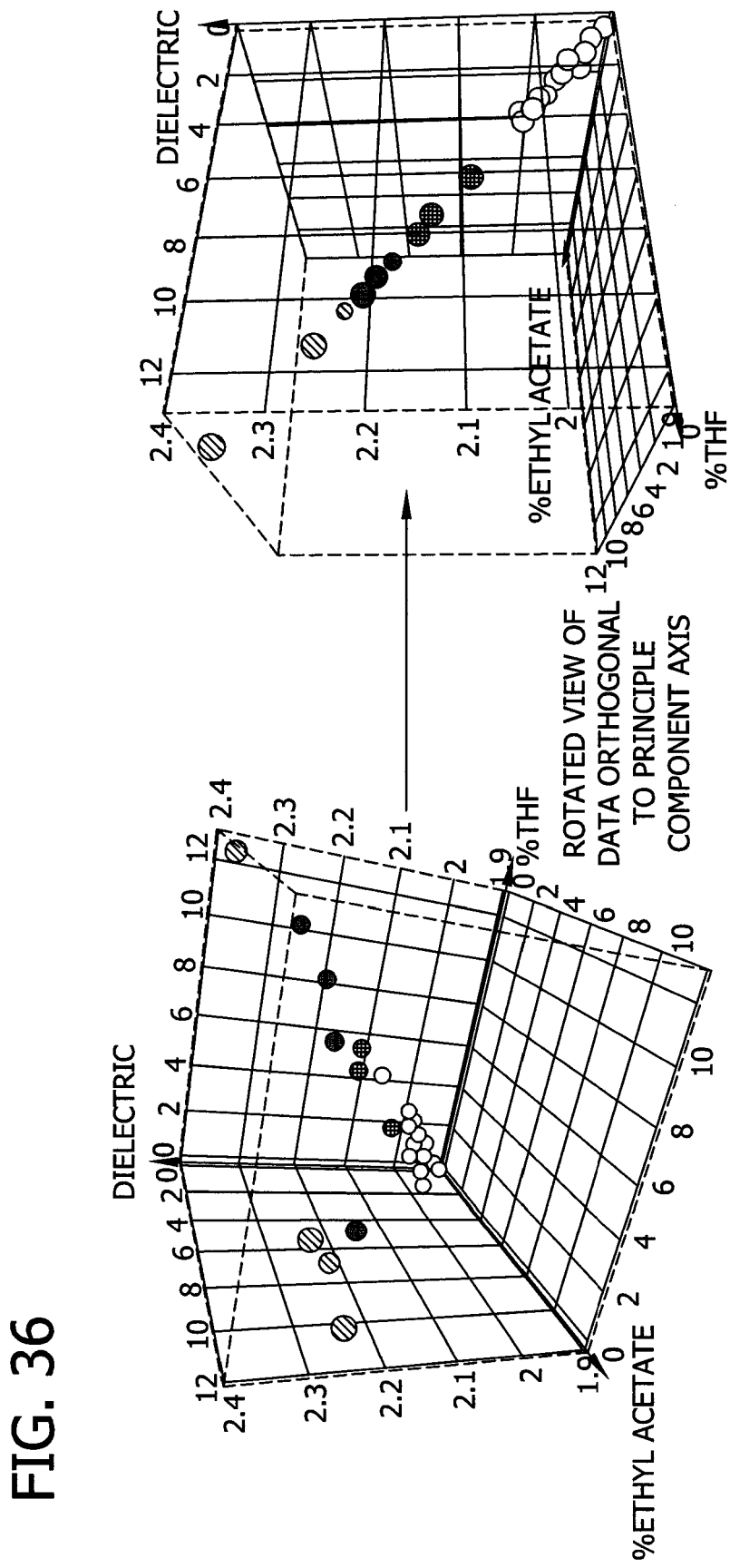
FIG. 36 depicts two plots of the same nature as those of FIG. 35, but for the dielectric component response rather than the density response.

In simulation of the replacement of (ethyl acetate +THF) with n-heptane, the dielectric constant was also monitored. FIG. 36 presents two dimensional representations of the three dimensional plot of dielectric constant vs. residual (ethyl acetate/THF) content for the ternary system near the end point of the simulated solvent switch. The limit of detection based on dielectric constant is also better than 1 wt. % residual (ethyl acetate+THF), i.e., >99 wt. % n-heptane.

Figure 37:
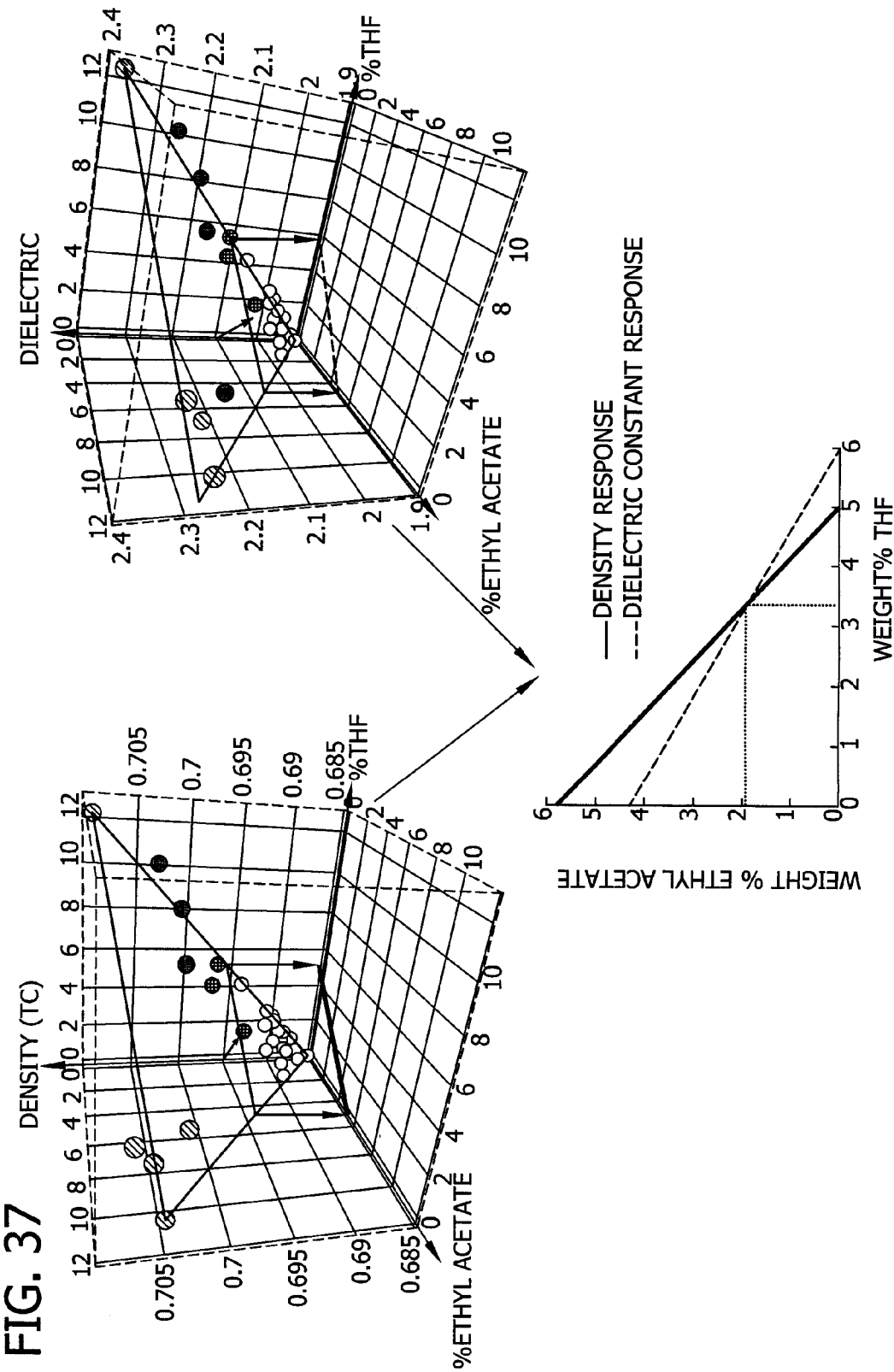
FIG. 37 depicts the three component plots of FIGS. 35 and 36, and demonstrates that, at any given n-heptane concentration in such three component system, the specific ethyl acetate and THF concentrations are determined by the intersection of a line representing the range of ethyl acetate/THF concentrations consistent with the density response with a line representing the range of ethyl acetate/THF concentration consistent with the dielectric constant response.

Considered alone, either the density response or the dielectric constant response is effective to identify the solvent switch end point at which the n-heptane content reaches a desired level, but the relative proportions of ethyl acetate and THF at such n-heptane content can and do vary depending on the original composition of the ethyl acetate/THF solution before the solvent switch operation is commenced. This is illustrated in FIG. 37 with respect to both the density response and the dielectric constant response. Depending on the initial composition, the locus of the operating line of the solvent switch operation varies, and reaches a point for a given n-heptane content at a combination of ethyl acetate and THF content which varies accordingly. For a given density or corresponding to a given n-heptane content, a line may be projected onto the ethyl acetate/THF field which reflects the locus of varying combinations of ethyl acetate and THF content corresponding to that density and n-heptane content. A similar line may be projected onto the ethyl acetate/THF field reflecting the locus of varying combinations of ethyl acetate and THF content corresponding to the dielectric constant at the same n-heptane content. These projections are shown in the ethyl acetate/THF field at the bottom of the three dimensional representations for both density response and dielectric constant response in FIG. 37. While this graphical depiction aids in understanding of the relationship between the composition and the corresponding parameters determined by the response to a flexural resonator, as a practical matter the relationship is typically or preferably determined by multiple linear regression analysis. Standard software is available for conducting the regression analysis, and the algorithm so derived may be programmed into a process monitor, recorder and/or controller for use in management and control of the process.

Where the relationship between ethyl acetate vs. THF content at a given constant n-heptane content based on density response differs from the corresponding relationship based on dielectric constant response, as if typically does the actual combination of ethyl acetate and THF content can be determined by measuring both the density and the dielectric constant during the solvent switch procedure. The actual combination is identified from the intersection of the locus of possible ethyl acetate/THF concentrations based on density vs. the locus of possible concentrations based on dielectric constant, as shown in the two dimensional plot at the bottom of FIG. 37.

In this example, such multiparametric analysis is illustrated only for the combination of density response and dielectric constant response. For the particular solvents involved, the variation of viscosity with composition is relatively modest, so that viscosity does not afford the precision of composition determination that is provided by either density, dielectric constant or the combination thereof. However, in other systems, viscosity can provide precise, in some instances even the most precise, alternative for determination of the end point, and the combination of viscosity with either density or dielectric constant may yield the most definitive data for specifying the actual combination of residual solvents in a ternary system.

Multiparametric analysis may also be applied in a four component system wherein each of the parameters of density, viscosity, and dielectric constant varies significantly with composition. As the number of variables increases, graphical geometric depiction becomes impractical, but the system can still be usefully modeled by multiple linear regression analysis.

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods and processes without departing from the scope of the invention, it is intended that all matter contained in the above description and shown in the accompanying drawings shall be interpreted as illustrative and not in a limiting sense.

What is claimed is:

1. A system for monitoring a unit operation that includes separating one or more components of a multi-component composition by distillation, the system comprising:
   a fluidic system configured for distillation, the fluidic system comprising (i) a process container for providing a multi-component composition comprising one or more liquid components, (ii) a heat source associated with the process container and adapted for vaporizing at least a portion of at least one liquid component of the composition to form a vapor, (iii) a condenser in fluid communication with the process container for receiving the vapor, (iv) a heat sink associated with the condenser for condensing the vapor to form a condensate, and (v) a distillate receiver for recovering at least a portion of the condensate as a distillate, and a sensor comprising a flexural resonator, the sensor being configured in association with the fluidic system such that a sensing surface of the flexural resonator can contact a fluid within the fluidic system, the fluid being the multi-component composition, the vapor, the condensate or the distillate, the sensor further comprising an electrical circuit in signaling communication with the flexural resonator, the electrical circuit comprising signal processing circuitry or data retrieval circuitry or combinations thereof.

2. The system of claim 1 wherein the sensor is a first sensor comprising a first flexural resonator, the first sensor being configured in association with the fluidic system such that a sensing surface of the first flexural resonator can contact a first fluid within the fluidic system, the system further comprising a second sensor comprising a second flexural resonator, the second sensor being configured in association with the fluidic system such that a sensing surface of the second flexural resonator can contact a second fluid within the fluidic system, the second fluid being the multi-component composition, the vapor, the condensate or the distillate, the second sensor further comprising an electrical circuit in signaling communication with the second flexural resonator, the electrical circuit comprising signal processing circuitry or data retrieval circuitry or combinations thereof.

3. A system as set forth in claim 1 wherein the fluidic system is configured to limit flow of the distillate from the distillate receiver to the process container.

4. A system as set forth in claim 1 wherein the fluidic system comprises a fractionating column.

5. A system as set forth in claim 1 wherein said fluidic system is configured for a batch distillation and the system is adapted to detect a condition indicative of an endpoint of the batch distillation using a signal from the flexural resonator.

6. A system as set forth in claim 5 wherein the flexural resonator comprises a tuning fork resonator.

7. A system as set forth in claim 1 wherein the system is adapted to automatically adjust at least one of a temperature of a fluid in the fluidic system, a feed rate, a reflux ratio, a head pressure, a boilup rate, and a level of a fluid in the fluidic system using a signal from the flexural resonator.

8. A system as set forth in claim 7 wherein the fluidic system is configured for a semi-continuous or continuous distillation.

9. A system as set forth in claim 7 wherein the flexural resonator comprises a tuning fork resonator.

10. A system as set forth in claim 1 wherein the sensor is configured in association with the fluidic system such that a sensing surface of the flexural resonator can contact at least one of the vapor, the condensate, and the distillate.

11. A system as set forth in claim 1 further comprising a distillate discharge line adapted to remove the distillate from the distillate receiver.

12. A system for monitoring a unit operation that includes separating one or more components of a multi-component composition by distillation, the system comprising:

a fluidic system configured for distillation, the fluidic system comprising (i) a process container for providing a multi-component composition comprising one or more liquid components, (ii) a heat source associated with the process container and adapted for vaporizing at least a portion of at least one liquid component of the composition to form a vapor, (iii) a condenser in fluid communication with the process container for receiving the vapor, (iv) a heat sink associated with the condenser for condensing the vapor to form a condensate, and (v) a distillate receiver for recovering at least a portion of the condensate as a distillate, and an on-line sensor other than a temperature sensor, a pressure sensor and a flow sensor, the on-line sensor being configured in association with the fluidic system such that the sensor can monitor a fluid within the fluidic system, the fluid being the vapor, the condensate or the distillate.

13. The system of claim 12 wherein the on-line sensor is a sensor adapted for determining one or more fluid-composition-dependent properties of the vapor, the condensate or the distillate.

14. The system of claim 12 wherein the on-line sensor is a sensor adapted for determining one or more properties of the vapor, the condensate or the distillate, the sensor being selected from a viscosity sensor, a density sensor, an electrical property sensor, an optical property sensor and combinations thereof.

15. The system of claim 14 wherein the on-line sensor is selected from the group consisting of a viscosity sensor, a density sensor, a dielectric sensor and combinations thereof.

16. The system of claim 14 wherein the on-line sensor is an electrical property sensor selected from the group consisting of a dielectric sensor, a conductivity sensor and combinations thereof.

17. The system of claim 14 wherein the on-line sensor is an optical property sensor, the sensor further comprising a radiation source configurable for irradiating a portion of the vapor, the condensate or the distillate with electromagnetic radiation, and one or more components for observing a response selected from the group consisting of absorbance, reflectance, scattering, refraction and combinations thereof.

18. The system of claim 12 wherein the on-line sensor comprises a refractive index sensor.

19. The system of claim 12 wherein the on-line sensor comprises a mechanical resonator sensor.

20. The system of claim 12 adapted for process control, the system further comprising, in addition to the sensor, a processor for processing a monitored response of the sensor to determine whether a control action is necessary, one or more process control elements for effecting any necessary control action, and appropriate communication paths between the sensor, the processor and the one or more process control elements.

* * * * *

UNITED STATES PATENT AND TRADEMARK OFFICE
CERTIFICATE OF CORRECTION

| | | |
|---|---|---|
| PATENT NO. | : 7,603,889 B2 | Page 1 of 1 |
| APPLICATION NO. | : 11/278340 | |
| DATED | : October 20, 2009 | |
| INVENTOR(S) | : Stephen Cypes et al. | |

It is certified that error appears in the above-identified patent and that said Letters Patent is hereby corrected as shown below:

On the Title Page, Item (54) and col. 1, lines 1-3, please correct the title as follows:
"SYSTEM FOR MONITORING AND CONTROLLING UNIT OPERATIONS THAT INCLUDE DISTILLATION" should read --SYSTEMS FOR MONITORING AND CONTROLLING UNIT OPERATIONS THAT INCLUDE DISTILLATION--.

Signed and Sealed this
Twelfth Day of April, 2011

David J. Kappos
*Director of the United States Patent and Trademark Office*